(12) United States Patent
Mauclere et al.

(10) Patent No.: US 7,534,877 B2
(45) Date of Patent: May 19, 2009

(54) NON-M, NON-O HIV-1 STRAINS, FRAGMENTS AND USES

(75) Inventors: Phillippe Mauclere, Bordeaux (FR); Ibtissam Loussert-Ajaka, Sartrouville (FR); Francois Simon, Paris (FR); Sentob Saragosti, Billancourt (FR); Francoise Barre-Sinoussi, Moulimeaux (FR)

(73) Assignees: Institute National de la Sante et de la Recherche Medicale-Inserm, Paris (FR); Assitance Publique-Hopitaux de Paris, Paris (FR); Institut Pasteur, Paris (FR)

( * ) Notice: Subject to any disclaimer, the term of this patent is extended or adjusted under 35 U.S.C. 154(b) by 209 days.

(21) Appl. No.: 11/226,240

(22) Filed: Sep. 15, 2005

(65) Prior Publication Data

US 2007/0190524 A1 Aug. 16, 2007

Related U.S. Application Data

(62) Division of application No. 10/301,661, filed on Nov. 22, 2002, now Pat. No. 7,030,234, which is a division of application No. 09/319,588, filed as application No. PCT/FR97/02227 on Dec. 8, 1997, now Pat. No. 6,509,018.

(30) Foreign Application Priority Data

Dec. 9, 1996 (FR) .................................. 96 15087

(51) Int. Cl.
*C07H 21/04* (2006.01)
*C12Q 1/68* (2006.01)
*C12P 19/34* (2006.01)

(52) U.S. Cl. .............. 536/23.73; 536/24.32; 536/24.34; 435/6; 435/91.2; 424/208.1

(58) Field of Classification Search ........................ None
See application file for complete search history.

(56) References Cited

U.S. PATENT DOCUMENTS 5,420,030 A * 5/1995 Reitz et al. ............... 435/235.1
5,576,000 A * 11/1996 Reitz et al. ............... 424/188.1
5,869,313 A * 2/1999 Reitz et al. ............... 435/235.1

FOREIGN PATENT DOCUMENTS

WO 86/02383 4/1986
WO 94/28915 A1 12/1994

OTHER PUBLICATIONS

Chen et al. Current Pharmaceutical Design 2440, vol. 10, pp. 4065-4070.*
Huet, et al., "A highly defective HIV-1 strain isolated from a healthy Gabonese individual presenting an atypical Western blot", AIDS, vol. 3, No. 11, Nov. 1989, pp. 707-715.
Huet, et al., "Genetic organization of a chimpanzee lentivirus related to HIV-1", Nature, vol. 45, No. 6273, May 24, 1990, pp. 356-359.
Inagaki, et al., "Cloning and functional characterization of a third pituitary adenylate cyclase-activating polypeptide receptor subtype expressed in insulin-secreting cells", Proceedings of the National Academy of Sciences of USA., vol. 91, Mar. 1994, pp. 2679-2683.
Muster et al., J. Virol., vol. 68, 1994, pp. 4031-4034.
Tojo, et al., "Cloning and nucleotide sequence of the Myxococcus xanthus lon gene: indispensibility of lon for vegetative growth", Journal of Bacteriology, vol. 175, No. 8, Apr. 1993, pp. 2271-2277.
Ou, et al., (Lacent 1993, vol. 341, pp. 1171-1174).

* cited by examiner

*Primary Examiner*—Bruce Campell
*Assistant Examiner*—Bao Qun Li
(74) *Attorney, Agent, or Firm*—Morgan, Lewis & Bockius LLP

(57) ABSTRACT

Retroviral strains of the non-M, non-O HIV-1 group, in particular a strain designated YBE30, its fragments and also its uses as a diagnostic reagent and as an immunogenic agent.

The HIV-1 viruses which differ both from the M group and the O group exhibit the following characteristics:
  little or no serological reactivity with regard to the proteins of the M and O groups and strong serological reactivity with regard to the proteins which are derived from the strain YBF30 according to the invention or the strain CPZGAB SIV;
  absence of genomic amplification when using primers from the env and gag regions of the M and O HIV-1 groups;
  genomic amplification in the presence of primers which are derived from the YBF30 strain according to the invention; and
  homology of the products of the envelope gene which is greater than 70% with regard to the YBF30 strain.

10 Claims, 20 Drawing Sheets

| Name | Region | Sequence |
|---|---|---|
| YLG | ltr | A T T G C G T A C T C A C A C T T C C G |
| LPBS.1 | ltr | G G C A A G C A G G G A G C T G G |
| GAG Y AS1.1 | ltr | T C C T T G A G C A G T C T G G A C |
| GAG Y AS1 | gag | G A A C A G G A G G A T T A G C A G |
| Gag 6 | gag | A G C A G A G G C T A T G T C A C A |
| GAG Y S1 | gag | T G T A A G G C C C T A G A A G A G |
| GAG Y S1.1 | gag | A C A G A G A A C T C T C T G T A C |
| GAG Y S1.2 | gag | A A G A A A A G C A G T T G G T A - C |
| YRT AS 1.3 | pol | T T T C T T C C C T G T A T G T C |
| YRT AS1.2 | pol | G T T A T A T G G A T T C T C A G G |
| YRT AS1.1 | pol | T G G C A G C A C A T T A T A C T G G |
| YRT2 | pol | A T C A T T T A C C A G T A C A T G G A C G A |
| YRT AS1 | pol | T G T C A G G G T C G T A A A G C |
| YRT2-1 | pol | T C C T C T G G A T G G G A T A T G |
| YRT2-2 | pol | T C T A T C C A G G A A T C A G A G |
| YRT-3 | pol | A A T G A G A T C T G C C C A T A C |
| YRT2-4 | pol | T G A C A G A T A G G G A A G A C |
| 4481-1 | pol | A A C C G C C A T T T G C A C T G C |
| 4481-2 | pol | A C A T G G A C C G C C A C A A G G |
| 4235.1 | pol | A G C A A C A G A C A T A C A G A C |
| 4235.2 | vif | A A A G T A G T C C A C G T A G G |
| 4235.3 | tat | A T A T C C C A G T A G G T C A G G |
| 4235.4 | tat | T C T A G C A C T A A C A G C C T G |
| SK69.6 | env | A C T C T T A C T G C T C T G A G G |
| SK69.5 | env | C C A T A G T A C A C T G T T A C C |
| SK69.4 | env | C A T A G C T A T C G T T A C A A A G C |
| SK69.3 | env | T C A T A A T G G C A A A G C C T G |
| SK69.2 | env | C T A T T C C A C A T T G G T T C C |
| SK69.1 | env | A T T C T A G A A C C A G T C C A G |
| SK68.1 | env | C C T T A G G G A T C A G C A A A T C C |
| SK68.2 | env | T G G G A C A G T C T G T G G A G C |
| SK68.3 | env | T T C T C A G C T C T T G T C T G G |
| LSI AS1.3 | nef | A T T A A G C A A G C T G A T A G C |
| LSIAS1.2 | nef | T G T G C T T C T A G C C A A G |
| LSI AS 1.1 | ltr | G C T C C A T G T T G A C A T A T G |
| LSi A1 | ltr | A G A G A G A C C C A G T A C A A G |
| YLPA | ltr | A T A A A A G C A G C C G C T T C T C G |

FIGURE 1

1386 nt after "gapstripping" (after rearrangement of the alignment of the sequences)
Phylip n-j tree with "bootstrap" values (100 "bootstraps")

YBF30 Tat
292 nt after "gapstripping"
PHYLIP n-j tree with "bootstrap" values (100 "bootstraps")

YBF30 Nef
615 nt after "gapstripping"
PHYLIP n-j tree with "bootstrap" values (100 "bootstraps")

Percentage genetic distance between YBF30 and HIV-1/CPZSIV

| | Gag | Pol | Vif | Vpr | Vpu | Tat | Rev | Env gp120 | Nef |
|---|---|---|---|---|---|---|---|---|---|
| HIV-1 M | 30-33 | 22-24 | 27.5-30 | 27-30 | 66.6-80 | 22-27.6 | 33.8-42 | 50-53 | 34.6-39 |
| HIV-1 O | 37-38 | 33-34 | 42-45.6 | 32-36 | >100 | 46-47.7 | 80-88 | 73-74 | 52.8-53 |
| CPZGAB | 32 | 26.8 | 40.3 | 28.8 | >100 | 27.8 | 56.8 | 50 | 33.7 |
| CPZANT | 45 | 41.2 | 57.1 | 57.4 | >100 | 55 | ND* | 74.5 | ND* |

ND: not determined

FIGURE 20

SEQUENCE LISTING

<160> NUMBER OF SEQ ID NOS: 100

<210> SEQ ID NO 1
<211> LENGTH: 9183
<212> TYPE: DNA
<213> ORGANISM: Human immunodeficiency virus type 1

<400> SEQUENCE: 1

```
cttctcgctt gtactgggtc tctcttgctg gaccagatta gagcctggga gctctctggc      60
tagcagggaa cccactgctt aagcctcaat aaagcttgcc ttgagtgcta agtggtgtg     120
tgcccatcca ttcggtaact ctggtaccta gagatccctc agaccatcta gactgagtga    180
aaatctctag cagtggcgcc cgaacaggga cttgaaaaca gaaagtagaa ccggaggctg    240
aatctctcga cgcaggactc ggctcgttgg tgcacacagc gagaggcgag gcggcggaag    300
tgtgagtacg caattttgac tggcggtggc cagaaagtag gagagaggat gggtgcgaga    360
gcgtcagtgt taacaggggg aaaattagat caatgggaat caattttattt gagaccaggg    420
ggaaagaaaa aatacagaat gaaacattta gtatgggcaa gcaggagct ggaaagattc      480
gcttgtaacc caggtctcat ggacacagcg gacggctgtg ccaagttact aaatcaatta    540
gaaccagctc tcaagacagg gtcagaagaa ctgcgtcctt tatataacgc tctagcagtt    600
ctttattgtg tccatagtag gatacagata cacaacacac aggaagcttt ggacaagata    660
aaagagaaac aggaacagca caagcccgag ccaaaaaacc cagaagcagg gcagcggca     720
gcaactgata gcaatatcag taggaattat cctctagtcc agactgctca aggacaaatg    780
gtacatcagc cgctgacacc cagaacctta aatgcttggg tgaaagtgat agaggagaag    840
gcctttagtc cagaagtaat accaatgttt atggccttgt cagaaggggc aacgccctca    900
gatctaaata ctatgttaaa tacagtaggg ggacatcagg cagcaatgca gatgctgaag    960
gaagtcatca atgaggaagc agcagactgg gataggacac atccagtccc tgtgggacca   1020
ctaccccag ggcaactgag agaccctaga ggaagtgata tagcaggaac aactagcacc    1080
ctggcagaac aggtggcttg gatgactgct aatcctcctg ttccagtagg agatatttat    1140
agaagatgga tagtcctggg gttaaacaga attgtgagaa tgtatagtcc tgtcagcatt    1200
ctagagatca aacaaggacc aaaagaaccc ttcagagact atgtagacag gttctacaaa    1260
actctaagag cagagcaggc aacacaggaa gtaaagaatt ggatgacaga acactcttta    1320
gtacaaaatg caaacccaga ttgtaaacag ctcctaaaag cattagggcc aggagctacc    1380
ttagaagaga tgatgacggc ctgccaggga gtgggggggac cagcacataa ggcaagagtg   1440
ctagcagagg ctatgtcaca ggtgcagcag ccaacaacta gtgtctttgc acaaggggaa   1500
aactttaaag gcataaggaa acccattaaa tgtttcaatt gtggcaaaga gggccatttg    1560
gcaagaaact gtaaggcccc tagaagagga ggctgttgga agtgtgggca agaaggacat    1620
caaatgaaag attgtaaaaa tgaaggaaga caggctaatt ttttagggaa gagctggtct    1680
cccttcaaag ggagaccagg aaacttcccc cagacaacaa caaggaaaga gcccacagcc    1740
ccgccactag agagttatgg gtttcaggag gagaagagca cacagggga ggagatgcag     1800
gagaaccagg agaggacaga gaactctctg tacccacctt taacttccct cagatcactc    1860
tttggcaacg acccgtcatc acagtaaaaa tagggaaaga agtaagagaa gctctttag     1920
atacaggagc tgatgataca gtaatagaag agctacaatt agagggaaaa tggaaaccaa    1980
aaatgatagg aggaattgga ggatttatca agtgagaca atatgataat ataacagtag    2040
```

```
acatacaggg aagaaaagca gttggtacag tattagtagg accaacacct gttaatatta    2100
taggaagaaa tcttttaacc cagattggct gtactttaaa ttttccaata agtcctattg    2160
aaactgtacc agtaaaatta aaccaggaa tggatggccc aaaggtaaaa caatggcctt     2220
tgacaacaga aaaatagag gcattaagag aaatttgtac agaaatggaa aaggaaggaa     2280
aaatttctag aatagggcct gagaatccat ataacactcc aatttttgct ataaaaaga    2340 aagatagcac taaatggaga aaattagtag atttcaggga attaaataaa aggacccaag    2400
atttttggga agtgcagcta ggaattccac atccagcagg attaaagcag aaaaaatcag    2460
tgacagtttt ggatgtagga gatgcttatt tttcatgtcc cttggacaaa gattttagaa    2520
agtatacagc ttttaccata cctagtataa acaatgagac acctggtatt agataccagt    2580
ataatgtgct gccacaaggc tggaaagggt caccagcaat ttttcagagt acaatgacaa    2640
aaattctaga accattcaga gagaaacatc cagagataat catttaccag tacatggatg    2700
acctctatgt gggatctgac ttagaactag cacaacatag agaggcagta aagaccttta    2760
gagatcatct tttgaagtgg ggctttacga cccctgacaa aaaacatcag aaggaacccc    2820
cgttcctctg gatgggatat gaactccatc cagacaaatg gacagtccag ccaataaagt    2880
taccagaaaa ggatgtatgg actgtcaatg atatacagaa attagtagga agttaaatt     2940 gggcaagtca gatctatcca ggaatcagag taaaacagct ctgtaaatta atcagaggaa    3000
ccaaagcttt gacagaagta gtcaacttta cagaagaagc agaattagaa ctagcagaaa    3060
acagggagat attaaaagaa cccctgcatg gagtctatta tgacccagga aaagaattag    3120
tagcagaaat tcaaaagcaa ggacaaggtc agtggacata tcagatttat caggagttac    3180
ataaaaattt aaaaacagga aagtatgcaa aaatgagatc tgcccatact aatgatataa    3240
aacagttagt tgaagtggta aggaaagtgg caacagaaag tatagtaatt tggggaaaga    3300
ctcctaaatt tagattacca gtacaaaagg aagtgtggga ggcatggtgg accgatcatt    3360
ggcaagcaac ttggattcct gagtgggaat ttgtcaacac tcctcccctt gtaaaattat    3420
ggtatcagtt agaaacagag ccaatcagtg gggcagaaac tttctatgta gatggagcag    3480 ctaatagga acaaaattg ggaaaagcag gttttgtgac agatagggga agacagaaag    3540
tggtctctat tgcagacacc accaatcaaa aggctgagtt acaagctatc cttatggcct    3600
tacaagagtc aggacgggat gtaaacatag tcactgactc tcagtatgct atgggaataa    3660
ttcattcaca gccagataaa agtgaatcag aattggtgag ccaaataata gaagagctca    3720 taaaaagga agagtttat ctctcttggg tacctgcaca taaaggtatt ggaggaaatg     3780
agcaggtaga caaattagtt agctcaggaa ttagaaaaat attattccta gatggtatag    3840
aaaaagccca agaagatcat gacagatatc acagcaattg gaaagcaatg gccagtgatt    3900
ttaacttacc ccccatagtg gcaaaagaaa tagtagccag ctgtgacaaa tgccagctaa    3960 aagggaagc catgcatgga caggtcaatt gtagtccagg agtgtggcaa ttagattgta    4020
cacacttaga gggaaaaatc atcccttgtgg cggtccatgt ggccagtggc tacttagaag    4080
cagaagttat tcctgcagag acaggacagg aaacagcata ttttattta aagttagctg     4140 gaagatggcc agtaaaagtt atacacactg ataatggatc caatttcact agtgccactg    4200
taaaagcagc ctgttggtgg gcaaatatca acaggaatt tgggataccc tacaatcctc    4260
aaagtcaggg agcagtagag tccatgaata aagaattaaa gaaaattata ggacaaatca    4320
gagatcaagc agaacatcta aagacagcag tgcaaatggc ggttttcatt cacaatttta    4380
```

```
aaagaaaagg ggggattggg gggtacactg caggggaaag aataatagac ataatagcaa   4440
cagacataca gacaacaaat ttacaaacac aaattttaaa agttcaaaat tttcgggttt   4500
attacagaga cagcagagat cccatttgga aaggaccagc caaacttctg tggaaaggag   4560 aagggcagt ggtaattcaa gataacgggg atataaaagt agtcccacgt aggaaagcaa   4620
aaataattag ggattatgga aaacagatgg caggtgatgg ttgtgtggca agtggacagg   4680
atgaaaatca ggaaatggaa tagcttagta aaacatcata tgtatgtgtc aaaaaaggca   4740
aaaggatggt attatagaca tcattatgaa acacatcacc caaaaataag ttcagaagta   4800
catatcccag taggtcaggc aagattagtg acagtcactt attgggggct aacaacagga   4860
gaacagtctt ggcatctagg acatggagta tccatagaat ggagactaag aaaatacaag   4920
acacaagttg atcctgaaat ggcagacaag ctaatacatc ttcattattt tgattgtttt   4980
acagcctctg ccataaggca agcggtctta gggagaccag tattacctag gtgtgaatat   5040
ccagcagggc acaaacaggt aggcacccta caatatctag cactaacagc ctgggtggga   5100
gcaaagaaga gaaagccacc cttacctagt gtgactaagc taacagaaga tagatggaac   5160
gagcaccaga agatgcaggg ccacagaggg aaccctataa tgaatgggca ctagaattat   5220
tagaagaatt aaaaaatgaa gctgtgcgcc attttccaag gatttggcta catgggttag   5280
gacaacacat ctataacaca tatggagaca cctgggaggg ggtagaggca attatcagga   5340
tactacaaca attactgttt atccattata ggattggctg ccagcacagc agaatatgga   5400
tcactcctca aaggagaagg aatgaaacca gtagatccta gattagagcc ctggaatcat   5460
ccaggaagcc aacctaaaac agcttgcaat aattgctatt gtaaagatg ttgctatcac   5520 tgcttatatt gcttcacaaa gaaaggctta ggcatctcat atggcaggaa gaagcggagt   5580
caacgacgaa gaactcctca gagcagtaag agtcatcaag atcttatacc agagcagtaa   5640
gtaaaacctg tatatatgct gtcattggga ttcatagcgt taggagcagc agttagcata   5700
gcagtaatag tctgggcatt actatataga gaatataaga aaataaaatt gcaggaaaaa   5760
ataaaacaca taagacagag aataagagaa agagaagaag atagtggcaa tgaaagtgat   5820
ggggatgcag agtggttgga tggggatgaa gagtggttgg ttactcttct atcttctagt   5880
aagcttgatc aaggtaattg ggtctgaaca acattgggta acagtgtact atggggtacc   5940
agtatggaga gaagcagaga caactctttt ctgtgcttca gatgctaaag cccatagtac   6000
agaggctcac aacatctggg ccacacaagc atgtgttcct actgatccca atccacaaga   6060
agtgctatta cccaatgtaa ctgaaaaatt taatatgtgg gaaaataaaa tggcagacca   6120
aatgcaagag gatattatca gtctgtggga acagagctta aagccctgtg ttaaattaac   6180
cccattatgt gtaactatgc tttgtaacga tagctatggg gaggaaagga acaatacaaa   6240
tatgacaaca agagaaccag acataggata caaacaaatg aaaaattgct cattcaatgc   6300
aaccactgag ctaacagata aaagaagca agttactct ctgttttatg tagaagatgt   6360
agtaccaatc aatgcctata ataaaacata taggctaata aattgtaata ccacagctgt   6420
gacacaagct tgtcctaaga cttcctttga gccaattcca atacattact gtgcaccacc   6480
aggctttgcc attatgaaat gtaatgaagg aaactttagt ggaaatggaa gctgtacaaa   6540
tgtgagtact gtacaatgca cacatggaat aaagccagtg atatccactc agttaatcct   6600
aaatggaagc ttaaatacag atggaattgt tattagaaat gatagtcaca gtaatctgtt   6660
ggtgcaatgg aatgagacag tgccaataaa ttgtacaagg ccaggaaata tacaggagg   6720 acaggtgcag ataggacctg ctatgacatt ttataacata gaaaaaatag taggagacat   6780
```

```
tagacaagca tactgtaatg tctctaaaga actatgggaa ccaatgtgga atagaacaag    6840
agaggaaata aagaaaatcc tggggaaaaa caacataacc ttcagggctc gagagaggaa    6900
tgaaggagac ctagaagtga cacacttaat gttcaattgt agaggagagt ttttctattg    6960
taacacttcc aaattattta atgaggaatt acttaacgag acaggtgagc ctattactct    7020
gccttgtaga ataagacaga ttgtaaattt gtggacaagg gtaggaaaag gaatttatgc    7080
accaccaatt cggggagttc ttaactgtac ctccaatatt actggactgg ttctagaata    7140
tagtggtggg cctgacacca aggaaacaat agtatatccc tcaggaggaa acatggttaa    7200
tctctggaga caagagttgt ataagtacaa agtagttagc atagaaccca taggagtagc    7260
accaggtaaa gctaaaagac gcacagtgag tagagaaaaa agagcagcct ttggactagg    7320
tgcgctgttt cttgggtttc ttggagcagc agggagcact atgggcgcag cgtcaataac    7380
gctgacggta caggcccgga cattattatc tgggatagtg caacagcaga atattctgtt    7440
gagagcaata gaggcgcaac aacatttgtt gcaactctca atctgggggca ttaaacagct    7500 ccaggcaaaa gtccttgcta tagaaagata ccttagggat cagcaaatcc taagtctatg    7560
gggctgctca ggaaaaacaa tatgctatac cactgtgcct tggaatgaga cttggagcaa    7620
caatacctct tatgtacaa tctgaataa tttaacctgg caacaatggg atgaaaagt    7680 aagaaactat tcaggtgtca tttttggact tatagaacag gcacaagaac aacagaacac    7740
aaatgagaaa tcactcttgg aattggatca atgggacagt ctgtggagct ggtttggtat    7800
tacaaaatgg ctgtggtata taaaaatagc tataatgata gtagcaggca ttgtaggcat    7860
aagaatcata gtatagtaa taactataat agcaagagtt aggcagggat attctcccct    7920
ttcgttgcag accccttatcc caacagcaag gggaccagac aggccagaag aaacagaagg    7980
aggcgttgga gagcaagaca gaggcagatc cgtgcgatta gtgagcggat tctcagctct    8040
tgtctgggag gacctccgga acctgttgat cttcctctac accgcttga cagactcact    8100 cttgatactg aggaggactc tggaactcct gggacagagt ctcagcaggg gactgcaact    8160
actgaatgaa ctcagaacac acttgtgggg aatacttgca tattgggga aagagttaag    8220 ggatagtgct atcagcttgc ttaatacaac agctattgta gtagcagaag gaacagatag    8280
gattatagaa ttagcacaaa gaataggaag gggaatatta cacataccta aagaatcag    8340 acaaggccta gaaagagcac tgatataaga tgggaaagat ttggtcaaag agcagcctag    8400
taggatggcc agaaatcaga gaaagaatga gaagacaaac gcaagaacca gcagtagagc    8460
cagcagtagg agcaggagca gcttctcaag atctagctaa tcgaggggcc atcaccataa    8520
gaaatactag agacaataat gaaagtatag cttggctaga agcacaagaa gaagaagagg    8580
aagtaggctt tccagtacgc cctcaggtac cattaaggcc aataacctat aaacaggctt    8640
ttgatctttc cttctttta aaagataagg ggggactgga agggctagtt tggtccagaa    8700
aaaggcaaga tattctagac ctctggatgt atcacacaca aggcatcctc cctgactggc    8760
ataactacac accagggcca ggaattagat accccgtaac ctttggatgg tgcttcaaac    8820
tagtaccatt gtcagctgaa gaagtagaag aggctaatga aggagacaac aatgccctct    8880
tacaccccat atgtcaacat ggagcagatg atgatcataa agaagtgttg gtgtggcgat    8940
ttgacagctc cctagcaaga agacatgtag caagagagct gcatccggag ttttacaaga    9000
actgctgaca agggacttta ctgctgacaa gggactttat acttgggac tttccgccag    9060 ggactttcca ggggaggtgtg gttgggggag tggcttgccc tcagagctgc ataaaagcag    9120
```

```
ccgcttctcg cttgtactgg gtctctcttg ctggaccaga ttagagtctg ggagcatatt      9180
ggg                                                                    9183

<210> SEQ ID NO 2
<211> LENGTH: 813
<212> TYPE: DNA
<213> ORGANISM: Human immunodeficiency virus type 1

<400> SEQUENCE: 2
ttggaagggc tagtttggtc cagaaaaagg caagatattc tagacctctg gatgtatcac       60
acacaaggca tcctccctga ctggcataac tacacaccag gccaggaat tagatacccc       120 gtaacctttg gatggtgctt caaactagta ccattgtcag ctgaagaagt agaagaggct      180
aatgaaggag acaacaatgc cctcttacac cccatatgtc aacatggagc agatgatgat      240
cataaagaag tgttggtgtg cgatttgac agctccctag caagaagaca tgtagcaaga      300
gagctgcatc cggagtttta caagaactgc tgacaaggga cttactgct gacaagggac      360 tttatacttg ggactttcc gccagggact ttccaggag gtgtggttgg gggagtggct      420
tgccctcaga gctgcataaa agcagccgct tctcgcttgt actgggtctc tcttgctgga      480
ctatacagat tagagcctgg gagctctctg gctagcaggg aacccactgc ttaagcctca      540
ataaatacag cttgccttga gtgctaaagt ggtgtgtgcc catccattcg gtaactctgg      600
tacctagaga tccctcaga ccatctagac tgagtgaaaa atctctagca gtggcgcccg      660
aacagggact tagttgaaaaa cgaaagtaga accggaggct gaatctctcg acgcaggact      720
cggctcgttg gtgcacacag cgagaggcga ggcggcggaa gtgtgagtac gcaattttga      780
ctggcggtgg ccagaaagta ggagagaggg agg                                   813

<210> SEQ ID NO 3
<211> LENGTH: 1539
<212> TYPE: DNA
<213> ORGANISM: Human immunodeficiency virus type 1
<220> FEATURE:
<221> NAME/KEY: CDS
<222> LOCATION: (1) (1536)

<400> SEQUENCE: 3 atg ggt gcg aga gcg tca gtg tta aca ggg gga aaa tta gat caa tgg        48
Met Gly Ala Arg Ala Ser Val Leu Thr Gly Gly Lys Leu Asp Gln Trp
  1               5                  10                  15 gaa tca att tat ttg aga cca ggg gga aag aaa aaa tac aga atg aaa        96
Glu Ser Ile Tyr Leu Arg Pro Gly Gly Lys Lys Lys Tyr Arg Met Lys
                 20                  25                  30 cat tta gta tgg gca agc agg gag ctg gaa aga ttc gct tgt aac cca       144
His Leu Val Trp Ala Ser Arg Glu Leu Glu Arg Phe Ala Cys Asn Pro
             35                  40                  45 ggt ctc atg gac aca gcg gac ggc tgt gcc aag tta cta aat caa tta       192
Gly Leu Met Asp Thr Ala Asp Gly Cys Ala Lys Leu Leu Asn Gln Leu
         50                  55                  60 gaa cca gct ctc aag aca ggg tca gaa gaa ctg cgc tct tta tat aac       240
Glu Pro Ala Leu Lys Thr Gly Ser Glu Glu Leu Arg Ser Leu Tyr Asn
 65                  70                  75                  80 gct cta gca gtt ctt tat tgt gtc cat agt agg ata cag ata cac aac       288
Ala Leu Ala Val Leu Tyr Cys Val His Ser Arg Ile Gln Ile His Asn
                 85                  90                  95 aca cag gaa gct ttg gac aag ata aaa gag aaa cag gaa cag cac aag       336
Thr Gln Glu Ala Leu Asp Lys Ile Lys Glu Lys Gln Glu Gln His Lys
                100                 105                 110
```

```
ccc gag cca aaa aac cca gaa gca ggg gca gcg gca act gat agc       384
Pro Glu Pro Lys Asn Pro Glu Ala Gly Ala Ala Ala Thr Asp Ser
        115                 120                 125 aat atc agt agg aat tat cct cta gtc cag act gct caa gga caa atg   432
Asn Ile Ser Arg Asn Tyr Pro Leu Val Gln Thr Ala Gln Gly Gln Met
130                 135                 140 gta cat cag ccg ctg aca ccc aga acc tta aat gct tgg gtg aaa gtg   480
Val His Gln Pro Leu Thr Pro Arg Thr Leu Asn Ala Trp Val Lys Val
145                 150                 155                 160 ata gag gag aag gcc ttt agt cca gaa gta ata cca atg ttt atg gcc   528
Ile Glu Glu Lys Ala Phe Ser Pro Glu Val Ile Pro Met Phe Met Ala
                165                 170                 175 ttg tca gaa ggg gca acg ccc tca gat cta aat act atg tta aat aca   576
Leu Ser Glu Gly Ala Thr Pro Ser Asp Leu Asn Thr Met Leu Asn Thr
            180                 185                 190 gta ggg gga cat cag gca gca atg cag atg ctg aag gaa gtc atc aat   624
Val Gly Gly His Gln Ala Ala Met Gln Met Leu Lys Glu Val Ile Asn
        195                 200                 205 gag gaa gca gca gac tgg gat agg aca cat cca gtc cct gtg gga cca   672
Glu Glu Ala Ala Asp Trp Asp Arg Thr His Pro Val Pro Val Gly Pro
210                 215                 220 cta ccc cca ggg caa ctg aga gac cct aga gga agt gat ata gca gga   720
Leu Pro Pro Gly Gln Leu Arg Asp Pro Arg Gly Ser Asp Ile Ala Gly
225                 230                 235                 240 aca act agc acc ctg gca gaa cag gtg gct tgg atg act gct aat cct   768
Thr Thr Ser Thr Leu Ala Glu Gln Val Ala Trp Met Thr Ala Asn Pro
                245                 250                 255 cct gtt cca gta gga gat att tat aga aga tgg ata gtc ctg ggg tta   816
Pro Val Pro Val Gly Asp Ile Tyr Arg Arg Trp Ile Val Leu Gly Leu
            260                 265                 270 aac aga att gtg aga atg tat agt cct gtc agc att cta gag atc aaa   864
Asn Arg Ile Val Arg Met Tyr Ser Pro Val Ser Ile Leu Glu Ile Lys
        275                 280                 285 caa gga cca aaa gaa ccc ttc aga gac tat gta gac agg ttc tac aaa   912
Gln Gly Pro Lys Glu Pro Phe Arg Asp Tyr Val Asp Arg Phe Tyr Lys
290                 295                 300 act cta aga gca gag cag gca aca cag gaa gta aag aat tgg atg aca   960
Thr Leu Arg Ala Glu Gln Ala Thr Gln Glu Val Lys Asn Trp Met Thr
305                 310                 315                 320 gaa aca ctc tta gta caa aat gca aac cca gat tgt aaa cag ctc cta  1008
Glu Thr Leu Leu Val Gln Asn Ala Asn Pro Asp Cys Lys Gln Leu Leu
                325                 330                 335 aaa gca tta ggg cca gga gct acc tta gaa gag atg atg acg gcc tgc  1056
Lys Ala Leu Gly Pro Gly Ala Thr Leu Glu Glu Met Met Thr Ala Cys
            340                 345                 350 cag gga gtg ggg gga cca gca cat aag gca aga gtg cta gca gag gct  1104
Gln Gly Val Gly Gly Pro Ala His Lys Ala Arg Val Leu Ala Glu Ala
        355                 360                 365 atg tca cag gtg cag cag cca aca act agt gtc ttt gca caa agg gga  1152
Met Ser Gln Val Gln Gln Pro Thr Thr Ser Val Phe Ala Gln Arg Gly
370                 375                 380 aac ttt aaa ggc ata agg aaa ccc att aaa tgt ttc aat tgt ggc aaa  1200
Asn Phe Lys Gly Ile Arg Lys Pro Ile Lys Cys Phe Asn Cys Gly Lys
385                 390                 395                 400 gag ggc cat ttg gca aga aac tgt aag gcc cct aga aga gga ggc tgt  1248
Glu Gly His Leu Ala Arg Asn Cys Lys Ala Pro Arg Arg Gly Gly Cys
                405                 410                 415 tgg aag tgt ggg caa gaa gga cat caa atg aaa gat tgt aaa aat gaa  1296
Trp Lys Cys Gly Gln Glu Gly His Gln Met Lys Asp Cys Lys Asn Glu
            420                 425                 430
```

```
gga aga cag gct aat ttt tta ggg aag agc tgg tct ccc ttc aaa ggg    1344
Gly Arg Gln Ala Asn Phe Leu Gly Lys Ser Trp Ser Pro Phe Lys Gly
            435                 440                 445 aga cca gga aac ttc ccc cag aca aca aca agg aaa gag ccc aca gcc    1392
Arg Pro Gly Asn Phe Pro Gln Thr Thr Thr Arg Lys Glu Pro Thr Ala
        450                 455                 460 ccg cca cta gag agt tat ggg ttt cag gag gag aag agc aca cag ggg    1440
Pro Pro Leu Glu Ser Tyr Gly Phe Gln Glu Glu Lys Ser Thr Gln Gly
465                 470                 475                 480 aag gag atg cag gag aac cag gag agg aca gag aac tct ctg tac cca    1488
Lys Glu Met Gln Glu Asn Gln Glu Arg Thr Glu Asn Ser Leu Tyr Pro
                485                 490                 495 cct tta act tcc ctc aga tca ctc ttt ggc aac gac ccg tca tca cag    1536
Pro Leu Thr Ser Leu Arg Ser Leu Phe Gly Asn Asp Pro Ser Ser Gln
            500                 505                 510 taa                                                                 1539

<210> SEQ ID NO 4
<211> LENGTH: 512
<212> TYPE: PRT
<213> ORGANISM: Human immunodeficiency virus type 1

<400> SEQUENCE: 4

Met Gly Ala Arg Ala Ser Val Leu Thr Gly Gly Lys Leu Asp Gln Trp
 1               5                  10                  15

Glu Ser Ile Tyr Leu Arg Pro Gly Gly Lys Lys Lys Tyr Arg Met Lys
            20                  25                  30

His Leu Val Trp Ala Ser Arg Glu Leu Glu Arg Phe Ala Cys Asn Pro
        35                  40                  45

Gly Leu Met Asp Thr Ala Asp Gly Cys Ala Lys Leu Leu Asn Gln Leu
    50                  55                  60

Glu Pro Ala Leu Lys Thr Gly Ser Glu Glu Leu Arg Ser Leu Tyr Asn
65                  70                  75                  80

Ala Leu Ala Val Leu Tyr Cys Val His Ser Arg Ile Gln Ile His Asn
                85                  90                  95

Thr Gln Glu Ala Leu Asp Lys Ile Lys Glu Lys Gln Glu Gln His Lys
            100                 105                 110

Pro Glu Pro Lys Asn Pro Glu Ala Gly Ala Ala Ala Thr Asp Ser
        115                 120                 125

Asn Ile Ser Arg Asn Tyr Pro Leu Val Gln Thr Ala Gln Gly Gln Met
    130                 135                 140

Val His Gln Pro Leu Thr Pro Arg Thr Leu Asn Ala Trp Val Lys Val
145                 150                 155                 160

Ile Glu Glu Lys Ala Phe Ser Pro Glu Val Ile Pro Met Phe Met Ala
                165                 170                 175

Leu Ser Glu Gly Ala Thr Pro Ser Asp Leu Asn Thr Met Leu Asn Thr
            180                 185                 190

Val Gly Gly His Gln Ala Ala Met Gln Met Leu Lys Glu Val Ile Asn
        195                 200                 205

Glu Glu Ala Ala Asp Trp Asp Arg Thr His Pro Val Pro Val Gly Pro
    210                 215                 220

Leu Pro Pro Gly Gln Leu Arg Asp Pro Arg Gly Ser Asp Ile Ala Gly
225                 230                 235                 240

Thr Thr Ser Thr Leu Ala Glu Gln Val Ala Trp Met Thr Ala Asn Pro
                245                 250                 255
```

```
Pro Val Pro Val Gly Asp Ile Tyr Arg Arg Trp Ile Val Leu Gly Leu
            260                 265                 270

Asn Arg Ile Val Arg Met Tyr Ser Pro Val Ser Ile Leu Glu Ile Lys
            275                 280                 285

Gln Gly Pro Lys Glu Pro Phe Arg Asp Tyr Val Asp Arg Phe Tyr Lys
            290                 295                 300

Thr Leu Arg Ala Glu Gln Ala Thr Gln Glu Val Lys Asn Trp Met Thr
305                 310                 315                 320

Glu Thr Leu Leu Val Gln Asn Ala Asn Pro Asp Cys Lys Gln Leu Leu
                325                 330                 335

Lys Ala Leu Gly Pro Gly Ala Thr Leu Glu Glu Met Met Thr Ala Cys
            340                 345                 350

Gln Gly Val Gly Gly Pro Ala His Lys Ala Arg Val Leu Ala Glu Ala
            355                 360                 365

Met Ser Gln Val Gln Gln Pro Thr Thr Ser Val Phe Ala Gln Arg Gly
            370                 375                 380

Asn Phe Lys Gly Ile Arg Lys Pro Ile Lys Cys Phe Asn Cys Gly Lys
385                 390                 395                 400

Glu Gly His Leu Ala Arg Asn Cys Lys Ala Pro Arg Arg Gly Gly Cys
                405                 410                 415

Trp Lys Cys Gly Gln Glu Gly His Gln Met Lys Asp Cys Lys Asn Glu
            420                 425                 430

Gly Arg Gln Ala Asn Phe Leu Gly Lys Ser Trp Ser Pro Phe Lys Gly
            435                 440                 445

Arg Pro Gly Asn Phe Pro Gln Thr Thr Thr Arg Lys Glu Pro Thr Ala
            450                 455                 460

Pro Pro Leu Glu Ser Tyr Gly Phe Gln Glu Lys Ser Thr Gln Gly
465                 470                 475                 480

Lys Glu Met Gln Glu Asn Gln Glu Arg Thr Glu Asn Ser Leu Tyr Pro
                485                 490                 495

Pro Leu Thr Ser Leu Arg Ser Leu Phe Gly Asn Asp Pro Ser Ser Gln
            500                 505                 510

<210> SEQ ID NO 5
<211> LENGTH: 3045
<212> TYPE: DNA
<213> ORGANISM: Human immunodeficiency virus type 1
<220> FEATURE:
<221> NAME/KEY: CDS
<222> LOCATION: (1)    (3042)

<400> SEQUENCE: 5 ttt ttt agg gaa gag ctg gtc tcc ctt caa agg gag acc agg aaa ctt     48
Phe Phe Arg Glu Glu Leu Val Ser Leu Gln Arg Glu Thr Arg Lys Leu
  1               5                  10                  15 ccc cca gac aac aac aag gaa aga gcc cac agc ccc gcc act aga gag     96
Pro Pro Asp Asn Asn Lys Glu Arg Ala His Ser Pro Ala Thr Arg Glu
             20                  25                  30 tta tgg gtt tca gga gga gaa gag cac aca ggg gaa gga gat gca gga    144
Leu Trp Val Ser Gly Gly Glu Glu His Thr Gly Glu Gly Asp Ala Gly
         35                  40                  45 gaa cca gga gag gac aga gaa ctc tct gta ccc acc ttt aac ttc cct    192
Glu Pro Gly Glu Asp Arg Glu Leu Ser Val Pro Thr Phe Asn Phe Pro
     50                  55                  60 cag atc act ctt tgg caa cga ccc gtc atc aca gta aaa ata ggg aaa    240
Gln Ile Thr Leu Trp Gln Arg Pro Val Ile Thr Val Lys Ile Gly Lys
 65                  70                  75                  80
```

-continued

| | | |
|---|---|---|
| gaa gta aga gaa gct ctt tta gat aca gga gct gat gat aca gta ata<br>Glu Val Arg Glu Ala Leu Leu Asp Thr Gly Ala Asp Asp Thr Val Ile<br>                 85                         90                       95 | 288 |
| gaa gag cta caa tta gag gga aaa tgg aaa cca aaa atg ata gga gga<br>Glu Glu Leu Gln Leu Glu Gly Lys Trp Lys Pro Lys Met Ile Gly Gly<br>                 100                      105                   110 | 336 |
| att gga gga ttt atc aaa gtg aga caa tat gat aat ata aca gta gac<br>Ile Gly Gly Phe Ile Lys Val Arg Gln Tyr Asp Asn Ile Thr Val Asp<br>                 115                      120                   125 | 384 |
| ata cag gga aga aaa gca gtt ggt aca gta tta gta gga cca aca cct<br>Ile Gln Gly Arg Lys Ala Val Gly Thr Val Leu Val Gly Pro Thr Pro<br>130                      135                   140 | 432 |
| gtt aat att ata gga aga aat ctt tta acc cag att ggc tgt act tta<br>Val Asn Ile Ile Gly Arg Asn Leu Leu Thr Gln Ile Gly Cys Thr Leu<br>145                      150                   155               160 | 480 |
| aat ttt cca ata agt cct att gaa act gta cca gta aaa tta aaa cca<br>Asn Phe Pro Ile Ser Pro Ile Glu Thr Val Pro Val Lys Leu Lys Pro<br>                 165                      170                   175 | 528 |
| gga atg gat ggc cca aag gta aaa caa tgg cct ttg aca aca gaa aaa<br>Gly Met Asp Gly Pro Lys Val Lys Gln Trp Pro Leu Thr Thr Glu Lys<br>                 180                      185                   190 | 576 |
| ata gag gca tta aga gaa att tgt aca gaa atg gaa aag gaa gga aaa<br>Ile Glu Ala Leu Arg Glu Ile Cys Thr Glu Met Glu Lys Glu Gly Lys<br>                 195                      200                   205 | 624 |
| att tct aga ata ggg cct gag aat cca tat aac act cca att ttt gct<br>Ile Ser Arg Ile Gly Pro Glu Asn Pro Tyr Asn Thr Pro Ile Phe Ala<br>                 210                      215                   220 | 672 |
| ata aaa aag aaa gat agc act aaa tgg aga aaa tta gta gat ttc agg<br>Ile Lys Lys Lys Asp Ser Thr Lys Trp Arg Lys Leu Val Asp Phe Arg<br>225                      230                   235               240 | 720 |
| gaa tta aat aaa agg acc caa gat ttt tgg gaa gtg cag cta gga att<br>Glu Leu Asn Lys Arg Thr Gln Asp Phe Trp Glu Val Gln Leu Gly Ile<br>                 245                      250                   255 | 768 |
| cca cat cca gca gga tta aag cag aaa aaa tca gta aca gtt tg gat<br>Pro His Pro Ala Gly Leu Lys Gln Lys Lys Ser Val Thr Val Leu Asp<br>                 260                      265                   270 | 816 |
| gta gga gat gct tat ttt tca tgt ccc ttg gac aaa gat ttt aga aag<br>Val Gly Asp Ala Tyr Phe Ser Cys Pro Leu Asp Lys Asp Phe Arg Lys<br>               275                      280                   285 | 864 |
| tat aca gct ttt acc ata cct agt ata aac aat gag aca cct ggt att<br>Tyr Thr Ala Phe Thr Ile Pro Ser Ile Asn Asn Glu Thr Pro Gly Ile<br>                 290                      295                   300 | 912 |
| aga tac cag tat aat gtg ctg cca caa ggc tgg aaa ggg tca cca gca<br>Arg Tyr Gln Tyr Asn Val Leu Pro Gln Gly Trp Lys Gly Ser Pro Ala<br>305                      310                   315               320 | 960 |
| att ttt cag agt aca atg aca aaa att cta gaa cca ttc aga gag aaa<br>Ile Phe Gln Ser Thr Met Thr Lys Ile Leu Glu Pro Phe Arg Glu Lys<br>                 325                      330                   335 | 1008 |
| cat cca gag ata atc att tac cag tac atg gat gac ctc tat gtg gga<br>His Pro Glu Ile Ile Ile Tyr Gln Tyr Met Asp Asp Leu Tyr Val Gly<br>                 340                      345                   350 | 1056 |
| tct gac tta gaa cta gca caa cat aga gag gca gta gaa gac ctc aga<br>Ser Asp Leu Glu Leu Ala Gln His Arg Glu Ala Val Glu Asp Leu Arg<br>                 355                      360                   365 | 1104 |
| gat cat ctt ttg aag tgg ggc ttt acg acc cct gac aaa aaa cat cag<br>Asp His Leu Leu Lys Trp Gly Phe Thr Thr Pro Asp Lys Lys His Gln<br>                 370                      375                   380 | 1152 |
| aag gag ccc ccg ttc ctc tgg atg gga tat gaa ctc cat cca gac aaa<br>Lys Glu Pro Pro Phe Leu Trp Met Gly Tyr Glu Leu His Pro Asp Lys<br>385                      390                   395               400 | 1200 |

```
tgg aca gtc cag cca ata aag tta cca gaa aag gat gta tgg act gtc      1248
Trp Thr Val Gln Pro Ile Lys Leu Pro Glu Lys Asp Val Trp Thr Val
            405                 410                 415 aat gat ata cag aaa tta gta gga aag tta aat tgg gca agt cag atc      1296
Asn Asp Ile Gln Lys Leu Val Gly Lys Leu Asn Trp Ala Ser Gln Ile
            420                 425                 430 tat cca gga atc aga gta aaa cag ctc tgt aaa tta atc aga gga gcc      1344
Tyr Pro Gly Ile Arg Val Lys Gln Leu Cys Lys Leu Ile Arg Gly Ala
            435                 440                 445 aga gct ttg aca gaa gta gtc aac ttt aca gaa gaa gca gaa tta gaa      1392
Arg Ala Leu Thr Glu Val Val Asn Phe Thr Glu Glu Ala Glu Leu Glu
450                 455                 460 cta gca gaa aac agg gag ata tta aaa gaa ccc ctg cat gga gtc tat      1440
Leu Ala Glu Asn Arg Glu Ile Leu Lys Glu Pro Leu His Gly Val Tyr
465                 470                 475                 480 tat gac cca gga aaa gaa tta gta gca gaa att caa aag caa gga caa      1488
Tyr Asp Pro Gly Lys Glu Leu Val Ala Glu Ile Gln Lys Gln Gly Gln
            485                 490                 495 ggt cag tgg aca tat cag att tat cag gag tta cat aaa aat tta aaa      1536
Gly Gln Trp Thr Tyr Gln Ile Tyr Gln Glu Leu His Lys Asn Leu Lys
            500                 505                 510 aca gga aag tat gca aaa atg aga tct gcc cat act aat gat ata aaa      1584
Thr Gly Lys Tyr Ala Lys Met Arg Ser Ala His Thr Asn Asp Ile Lys
            515                 520                 525 cag tta gtt gaa gtg gta agg aaa gtg gca aca gaa agt ata gta att      1632
Gln Leu Val Glu Val Val Arg Lys Val Ala Thr Glu Ser Ile Val Ile
530                 535                 540 tgg gga aag act cct aaa ttt aga tta cca gta caa aag gaa gtg tgg      1680
Trp Gly Lys Thr Pro Lys Phe Arg Leu Pro Val Gln Lys Glu Val Trp
545                 550                 555                 560 gag gca tgg tgg acc gat cat tgg caa gca act tgg att cct gag tgg      1728
Glu Ala Trp Trp Thr Asp His Trp Gln Ala Thr Trp Ile Pro Glu Trp
            565                 570                 575 gaa ttt gtc aac act cct ccc ctt gta aaa tta tgg tat cag tta gaa      1776
Glu Phe Val Asn Thr Pro Pro Leu Val Lys Leu Trp Tyr Gln Leu Glu
            580                 585                 590 aca gag cca atc agt ggg gca gaa act ttc tat gta gat gga gca gct      1824
Thr Glu Pro Ile Ser Gly Ala Glu Thr Phe Tyr Val Asp Gly Ala Ala
            595                 600                 605 aat agg gaa aca aaa ttg gga aaa gca ggt ttt gtg aca gat agg gga      1872
Asn Arg Glu Thr Lys Leu Gly Lys Ala Gly Phe Val Thr Asp Arg Gly
            610                 615                 620 aga cag aaa gtg gtc tct att gca gac acc acc aat caa aag gct gag      1920
Arg Gln Lys Val Val Ser Ile Ala Asp Thr Thr Asn Gln Lys Ala Glu
625                 630                 635                 640 tta caa gct atc ctt atg gcc tta caa gag tca gga cgg gat gta aac      1968
Leu Gln Ala Ile Leu Met Ala Leu Gln Glu Ser Gly Arg Asp Val Asn
            645                 650                 655 ata gtc act gac tct cag tat gct atg gga ata att cat tca cag cca      2016
Ile Val Thr Asp Ser Gln Tyr Ala Met Gly Ile Ile His Ser Gln Pro
            660                 665                 670 gat aaa agt gaa tca gaa ttg gtg agc caa ata ata gaa gag ctc ata      2064
Asp Lys Ser Glu Ser Glu Leu Val Ser Gln Ile Ile Glu Glu Leu Ile
            675                 680                 685 aaa aag gaa aga gtt tat ctc tct tgg gta cct gca cat aaa ggt att      2112
Lys Lys Glu Arg Val Tyr Leu Ser Trp Val Pro Ala His Lys Gly Ile
            690                 695                 700 gga gga aat gag cag gta gac aaa tta gtt agc tca gga att aga aaa      2160
Gly Gly Asn Glu Gln Val Asp Lys Leu Val Ser Ser Gly Ile Arg Lys
```

```
                705                 710                 715                 720
ata tta ttc cta gat ggt ata gaa aaa gcc caa gaa gat cat gac aga           2208
Ile Leu Phe Leu Asp Gly Ile Glu Lys Ala Gln Glu Asp His Asp Arg
                725                 730                 735 tat cac agc aat tgg aaa gca atg gcc agt gat ttt aac tta ccc ccc           2256
Tyr His Ser Asn Trp Lys Ala Met Ala Ser Asp Phe Asn Leu Pro Pro
                740                 745                 750 ata gtg gca aaa gaa ata gta gcc agc tgt gac aaa tgc cag cta aaa           2304
Ile Val Ala Lys Glu Ile Val Ala Ser Cys Asp Lys Cys Gln Leu Lys
                755                 760                 765 ggg gaa gcc atg cat gga cag gtc aat tgt agt cca gga gtg tgg caa           2352
Gly Glu Ala Met His Gly Gln Val Asn Cys Ser Pro Gly Val Trp Gln
770                 775                 780 tta gat tgt aca cac tta gag gga aaa atc atc ctt gtg gcg gtc cat           2400
Leu Asp Cys Thr His Leu Glu Gly Lys Ile Ile Leu Val Ala Val His
785                 790                 795                 800 gtg gcc agt ggc tac tta gaa gca gaa gtt att cct gca gag aca gga           2448
Val Ala Ser Gly Tyr Leu Glu Ala Glu Val Ile Pro Ala Glu Thr Gly
                805                 810                 815 cag gaa aca gca tat ttt att tta aag tta gct gga aga tgg cca gta           2496
Gln Glu Thr Ala Tyr Phe Ile Leu Lys Leu Ala Gly Arg Trp Pro Val
                820                 825                 830 aaa gtt ata cac act gat aat gga tcc aat ttc act agt gcc act gta           2544
Lys Val Ile His Thr Asp Asn Gly Ser Asn Phe Thr Ser Ala Thr Val
                835                 840                 845 aaa gca gcc tgt tgg tgg gca aat atc aaa cag gaa ttt ggg ata ccc           2592
Lys Ala Ala Cys Trp Trp Ala Asn Ile Lys Gln Glu Phe Gly Ile Pro
850                 855                 860 tac aat cct caa agt cag gga gca gta gag tcc atg aat aaa gaa tta           2640
Tyr Asn Pro Gln Ser Gln Gly Ala Val Glu Ser Met Asn Lys Glu Leu
865                 870                 875                 880 aag aaa att ata gga caa atc aga gat caa gca gaa cat cta aag aca           2688
Lys Lys Ile Ile Gly Gln Ile Arg Asp Gln Ala Glu His Leu Lys Thr
                885                 890                 895 gca gtg caa atg gcg gtt ttc att cac aat ttt aaa aga aaa ggg ggg           2736
Ala Val Gln Met Ala Val Phe Ile His Asn Phe Lys Arg Lys Gly Gly
                900                 905                 910 att ggg ggg tac act gca ggg gaa aga ata ata gac ata ata gca aca           2784
Ile Gly Gly Tyr Thr Ala Gly Glu Arg Ile Ile Asp Ile Ile Ala Thr
                915                 920                 925 gac ata cag aca aca aat tta caa aca caa att tta aaa gtt caa aat           2832
Asp Ile Gln Thr Thr Asn Leu Gln Thr Gln Ile Leu Lys Val Gln Asn
930                 935                 940 ttt cgg gtt tat tac aga gac agc aga gat ccc att tgg aaa gga cca           2880
Phe Arg Val Tyr Tyr Arg Asp Ser Arg Asp Pro Ile Trp Lys Gly Pro
945                 950                 955                 960 gcc aaa ctt ctg tgg aaa gga gaa ggg gca gtg gta att caa gat aac           2928
Ala Lys Leu Leu Trp Lys Gly Glu Gly Ala Val Val Ile Gln Asp Asn
                965                 970                 975 ggg gat ata aaa gta gtc cca cgt agg aaa gca aaa ata att agg gat           2976
Gly Asp Ile Lys Val Val Pro Arg Arg Lys Ala Lys Ile Ile Arg Asp
                980                 985                 990 tat gga aaa cag atg gca ggt gat ggt tgt gtg gca agt gga cag gat           3024
Tyr Gly Lys Gln Met Ala Gly Asp Gly Cys Val Ala Ser Gly Gln Asp
                995                 1000                1005 gaa aat cag gaa atg gaa tag                                               3045
Glu Asn Gln Glu Met Glu
          1010
```

```
<210> SEQ ID NO 6
<211> LENGTH: 1014
<212> TYPE: PRT
<213> ORGANISM: Human immunodeficiency virus type 1

<400> SEQUENCE: 6

Phe Phe Arg Glu Glu Leu Val Ser Leu Gln Arg Glu Thr Arg Lys Leu
  1               5                  10                  15

Pro Pro Asp Asn Asn Lys Glu Arg Ala His Ser Pro Ala Thr Arg Glu
             20                  25                  30

Leu Trp Val Ser Gly Gly Glu His Thr Gly Glu Gly Asp Ala Gly
         35                  40                  45

Glu Pro Gly Glu Asp Arg Glu Leu Ser Val Pro Thr Phe Asn Phe Pro
 50                  55                  60

Gln Ile Thr Leu Trp Gln Arg Pro Val Ile Thr Val Lys Ile Gly Lys
 65                  70                  75                  80

Glu Val Arg Glu Ala Leu Leu Asp Thr Gly Ala Asp Asp Thr Val Ile
                 85                  90                  95

Glu Glu Leu Gln Leu Glu Gly Lys Trp Lys Pro Lys Met Ile Gly Gly
            100                 105                 110

Ile Gly Gly Phe Ile Lys Val Arg Gln Tyr Asp Asn Ile Thr Val Asp
        115                 120                 125

Ile Gln Gly Arg Lys Ala Val Gly Thr Val Leu Val Gly Pro Thr Pro
    130                 135                 140

Val Asn Ile Ile Gly Arg Asn Leu Leu Thr Gln Ile Gly Cys Thr Leu
145                 150                 155                 160

Asn Phe Pro Ile Ser Pro Ile Glu Thr Val Pro Val Lys Leu Lys Pro
                165                 170                 175

Gly Met Asp Gly Pro Lys Val Lys Gln Trp Pro Leu Thr Thr Glu Lys
            180                 185                 190

Ile Glu Ala Leu Arg Glu Ile Cys Thr Glu Met Glu Lys Glu Gly Lys
        195                 200                 205

Ile Ser Arg Ile Gly Pro Glu Asn Pro Tyr Asn Thr Pro Ile Phe Ala
    210                 215                 220

Ile Lys Lys Lys Asp Ser Thr Lys Trp Arg Lys Leu Val Asp Phe Arg
225                 230                 235                 240

Glu Leu Asn Lys Arg Thr Gln Asp Phe Trp Glu Val Gln Leu Gly Ile
                245                 250                 255

Pro His Pro Ala Gly Leu Lys Gln Lys Lys Ser Val Thr Val Leu Asp
            260                 265                 270

Val Gly Asp Ala Tyr Phe Ser Cys Pro Leu Asp Lys Asp Phe Arg Lys
        275                 280                 285

Tyr Thr Ala Phe Thr Ile Pro Ser Ile Asn Asn Glu Thr Pro Gly Ile
    290                 295                 300

Arg Tyr Gln Tyr Asn Val Leu Pro Gln Gly Trp Lys Gly Ser Pro Ala
305                 310                 315                 320

Ile Phe Gln Ser Thr Met Thr Lys Ile Leu Glu Pro Phe Arg Glu Lys
                325                 330                 335

His Pro Glu Ile Ile Ile Tyr Gln Tyr Met Asp Asp Leu Tyr Val Gly
            340                 345                 350

Ser Asp Leu Glu Leu Ala Gln His Arg Glu Ala Val Gly Asp Leu Arg
        355                 360                 365

Asp His Leu Leu Lys Trp Gly Phe Thr Thr Pro Asp Lys Lys His Gln
    370                 375                 380
```

```
Lys Glu Pro Pro Phe Leu Trp Met Gly Tyr Glu Leu His Pro Asp Lys
385                 390                 395                 400

Trp Thr Val Gln Pro Ile Lys Leu Pro Glu Lys Asp Val Trp Thr Val
            405                 410                 415

Asn Asp Ile Gln Lys Leu Val Gly Lys Leu Asn Trp Ala Ser Gln Ile
            420                 425                 430

Tyr Pro Gly Ile Arg Val Lys Gln Leu Cys Lys Leu Ile Arg Gly Ala
            435                 440                 445

Arg Ala Leu Thr Glu Val Val Asn Phe Thr Glu Ala Glu Leu Glu
450                 455                 460

Leu Ala Glu Asn Arg Glu Ile Leu Lys Glu Pro Leu His Gly Val Tyr
465                 470                 475                 480

Tyr Asp Pro Gly Lys Glu Leu Val Ala Glu Ile Gln Lys Gln Gly Gln
            485                 490                 495

Gly Gln Trp Thr Tyr Gln Ile Tyr Gln Glu Leu His Lys Asn Leu Lys
            500                 505                 510

Thr Gly Lys Tyr Ala Lys Met Arg Ser Ala His Thr Asn Asp Ile Lys
            515                 520                 525

Gln Leu Val Glu Val Val Arg Lys Val Ala Thr Glu Ser Ile Val Ile
530                 535                 540

Trp Gly Lys Thr Pro Lys Phe Arg Leu Pro Val Gln Lys Glu Val Trp
545                 550                 555                 560

Glu Ala Trp Trp Thr Asp His Trp Gln Ala Thr Trp Ile Pro Glu Trp
                565                 570                 575

Glu Phe Val Asn Thr Pro Pro Leu Val Lys Leu Trp Tyr Gln Leu Glu
            580                 585                 590

Thr Glu Pro Ile Ser Gly Ala Glu Thr Phe Tyr Val Asp Gly Ala Ala
            595                 600                 605

Asn Arg Glu Thr Lys Leu Gly Lys Ala Gly Phe Val Thr Asp Arg Gly
            610                 615                 620

Arg Gln Lys Val Val Ser Ile Ala Asp Thr Thr Asn Gln Lys Ala Glu
625                 630                 635                 640

Leu Gln Ala Ile Leu Met Ala Leu Gln Glu Ser Gly Arg Asp Val Asn
                645                 650                 655

Ile Val Thr Asp Ser Gln Tyr Ala Met Gly Ile Ile His Ser Gln Pro
            660                 665                 670

Asp Lys Ser Glu Ser Glu Leu Val Ser Gln Ile Ile Glu Glu Leu Ile
            675                 680                 685

Lys Lys Glu Arg Val Tyr Leu Ser Trp Val Pro Ala His Lys Gly Ile
            690                 695                 700

Gly Gly Asn Glu Gln Val Asp Lys Leu Val Ser Ser Gly Ile Arg Lys
705                 710                 715                 720

Ile Leu Phe Leu Asp Gly Ile Glu Lys Ala Gln Glu Asp His Asp Arg
                725                 730                 735

Tyr His Ser Asn Trp Lys Ala Met Ala Ser Asp Phe Asn Leu Pro Pro
            740                 745                 750

Ile Val Ala Lys Glu Ile Val Ala Ser Cys Asp Lys Cys Gln Leu Lys
            755                 760                 765

Gly Glu Ala Met His Gly Gln Val Asn Cys Ser Pro Gly Val Trp Gln
            770                 775                 780

Leu Asp Cys Thr His Leu Glu Gly Lys Ile Ile Leu Val Ala Val His
785                 790                 795                 800

Val Ala Ser Gly Tyr Leu Glu Ala Glu Val Ile Pro Ala Glu Thr Gly
```

-continued

```
                    805                 810                 815
Gln Glu Thr Ala Tyr Phe Ile Leu Lys Leu Ala Gly Arg Trp Pro Val
            820                 825                 830

Lys Val Ile His Thr Asp Asn Gly Ser Asn Phe Thr Ser Ala Thr Val
            835                 840                 845

Lys Ala Ala Cys Trp Trp Ala Asn Ile Lys Gln Glu Phe Gly Ile Pro
            850                 855                 860

Tyr Asn Pro Gln Ser Gln Gly Ala Val Glu Ser Met Asn Lys Glu Leu
865                 870                 875                 880

Lys Lys Ile Ile Gly Gln Ile Arg Asp Gln Ala Glu His Leu Lys Thr
                885                 890                 895

Ala Val Gln Met Ala Val Phe Ile His Asn Phe Lys Arg Lys Gly Gly
            900                 905                 910

Ile Gly Gly Tyr Thr Ala Gly Glu Arg Ile Ile Asp Ile Ile Ala Thr
            915                 920                 925

Asp Ile Gln Thr Thr Asn Leu Gln Thr Gln Ile Leu Lys Val Gln Asn
            930                 935                 940

Phe Arg Val Tyr Tyr Arg Asp Ser Arg Asp Pro Ile Trp Lys Gly Pro
945                 950                 955                 960

Ala Lys Leu Leu Trp Lys Gly Glu Gly Ala Val Val Ile Gln Asp Asn
                965                 970                 975

Gly Asp Ile Lys Val Val Pro Arg Arg Lys Ala Lys Ile Ile Arg Asp
            980                 985                 990

Tyr Gly Lys Gln Met Ala Gly Asp Gly Cys Val Ala Ser Gly Gln Asp
            995                 1000                1005

Glu Asn Gln Glu Met Glu
    1010

<210> SEQ ID NO 7
<211> LENGTH: 579
<212> TYPE: DNA
<213> ORGANISM: Human immunodeficiency virus type 1
<220> FEATURE:
<221> NAME/KEY: CDS
<222> LOCATION: (1)    (576)

<400> SEQUENCE: 7 atg gaa aac aga tgg cag gtg atg gtt gtg tgg caa gtg gac agg atg      48
Met Glu Asn Arg Trp Gln Val Met Val Val Trp Gln Val Asp Arg Met
  1               5                  10                  15 aaa atc agg aaa tgg aat agc tta gta aaa cat cat atg tat gtg tca      96
Lys Ile Arg Lys Trp Asn Ser Leu Val Lys His His Met Tyr Val Ser
                20                  25                  30 aaa aag gca aaa gga tgg tat tat aga cat cat tat gaa aca cat cac     144
Lys Lys Ala Lys Gly Trp Tyr Tyr Arg His His Tyr Glu Thr His His
            35                  40                  45 cca aaa ata agt tca gaa gta cat atc cca gta ggt cag gca aga tta     192
Pro Lys Ile Ser Ser Glu Val His Ile Pro Val Gly Gln Ala Arg Leu
        50                  55                  60 gtg aca gtc act tat tgg ggg cta aca aca gga gaa cag tct tgg cat     240
Val Thr Val Thr Tyr Trp Gly Leu Thr Thr Gly Glu Gln Ser Trp His
 65                  70                  75                  80 cta gga cat gga gta tcc ata gaa tgg aga cta aga aaa tac aag aca     288
Leu Gly His Gly Val Ser Ile Glu Trp Arg Leu Arg Lys Tyr Lys Thr
                 85                  90                  95 caa gtt gat cct gaa atg gca gac aag cta ata cat ctt cat tat ttt     336
Gln Val Asp Pro Glu Met Ala Asp Lys Leu Ile His Leu His Tyr Phe
            100                 105                 110
```

-continued

```
gat tgt ttt aca gcc tct gcc ata agg caa gcg gtc tta ggg aga cca    384
Asp Cys Phe Thr Ala Ser Ala Ile Arg Gln Ala Val Leu Gly Arg Pro
        115                 120                 125 gta tta cct agg tgt gaa tat cca gca ggg cac aaa cag gta ggc acc    432
Val Leu Pro Arg Cys Glu Tyr Pro Ala Gly His Lys Gln Val Gly Thr
130                 135                 140 cta caa tat cta gca cta aca gcc tgg gtg gga gca aag aag aga aag    480
Leu Gln Tyr Leu Ala Leu Thr Ala Trp Val Gly Ala Lys Lys Arg Lys
145                 150                 155                 160 cca ccc tta cct agt gtg act aag cta aca gaa gat aga tgg aac gag    528
Pro Pro Leu Pro Ser Val Thr Lys Leu Thr Glu Asp Arg Trp Asn Glu
                165                 170                 175 cac cag aag atg cag ggc cac aga ggg aac cct ata atg aat ggg cac    576
His Gln Lys Met Gln Gly His Arg Gly Asn Pro Ile Met Asn Gly His
            180                 185                 190 tag                                                                579
```

<210> SEQ ID NO 8
<211> LENGTH: 192
<212> TYPE: PRT
<213> ORGANISM: Human immunodeficiency virus type 1

<400> SEQUENCE: 8

```
Met Glu Asn Arg Trp Gln Val Met Val Val Trp Gln Val Asp Arg Met
1               5                   10                  15

Lys Ile Arg Lys Trp Asn Ser Leu Val Lys His His Met Tyr Val Ser
            20                  25                  30

Lys Lys Ala Lys Gly Trp Tyr Tyr Arg His His Tyr Glu Thr His His
        35                  40                  45

Pro Lys Ile Ser Ser Glu Val His Ile Pro Val Gly Gln Ala Arg Leu
    50                  55                  60

Val Thr Val Thr Tyr Trp Gly Leu Thr Thr Gly Glu Gln Ser Trp His
65                  70                  75                  80

Leu Gly His Gly Val Ser Ile Glu Trp Arg Leu Arg Lys Tyr Lys Thr
                85                  90                  95

Gln Val Asp Pro Glu Met Ala Asp Lys Leu Ile His Leu His Tyr Phe
            100                 105                 110

Asp Cys Phe Thr Ala Ser Ala Ile Arg Gln Ala Val Leu Gly Arg Pro
        115                 120                 125

Val Leu Pro Arg Cys Glu Tyr Pro Ala Gly His Lys Gln Val Gly Thr
    130                 135                 140

Leu Gln Tyr Leu Ala Leu Thr Ala Trp Val Gly Ala Lys Lys Arg Lys
145                 150                 155                 160

Pro Pro Leu Pro Ser Val Thr Lys Leu Thr Glu Asp Arg Trp Asn Glu
                165                 170                 175

His Gln Lys Met Gln Gly His Arg Gly Asn Pro Ile Met Asn Gly His
            180                 185                 190
```

<210> SEQ ID NO 9
<211> LENGTH: 288
<212> TYPE: DNA
<213> ORGANISM: Human immunodeficiency virus type 1
<220> FEATURE:
<221> NAME/KEY: CDS
<222> LOCATION: (1)   (285)

<400> SEQUENCE: 9

```
atg gaa cga gca cca gaa gat gca ggg cca cag agg gaa ccc tat aat    48
```

```
Met Glu Arg Ala Pro Glu Asp Ala Gly Pro Gln Arg Glu Pro Tyr Asn
 1               5                  10                  15 gaa tgg gca cta gaa tta tta gaa gaa tta aaa aat gaa gct gtg cgc      96
Glu Trp Ala Leu Glu Leu Leu Glu Glu Leu Lys Asn Glu Ala Val Arg
             20                  25                  30 cat ttt cca agg att tgg cta cat ggg tta gga caa cac atc tat aac     144
His Phe Pro Arg Ile Trp Leu His Gly Leu Gly Gln His Ile Tyr Asn
         35                  40                  45 aca tat gga gac acc tgg gag ggg gta gag gca att atc agg ata cta     192
Thr Tyr Gly Asp Thr Trp Glu Gly Val Glu Ala Ile Ile Arg Ile Leu
     50                  55                  60 caa caa tta ctg ttt atc cat tat agg att ggc tgc cag cac agc aga     240
Gln Gln Leu Leu Phe Ile His Tyr Arg Ile Gly Cys Gln His Ser Arg
65                  70                  75                  80 ata ggg atc act cct caa agg aga agg aat gga acc agt aga tcc         285
Ile Gly Ile Thr Pro Gln Arg Arg Arg Asn Gly Thr Ser Arg Ser
                 85                  90                  95 tag                                                                 288

<210> SEQ ID NO 10
<211> LENGTH: 95
<212> TYPE: PRT
<213> ORGANISM: Human immunodeficiency virus type 1

<400> SEQUENCE: 10

Met Glu Arg Ala Pro Glu Asp Ala Gly Pro Gln Arg Glu Pro Tyr Asn
 1               5                  10                  15

Glu Trp Ala Leu Glu Leu Leu Glu Glu Leu Lys Asn Glu Ala Val Arg
             20                  25                  30

His Phe Pro Arg Ile Trp Leu His Gly Leu Gly Gln His Ile Tyr Asn
         35                  40                  45

Thr Tyr Gly Asp Thr Trp Glu Gly Val Glu Ala Ile Ile Arg Ile Leu
     50                  55                  60

Gln Gln Leu Leu Phe Ile His Tyr Arg Ile Gly Cys Gln His Ser Arg
65                  70                  75                  80

Ile Gly Ile Thr Pro Gln Arg Arg Arg Asn Gly Thr Ser Arg Ser
                 85                  90                  95

<210> SEQ ID NO 11
<211> LENGTH: 252
<212> TYPE: DNA
<213> ORGANISM: Human immunodeficiency virus type 1
<220> FEATURE:
<221> NAME/KEY: CDS
<222> LOCATION: (1)   (249)

<400> SEQUENCE: 11 atg ctg tca ttg gga ttc ata gcg tta gga gca gca gtt agc ata gca      48
Met Leu Ser Leu Gly Phe Ile Ala Leu Gly Ala Ala Val Ser Ile Ala
 1               5                  10                  15 gta ata gtc tgg gca tta cta tat aga gaa tat aag aaa ata aaa ttg      96
Val Ile Val Trp Ala Leu Leu Tyr Arg Glu Tyr Lys Lys Ile Lys Leu
             20                  25                  30 cag gaa aaa ata aaa cac ata aga cag aga ata aga gaa aga gaa         144
Gln Glu Lys Ile Lys His Ile Arg Gln Arg Ile Arg Glu Arg Glu Glu
         35                  40                  45 gat agt ggc aat gaa agt gat ggg gat gca gag tgg ttg gat ggg gat     192
Asp Ser Gly Asn Glu Ser Asp Gly Asp Ala Glu Trp Leu Asp Gly Asp
     50                  55                  60 gaa gag tgg ttg gtt act ctt cta tct tct agt aag ctt gat caa ggt     240
```

```
Glu Glu Trp Leu Val Thr Leu Leu Ser Ser Ser Lys Leu Asp Gln Gly
 65                  70                  75                  80 aat tgg gtc tga                                                          252
Asn Trp Val <210> SEQ ID NO 12
<211> LENGTH: 83
<212> TYPE: PRT
<213> ORGANISM: Human immunodeficiency virus type 1

<400> SEQUENCE: 12

Met Leu Ser Leu Gly Phe Ile Ala Leu Gly Ala Ala Val Ser Ile Ala
 1               5                  10                  15

Val Ile Val Trp Ala Leu Leu Tyr Arg Glu Tyr Lys Lys Ile Lys Leu
                20                  25                  30

Gln Glu Lys Ile Lys His Ile Arg Gln Arg Ile Arg Glu Arg Glu Glu
            35                  40                  45

Asp Ser Gly Asn Glu Ser Asp Gly Asp Ala Glu Trp Leu Asp Gly Asp
        50                  55                  60

Glu Glu Trp Leu Val Thr Leu Leu Ser Ser Ser Lys Leu Asp Gln Gly
 65                  70                  75                  80

Asn Trp Val

<210> SEQ ID NO 13
<211> LENGTH: 306
<212> TYPE: DNA
<213> ORGANISM: Human immunodeficiency virus type 1
<220> FEATURE:
<221> NAME/KEY: CDS
<222> LOCATION: (1)    (303)

<400> SEQUENCE: 13 atg gaa cca gta gat cct aga tta gag ccc tgg aat cat cca gga agc          48
Met Glu Pro Val Asp Pro Arg Leu Glu Pro Trp Asn His Pro Gly Ser
 1               5                  10                  15 caa cct aaa aca gct tgc aat aat tgc tat tgt aaa aga tgt tgc tat          96
Gln Pro Lys Thr Ala Cys Asn Asn Cys Tyr Cys Lys Arg Cys Cys Tyr
                20                  25                  30 cac tgc tta tat tgc ttc aca aag aaa ggc tta ggc atc tca tat ggc         144
His Cys Leu Tyr Cys Phe Thr Lys Lys Gly Leu Gly Ile Ser Tyr Gly
            35                  40                  45 agg aag aag cgg agt caa cga cga aga act cct cag agc agt aag agt         192
Arg Lys Lys Arg Ser Gln Arg Arg Arg Thr Pro Gln Ser Ser Lys Ser
        50                  55                  60 cat caa gat ctt ata cca gag cag ccc tta tcc caa cag caa ggg gac         240
His Gln Asp Leu Ile Pro Glu Gln Pro Leu Ser Gln Gln Gln Gly Asp
 65                  70                  75                  80 cag aca ggc cag aag aaa cag aag gag gcg ttg gag agc aag aca gag         288
Gln Thr Gly Gln Lys Lys Gln Lys Glu Ala Leu Glu Ser Lys Thr Glu
                85                  90                  95 gca gat ccg tgc gat tag                                                 306
Ala Asp Pro Cys Asp
            100

<210> SEQ ID NO 14
<211> LENGTH: 101
<212> TYPE: PRT
<213> ORGANISM: Human immunodeficiency virus type 1

<400> SEQUENCE: 14

Met Glu Pro Val Asp Pro Arg Leu Glu Pro Trp Asn His Pro Gly Ser
```

```
                1               5              10              15

Gln Pro Lys Thr Ala Cys Asn Asn Cys Tyr Cys Lys Arg Cys Cys Tyr
                                 20                  25                  30

His Cys Leu Tyr Cys Phe Thr Lys Lys Gly Leu Gly Ile Ser Tyr Gly
                             35                  40                  45

Arg Lys Lys Arg Ser Gln Arg Arg Thr Pro Gln Ser Ser Lys Ser
                         50                  55                  60

His Gln Asp Leu Ile Pro Glu Gln Pro Leu Ser Gln Gln Gln Gly Asp
               65                  70                  75                  80

Gln Thr Gly Gln Lys Lys Gln Lys Glu Ala Leu Glu Ser Lys Thr Glu
                             85                  90                  95

Ala Asp Pro Cys Asp
                            100

<210> SEQ ID NO 15
<211> LENGTH: 312
<212> TYPE: DNA
<213> ORGANISM: Human immunodeficiency virus type 1
<220> FEATURE:
<221> NAME/KEY: CDS
<222> LOCATION: (1)    (309)

<400> SEQUENCE: 15 atg gca gga aga agc gga gtc aac gac gaa gaa ctc ctc aga gca gta         48
Met Ala Gly Arg Ser Gly Val Asn Asp Glu Glu Leu Leu Arg Ala Val
 1               5                  10                  15 aga gtc atc aag atc tta tac cag agc agt tat ccc aac agc aag ggg         96
Arg Val Ile Lys Ile Leu Tyr Gln Ser Ser Tyr Pro Asn Ser Lys Gly
             20                  25                  30 acc aga cag gcc aga aga aac aga agg agg cgt tgg aga gca aga cag        144
Thr Arg Gln Ala Arg Arg Asn Arg Arg Arg Trp Arg Ala Arg Gln
         35                  40                  45 agg cag atc cgt gcg att agt gag cgg att ctc agc tct tgt ctg gga        192
Arg Gln Ile Arg Ala Ile Ser Glu Arg Ile Leu Ser Ser Cys Leu Gly
     50                  55                  60 gga cct ccg gaa cct gtt gat ctt cct cta cca ccg ctt gac aga ctc        240
Gly Pro Pro Glu Pro Val Asp Leu Pro Leu Pro Pro Leu Asp Arg Leu
 65                  70                  75                  80 act ctt gat act gag gag gac tct gga act cct ggg aca gag tct cag        288
Thr Leu Asp Thr Glu Glu Asp Ser Gly Thr Pro Gly Thr Glu Ser Gln
             85                  90                  95 cag ggg act gca act act gaa tga                                        312
Gln Gly Thr Ala Thr Thr Glu
            100

<210> SEQ ID NO 16
<211> LENGTH: 103
<212> TYPE: PRT
<213> ORGANISM: Human immunodeficiency virus type 1

<400> SEQUENCE: 16

Met Ala Gly Arg Ser Gly Val Asn Asp Glu Glu Leu Leu Arg Ala Val
 1               5                  10                  15

Arg Val Ile Lys Ile Leu Tyr Gln Ser Ser Tyr Pro Asn Ser Lys Gly
             20                  25                  30

Thr Arg Gln Ala Arg Arg Asn Arg Arg Arg Trp Arg Ala Arg Gln
         35                  40                  45

Arg Gln Ile Arg Ala Ile Ser Glu Arg Ile Leu Ser Ser Cys Leu Gly
     50                  55                  60
```

```
                        Gly Pro Pro Glu Pro Val Asp Leu Pro Leu Pro Pro Leu Asp Arg Leu
                         65                  70                  75                  80

Thr Leu Asp Thr Glu Glu Asp Ser Gly Thr Pro Gly Thr Glu Ser Gln
                                         85                  90                  95

Gln Gly Thr Ala Thr Thr Glu
                                    100

<210> SEQ ID NO 17
<211> LENGTH: 2559
<212> TYPE: DNA
<213> ORGANISM: Human immunodeficiency virus type 1
<220> FEATURE:
<221> NAME/KEY: CDS
<222> LOCATION: (1)    (2556)

<400> SEQUENCE: 17 atg aaa gtg atg ggg atg cag agt ggt tgg atg ggg atg aag agt ggt          48
Met Lys Val Met Gly Met Gln Ser Gly Trp Met Gly Met Lys Ser Gly
  1               5                  10                  15 tgg tta ctc ttc tat ctt cta gta agc ttg atc aag gta att ggg tct          96
Trp Leu Leu Phe Tyr Leu Leu Val Ser Leu Ile Lys Val Ile Gly Ser
                 20                  25                  30 gaa caa cat tgg gta aca gtg tac tat ggg gta cca gta tgg aga gaa         144
Glu Gln His Trp Val Thr Val Tyr Tyr Gly Val Pro Val Trp Arg Glu
             35                  40                  45 gca gag aca act ctt ttc tgt gct tca gat gct aaa gcc cat agt aca         192
Ala Glu Thr Thr Leu Phe Cys Ala Ser Asp Ala Lys Ala His Ser Thr
         50                  55                  60 gag gct cac aac atc tgg gcc aca caa gca tgt gtt cct act gat ccc         240
Glu Ala His Asn Ile Trp Ala Thr Gln Ala Cys Val Pro Thr Asp Pro
 65                  70                  75                  80 aat cca caa gaa gtg cta tta ccc aat gta act gaa aaa ttt aat atg         288
Asn Pro Gln Glu Val Leu Leu Pro Asn Val Thr Glu Lys Phe Asn Met
                 85                  90                  95 tgg gaa aat aaa atg gca gac caa atg caa gag gat att atc agt ctg         336
Trp Glu Asn Lys Met Ala Asp Gln Met Gln Glu Asp Ile Ile Ser Leu
                100                 105                 110 tgg gaa cag agc tta aag ccc tgt gtt aaa tta acc cca tta tgt gta         384
Trp Glu Gln Ser Leu Lys Pro Cys Val Lys Leu Thr Pro Leu Cys Val
            115                 120                 125 act atg ctt tgt aac gat agc tat ggg gag gaa agg aac aat aca aat         432
Thr Met Leu Cys Asn Asp Ser Tyr Gly Glu Glu Arg Asn Asn Thr Asn
        130                 135                 140 atg aca aca aga gaa cca gac ata gga tac aaa caa atg aaa aat tgc         480
Met Thr Thr Arg Glu Pro Asp Ile Gly Tyr Lys Gln Met Lys Asn Cys
145                 150                 155                 160 tca ttc aat gca acc act gag cta aca gat aaa aag aag caa gtt tac         528
Ser Phe Asn Ala Thr Thr Glu Leu Thr Asp Lys Lys Lys Gln Val Tyr
                165                 170                 175 tct ctg ttt tat gta gaa gat gta gta cca atc aat gcc tat aat aaa         576
Ser Leu Phe Tyr Val Glu Asp Val Val Pro Ile Asn Ala Tyr Asn Lys
            180                 185                 190 aca tat agg cta ata aat tgt aat acc aca gct gtg aca caa gct tgt         624
Thr Tyr Arg Leu Ile Asn Cys Asn Thr Thr Ala Val Thr Gln Ala Cys
        195                 200                 205 cct aag act tcc ttt gag cca att cca ata cat tac tgt gca cca cca         672
Pro Lys Thr Ser Phe Glu Pro Ile Pro Ile His Tyr Cys Ala Pro Pro
    210                 215                 220 ggc ttt gcc att atg aaa tgt aat gaa gga aac ttt agt gga aat gga         720
Gly Phe Ala Ile Met Lys Cys Asn Glu Gly Asn Phe Ser Gly Asn Gly
225                 230                 235                 240
```

-continued

| | |
|---|---|
| agc tgt aca aat gtg agt act gta caa tgc aca cat gga ata aag cca<br>Ser Cys Thr Asn Val Ser Thr Val Gln Cys Thr His Gly Ile Lys Pro<br>                       245                       250                       255 | 768 |
| gtg ata tcc act cag tta atc cta aat gga agc tta aat aca gat gga<br>Val Ile Ser Thr Gln Leu Ile Leu Asn Gly Ser Leu Asn Thr Asp Gly<br>260                       265                     270 | 816 |
| att gtt att aga aat gat agt cac agt aat ctg ttg gtg caa tgg aat<br>Ile Val Ile Arg Asn Asp Ser His Ser Asn Leu Leu Val Gln Trp Asn<br>         275                     280                     285 | 864 |
| gag aca gtg cca ata aat tgt aca agg cca gga aat aat aca gga gga<br>Glu Thr Val Pro Ile Asn Cys Thr Arg Pro Gly Asn Asn Thr Gly Gly<br>290                       295                     300 | 912 |
| cag gtg cag ata gga cct gct atg aca ttt tat aac ata gaa aaa ata<br>Gln Val Gln Ile Gly Pro Ala Met Thr Phe Tyr Asn Ile Glu Lys Ile<br>305                     310                   315                 320 | 960 |
| gta gga gac att aga caa gca tac tgt aat gtc tct aaa gaa cta tgg<br>Val Gly Asp Ile Arg Gln Ala Tyr Cys Asn Val Ser Lys Glu Leu Trp<br>         325                     330                     335 | 1008 |
| gaa cca atg tgg aat aga aca aga gag gaa ata aag aaa atc ctg ggg<br>Glu Pro Met Trp Asn Arg Thr Arg Glu Glu Ile Lys Lys Ile Leu Gly<br>               340                     345                     350 | 1056 |
| aaa aac aac ata acc ttc agg gct cga gag agg aat gaa gga gac cta<br>Lys Asn Asn Ile Thr Phe Arg Ala Arg Glu Arg Asn Glu Gly Asp Leu<br>                   355                     360                   365 | 1104 |
| gaa gtg aca cac tta atg ttc aat tgt aga gga gag ttt ttc tat tgt<br>Glu Val Thr His Leu Met Phe Asn Cys Arg Gly Glu Phe Phe Tyr Cys<br>370                       375                     380 | 1152 |
| aac act tcc aaa tta ttt aat gag gaa tta ctt aac gag aca ggt gag<br>Asn Thr Ser Lys Leu Phe Asn Glu Glu Leu Leu Asn Glu Thr Gly Glu<br>385                     390                     395                 400 | 1200 |
| cct att act ctg cct tgt aga ata aga cag att gta aat ttg tgg aca<br>Pro Ile Thr Leu Pro Cys Arg Ile Arg Gln Ile Val Asn Leu Trp Thr<br>                   405                     410                   415 | 1248 |
| agg gta gga aaa gga att tat gca cca cca att cgg gga gtt ctt aac<br>Arg Val Gly Lys Gly Ile Tyr Ala Pro Pro Ile Arg Gly Val Leu Asn<br>420                       425                     430 | 1296 |
| tgt acc tcc aat att act gga ctg gtt cta gaa tat agt ggt ggg cct<br>Cys Thr Ser Asn Ile Thr Gly Leu Val Leu Glu Tyr Ser Gly Gly Pro<br>         435                     440                     445 | 1344 |
| gac acc aag gaa aca ata gta tat ccc tca gga gga aac atg gtt aat<br>Asp Thr Lys Glu Thr Ile Val Tyr Pro Ser Gly Gly Asn Met Val Asn<br>450                       455                     460 | 1392 |
| ctc tgg aga caa gag ttg tat aag tac aaa gta gtt agc ata gaa ccc<br>Leu Trp Arg Gln Glu Leu Tyr Lys Tyr Lys Val Val Ser Ile Glu Pro<br>465                     470                     475                 480 | 1440 |
| ata gga gta gca cca ggt aaa gct aaa aga cgc aca gtg agt aga gaa<br>Ile Gly Val Ala Pro Gly Lys Ala Lys Arg Arg Thr Val Ser Arg Glu<br>               485                     490                   495 | 1488 |
| aaa aga gca gcc ttt gga cta ggt gcg ctg ttt ctt ggg ttt ctt gga<br>Lys Arg Ala Ala Phe Gly Leu Gly Ala Leu Phe Leu Gly Phe Leu Gly<br>               500                     505                   510 | 1536 |
| gca gca ggg agc act atg ggc gca gcg tca ata acg ctg acg gta cag<br>Ala Ala Gly Ser Thr Met Gly Ala Ala Ser Ile Thr Leu Thr Val Gln<br>         515                     520                     525 | 1584 |
| gcc cgg aca tta tta tct ggg ata gtg caa cag cag aat att ctg ttg<br>Ala Arg Thr Leu Leu Ser Gly Ile Val Gln Gln Gln Asn Ile Leu Leu<br>530                       535                     540 | 1632 |
| aga gca ata gag gcg caa caa cat ttg ttg caa ctc tca atc tgg ggc<br>Arg Ala Ile Glu Ala Gln Gln His Leu Leu Gln Leu Ser Ile Trp Gly | 1680 |

-continued

```
             545                 550                 555                 560
att aaa cag ctc cag gca aaa gtc ctt gct ata gaa aga tac ctt agg         1728
Ile Lys Gln Leu Gln Ala Lys Val Leu Ala Ile Glu Arg Tyr Leu Arg
             565                 570                 575 gat cag caa atc cta agt cta tgg ggc tgc tca gga aaa aca ata tgc         1776
Asp Gln Gln Ile Leu Ser Leu Trp Gly Cys Ser Gly Lys Thr Ile Cys
             580                 585                 590 tat acc act gtg cct tgg aat gag act tgg agc aac aat acc tct tat         1824
Tyr Thr Thr Val Pro Trp Asn Glu Thr Trp Ser Asn Asn Thr Ser Tyr
             595                 600                 605 gat aca atc tgg aat aat tta acc tgg caa caa tgg gat gag aaa gta         1872
Asp Thr Ile Trp Asn Asn Leu Thr Trp Gln Gln Trp Asp Glu Lys Val
             610                 615                 620 aga aac tat tca ggt gtc att ttt gga ctt ata gaa cag gca caa gaa         1920
Arg Asn Tyr Ser Gly Val Ile Phe Gly Leu Ile Glu Gln Ala Gln Glu
625                 630                 635                 640 caa cag aac aca aat gag aaa tca ctc ttg gaa ttg gat caa tgg gac         1968
Gln Gln Asn Thr Asn Glu Lys Ser Leu Leu Glu Leu Asp Gln Trp Asp
                 645                 650                 655 agt ctg tgg agc tgg ttt ggt att aca aaa tgg ctg tgg tat ata aaa         2016
Ser Leu Trp Ser Trp Phe Gly Ile Thr Lys Trp Leu Trp Tyr Ile Lys
             660                 665                 670 ata gct ata atg ata gta gca ggc att gta ggc ata aga atc ata agt         2064
Ile Ala Ile Met Ile Val Ala Gly Ile Val Gly Ile Arg Ile Ile Ser
             675                 680                 685 ata gta ata act ata ata gca aga gtt agg cag gga tat tct ccc ctt         2112
Ile Val Ile Thr Ile Ile Ala Arg Val Arg Gln Gly Tyr Ser Pro Leu
             690                 695                 700 tcg ttg cag acc ctt atc cca aca gca agg gga cca gac agg cca gaa         2160
Ser Leu Gln Thr Leu Ile Pro Thr Ala Arg Gly Pro Asp Arg Pro Glu
705                 710                 715                 720 gaa aca gaa gga ggc gtt gga gag caa gac aga ggc aga tcc gtg cga         2208
Glu Thr Glu Gly Gly Val Gly Glu Gln Asp Arg Gly Arg Ser Val Arg
                 725                 730                 735 tta gtg agc gga ttc tca gct ctt gtc tgg gag gac ctc cgg aac ctg         2256
Leu Val Ser Gly Phe Ser Ala Leu Val Trp Glu Asp Leu Arg Asn Leu
             740                 745                 750 ttg atc ttc ctc tac cac cgc ttg aca gac tca ctc ttg ata ctg agg         2304
Leu Ile Phe Leu Tyr His Arg Leu Thr Asp Ser Leu Leu Ile Leu Arg
             755                 760                 765 agg act ctg gaa ctc ctg gga cag agt ctc agc agg gga ctg caa cta         2352
Arg Thr Leu Glu Leu Leu Gly Gln Ser Leu Ser Arg Gly Leu Gln Leu
770                 775                 780 ctg aat gaa ctc aga aca cac ttg tgg gga ata ctt gca tat tgg gga         2400
Leu Asn Glu Leu Arg Thr His Leu Trp Gly Ile Leu Ala Tyr Trp Gly
785                 790                 795                 800 aaa gag tta agg gat agt gct atc agc ttg ctt aat aca aca gct att         2448
Lys Glu Leu Arg Asp Ser Ala Ile Ser Leu Leu Asn Thr Thr Ala Ile
                 805                 810                 815 gta gta gca gaa gga aca gat agg att ata gaa tta gca caa aga ata         2496
Val Val Ala Glu Gly Thr Asp Arg Ile Ile Glu Leu Ala Gln Arg Ile
             820                 825                 830 gga agg gga ata tta cac ata cct aga aga atc aga caa ggc cta gaa         2544
Gly Arg Gly Ile Leu His Ile Pro Arg Arg Ile Arg Gln Gly Leu Glu
             835                 840                 845 aga gca ctg ata taa                                                     2559
Arg Ala Leu Ile
850
```

<210> SEQ ID NO 18
<211> LENGTH: 852
<212> TYPE: PRT
<213> ORGANISM: Human immunodeficiency virus type 1

<400> SEQUENCE: 18

```
Met Lys Val Met Gly Met Gln Ser Gly Trp Met Gly Met Lys Ser Gly
 1               5                  10                  15
Trp Leu Leu Phe Tyr Leu Leu Val Ser Leu Ile Lys Val Ile Gly Ser
             20                  25                  30
Glu Gln His Trp Val Thr Val Tyr Tyr Gly Val Pro Val Trp Arg Glu
         35                  40                  45
Ala Glu Thr Thr Leu Phe Cys Ala Ser Asp Ala Lys Ala His Ser Thr
     50                  55                  60
Glu Ala His Asn Ile Trp Ala Thr Gln Ala Cys Val Pro Thr Asp Pro
 65                  70                  75                  80
Asn Pro Gln Glu Val Leu Leu Pro Asn Val Thr Glu Lys Phe Asn Met
                 85                  90                  95
Trp Glu Asn Lys Met Ala Asp Gln Met Gln Glu Asp Ile Ile Ser Leu
            100                 105                 110
Trp Glu Gln Ser Leu Lys Pro Cys Val Lys Leu Thr Pro Leu Cys Val
        115                 120                 125
Thr Met Leu Cys Asn Asp Ser Tyr Gly Glu Glu Arg Asn Asn Thr Asn
    130                 135                 140
Met Thr Thr Arg Glu Pro Asp Ile Gly Tyr Lys Gln Met Lys Asn Cys
145                 150                 155                 160
Ser Phe Asn Ala Thr Thr Glu Leu Thr Asp Lys Lys Gln Val Tyr
                165                 170                 175
Ser Leu Phe Tyr Val Glu Asp Val Val Pro Ile Asn Ala Tyr Asn Lys
            180                 185                 190
Thr Tyr Arg Leu Ile Asn Cys Asn Thr Thr Ala Val Thr Gln Ala Cys
        195                 200                 205
Pro Lys Thr Ser Phe Glu Pro Ile Pro Ile His Tyr Cys Ala Pro Pro
    210                 215                 220
Gly Phe Ala Ile Met Lys Cys Asn Glu Gly Asn Phe Ser Gly Asn Gly
225                 230                 235                 240
Ser Cys Thr Asn Val Ser Thr Val Gln Cys Thr His Gly Ile Lys Pro
                245                 250                 255
Val Ile Ser Thr Gln Leu Ile Leu Asn Gly Ser Leu Asn Thr Asp Gly
            260                 265                 270
Ile Val Ile Arg Asn Asp Ser His Ser Asn Leu Leu Val Gln Trp Asn
        275                 280                 285
Glu Thr Val Pro Ile Asn Cys Thr Arg Pro Gly Asn Asn Thr Gly Gly
    290                 295                 300
Gln Val Gln Ile Gly Pro Ala Met Thr Phe Tyr Asn Ile Glu Lys Ile
305                 310                 315                 320
Val Gly Asp Ile Arg Gln Ala Tyr Cys Asn Val Ser Lys Glu Leu Trp
                325                 330                 335
Glu Pro Met Trp Asn Arg Thr Arg Glu Glu Ile Lys Lys Ile Leu Gly
            340                 345                 350
Lys Asn Asn Ile Thr Phe Arg Ala Arg Glu Arg Asn Glu Gly Asp Leu
        355                 360                 365
Glu Val Thr His Leu Met Phe Asn Cys Arg Gly Glu Phe Phe Tyr Cys
    370                 375                 380
```

```
Asn Thr Ser Lys Leu Phe Asn Glu Glu Leu Leu Asn Glu Thr Gly Glu
385                 390                 395                 400

Pro Ile Thr Leu Pro Cys Arg Ile Arg Gln Ile Val Asn Leu Trp Thr
            405                 410                 415

Arg Val Gly Lys Gly Ile Tyr Ala Pro Pro Ile Arg Gly Val Leu Asn
            420                 425                 430

Cys Thr Ser Asn Ile Thr Gly Leu Val Leu Glu Tyr Ser Gly Gly Pro
            435                 440                 445

Asp Thr Lys Glu Thr Ile Val Tyr Pro Ser Gly Gly Asn Met Val Asn
            450                 455                 460

Leu Trp Arg Gln Glu Leu Tyr Lys Tyr Lys Val Val Ser Ile Glu Pro
465                 470                 475                 480

Ile Gly Val Ala Pro Gly Lys Ala Lys Arg Arg Thr Val Ser Arg Glu
            485                 490                 495

Lys Arg Ala Ala Phe Gly Leu Gly Ala Leu Phe Leu Gly Phe Leu Gly
            500                 505                 510

Ala Ala Gly Ser Thr Met Gly Ala Ala Ser Ile Thr Leu Thr Val Gln
            515                 520                 525

Ala Arg Thr Leu Leu Ser Gly Ile Val Gln Gln Gln Asn Ile Leu Leu
            530                 535                 540

Arg Ala Ile Glu Ala Gln Gln His Leu Leu Gln Leu Ser Ile Trp Gly
545                 550                 555                 560

Ile Lys Gln Leu Gln Ala Lys Val Leu Ala Ile Glu Arg Tyr Leu Arg
            565                 570                 575

Asp Gln Gln Ile Leu Ser Leu Trp Gly Cys Ser Gly Lys Thr Ile Cys
            580                 585                 590

Tyr Thr Thr Val Pro Trp Asn Glu Thr Trp Ser Asn Asn Thr Ser Tyr
            595                 600                 605

Asp Thr Ile Trp Asn Asn Leu Thr Trp Gln Gln Trp Asp Glu Lys Val
            610                 615                 620

Arg Asn Tyr Ser Gly Val Ile Phe Gly Leu Ile Glu Gln Ala Gln Glu
625                 630                 635                 640

Gln Gln Asn Thr Asn Glu Lys Ser Leu Leu Glu Leu Asp Gln Trp Asp
            645                 650                 655

Ser Leu Trp Ser Trp Phe Gly Ile Thr Lys Trp Leu Trp Tyr Ile Lys
            660                 665                 670

Ile Ala Ile Met Ile Val Ala Gly Ile Val Gly Ile Arg Ile Ile Ser
            675                 680                 685

Ile Val Ile Thr Ile Ile Ala Arg Val Arg Gln Gly Tyr Ser Pro Leu
            690                 695                 700

Ser Leu Gln Thr Leu Ile Pro Thr Ala Arg Gly Pro Asp Arg Pro Glu
705                 710                 715                 720

Glu Thr Glu Gly Gly Val Gly Glu Gln Asp Arg Gly Arg Ser Val Arg
            725                 730                 735

Leu Val Ser Gly Phe Ser Ala Leu Val Trp Glu Asp Leu Arg Asn Leu
            740                 745                 750

Leu Ile Phe Leu Tyr His Arg Leu Thr Asp Ser Leu Leu Ile Leu Arg
            755                 760                 765

Arg Thr Leu Glu Leu Leu Gly Gln Ser Leu Ser Arg Gly Leu Gln Leu
            770                 775                 780

Leu Asn Glu Leu Arg Thr His Leu Trp Gly Ile Leu Ala Tyr Trp Gly
785                 790                 795                 800

Lys Glu Leu Arg Asp Ser Ala Ile Ser Leu Leu Asn Thr Thr Ala Ile
```

-continued

```
                     805                 810                 815
             Val Val Ala Glu Gly Thr Asp Arg Ile Ile Glu Leu Ala Gln Arg Ile
                             820                 825                 830

Gly Arg Gly Ile Leu His Ile Pro Arg Arg Ile Arg Gln Gly Leu Glu
                         835                 840                 845

Arg Ala Leu Ile
                     850

<210> SEQ ID NO 19
<211> LENGTH: 639
<212> TYPE: DNA
<213> ORGANISM: Human immunodeficiency virus type 1
<220> FEATURE:
<221> NAME/KEY: CDS
<222> LOCATION: (1)     (636)

<400> SEQUENCE: 19 atg gga aag att tgg tca aag agc agc cta gta gga tgg cca gaa atc        48
Met Gly Lys Ile Trp Ser Lys Ser Ser Leu Val Gly Trp Pro Glu Ile
  1               5                  10                  15 aga gaa aga atg aga aga caa acg caa gaa cca gca gta gag cca gca        96
Arg Glu Arg Met Arg Arg Gln Thr Gln Glu Pro Ala Val Glu Pro Ala
                 20                  25                  30 gta gga gca gga gca gct tct caa gat cta gct aat cga ggg gcc atc       144
Val Gly Ala Gly Ala Ala Ser Gln Asp Leu Ala Asn Arg Gly Ala Ile
             35                  40                  45 acc ata aga aat act aga gac aat aat gaa agt ata gct tgg cta gaa       192
Thr Ile Arg Asn Thr Arg Asp Asn Asn Glu Ser Ile Ala Trp Leu Glu
         50                  55                  60 gca caa gaa gaa gaa gag gaa gta ggc ttt cca gta cgc cct cag gta       240
Ala Gln Glu Glu Glu Glu Glu Val Gly Phe Pro Val Arg Pro Gln Val
 65                  70                  75                  80 cca tta agg cca ata acc tat aaa cag gct ttt gat ctt tcc ttc ttt       288
Pro Leu Arg Pro Ile Thr Tyr Lys Gln Ala Phe Asp Leu Ser Phe Phe
                 85                  90                  95 tta aaa gat aag ggg gga ctg gaa ggg cta gtt tgg tcc aga aaa agg       336
Leu Lys Asp Lys Gly Gly Leu Glu Gly Leu Val Trp Ser Arg Lys Arg
            100                 105                 110 caa gat att cta gac ctc tgg atg tat cac aca caa ggc atc ctc cct       384
Gln Asp Ile Leu Asp Leu Trp Met Tyr His Thr Gln Gly Ile Leu Pro
        115                 120                 125 gac tgg cat aac tac aca cca ggg cca gga att aga tac ccc gta acc       432
Asp Trp His Asn Tyr Thr Pro Gly Pro Gly Ile Arg Tyr Pro Val Thr
    130                 135                 140 ttt gga tgg tgc ttc aaa cta gta cca ttg tca gct gaa gaa gta gaa       480
Phe Gly Trp Cys Phe Lys Leu Val Pro Leu Ser Ala Glu Glu Val Glu
145                 150                 155                 160 gag gct aat gaa gga gac aac aat gcc ctc tta cac ccc ata tgt caa       528
Glu Ala Asn Glu Gly Asp Asn Asn Ala Leu Leu His Pro Ile Cys Gln
                165                 170                 175 cat gga gca gat gat gat cat aaa gaa gtg ttg gtg tgg cga ttt gac       576
His Gly Ala Asp Asp Asp His Lys Glu Val Leu Val Trp Arg Phe Asp
            180                 185                 190 agc tcc cta gca aga aga cat gta gca aga gag ctg cat ccg gag ttt       624
Ser Ser Leu Ala Arg Arg His Val Ala Arg Glu Leu His Pro Glu Phe
        195                 200                 205 tac aag aac tgc tga                                                   639
Tyr Lys Asn Cys
    210
```

```
<210> SEQ ID NO 20
<211> LENGTH: 212
<212> TYPE: PRT
<213> ORGANISM: Human immunodeficiency virus type 1

<400> SEQUENCE: 20

Met Gly Lys Ile Trp Ser Lys Ser Ser Leu Val Gly Trp Pro Glu Ile
 1               5                  10                  15

Arg Glu Arg Met Arg Arg Gln Thr Gln Glu Pro Ala Val Glu Pro Ala
                20                  25                  30

Val Gly Ala Gly Ala Ala Ser Gln Asp Leu Ala Asn Arg Gly Ala Ile
            35                  40                  45

Thr Ile Arg Asn Thr Arg Asp Asn Asn Glu Ser Ile Ala Trp Leu Glu
 50                  55                  60

Ala Gln Glu Glu Glu Glu Val Gly Phe Pro Val Arg Pro Gln Val
 65                  70                  75                  80

Pro Leu Arg Pro Ile Thr Tyr Lys Gln Ala Phe Asp Leu Ser Phe Phe
                85                  90                  95

Leu Lys Asp Lys Gly Gly Leu Glu Gly Leu Val Trp Ser Arg Lys Arg
            100                 105                 110

Gln Asp Ile Leu Asp Leu Trp Met Tyr His Thr Gln Gly Ile Leu Pro
        115                 120                 125

Asp Trp His Asn Tyr Thr Pro Gly Pro Gly Ile Arg Tyr Pro Val Thr
130                 135                 140

Phe Gly Trp Cys Phe Lys Leu Val Pro Leu Ser Ala Glu Val Glu
145                 150                 155                 160

Glu Ala Asn Glu Gly Asp Asn Asn Ala Leu Leu His Pro Ile Cys Gln
                165                 170                 175

His Gly Ala Asp Asp His Lys Glu Val Leu Val Trp Arg Phe Asp
            180                 185                 190

Ser Ser Leu Ala Arg Arg His Val Ala Arg Glu Leu His Pro Glu Phe
        195                 200                 205

Tyr Lys Asn Cys
    210

<210> SEQ ID NO 21
<211> LENGTH: 20
<212> TYPE: DNA
<213> ORGANISM: artificial sequence
<220> FEATURE:
<223> OTHER INFORMATION: primer

<400> SEQUENCE: 21
attgcgtact cacacttccg                                              20

<210> SEQ ID NO 22
<211> LENGTH: 17
<212> TYPE: DNA
<213> ORGANISM: artificial sequence
<220> FEATURE:
<223> OTHER INFORMATION: primer

<400> SEQUENCE: 22
ggcaagcagg gagctgg                                                 17

<210> SEQ ID NO 23
<211> LENGTH: 18
<212> TYPE: DNA
<213> ORGANISM: artificial sequence
<220> FEATURE:
```

-continued

<223> OTHER INFORMATION: primer

<400> SEQUENCE: 23
tccttgagca gtctggac                                                 18

<210> SEQ ID NO 24
<211> LENGTH: 18
<212> TYPE: DNA
<213> ORGANISM: artificial sequence
<220> FEATURE:
<223> OTHER INFORMATION: primer

<400> SEQUENCE: 24
gaacaggagg attagcag                                                 18

<210> SEQ ID NO 25
<211> LENGTH: 18
<212> TYPE: DNA
<213> ORGANISM: artificial sequence
<220> FEATURE:
<223> OTHER INFORMATION: primer

<400> SEQUENCE: 25
agcagaggct atgtcaca                                                 18

<210> SEQ ID NO 26
<211> LENGTH: 19
<212> TYPE: DNA
<213> ORGANISM: artificial sequence
<220> FEATURE:
<223> OTHER INFORMATION: primer

<400> SEQUENCE: 26
tgtaaggccc ctagaagag                                                19

<210> SEQ ID NO 27
<211> LENGTH: 18
<212> TYPE: DNA
<213> ORGANISM: artificial sequence
<220> FEATURE:
<223> OTHER INFORMATION: primer

<400> SEQUENCE: 27
acagagaact ctctgtac                                                 18

<210> SEQ ID NO 28
<211> LENGTH: 18
<212> TYPE: DNA
<213> ORGANISM: artificial sequence
<220> FEATURE:
<223> OTHER INFORMATION: primer

<400> SEQUENCE: 28 aagaaagca gttggtac                                                  18

<210> SEQ ID NO 29
<211> LENGTH: 17
<212> TYPE: DNA
<213> ORGANISM: artificial sequence
<220> FEATURE:
<223> OTHER INFORMATION: primer

<400> SEQUENCE: 29
tttcttccct gtatgtc                                                  17

```
<210> SEQ ID NO 30
<211> LENGTH: 18
<212> TYPE: DNA
<213> ORGANISM: artificial sequence
<220> FEATURE:
<223> OTHER INFORMATION: primer

<400> SEQUENCE: 30
gttatatgga ttctcagg                                                 18

<210> SEQ ID NO 31
<211> LENGTH: 19
<212> TYPE: DNA
<213> ORGANISM: artificial sequence
<220> FEATURE:
<223> OTHER INFORMATION: primer

<400> SEQUENCE: 31
tggcagcaca tttatactgg                                               19

<210> SEQ ID NO 32
<211> LENGTH: 23
<212> TYPE: DNA
<213> ORGANISM: artificial sequence
<220> FEATURE:
<223> OTHER INFORMATION: primer

<400> SEQUENCE: 32
atcatttacc agtacatgga cga                                           23

<210> SEQ ID NO 33
<211> LENGTH: 18
<212> TYPE: DNA
<213> ORGANISM: artificial sequence
<220> FEATURE:
<223> OTHER INFORMATION: primer

<400> SEQUENCE: 33
tgtcaggggt cgtaaagc                                                 18

<210> SEQ ID NO 34
<211> LENGTH: 18
<212> TYPE: DNA
<213> ORGANISM: artificial sequence
<220> FEATURE:
<223> OTHER INFORMATION: primer

<400> SEQUENCE: 34
tcctctggat gggatatg                                                 18

<210> SEQ ID NO 35
<211> LENGTH: 18
<212> TYPE: DNA
<213> ORGANISM: artificial sequence
<220> FEATURE:
<223> OTHER INFORMATION: primer

<400> SEQUENCE: 35
tctatccagg aatcagag                                                 18

<210> SEQ ID NO 36
<211> LENGTH: 18
<212> TYPE: DNA
<213> ORGANISM: artificial sequence
<220> FEATURE:
<223> OTHER INFORMATION: primer
```

-continued

```
<400> SEQUENCE: 36
aatgagatct gcccatac                                                 18

<210> SEQ ID NO 37
<211> LENGTH: 18
<212> TYPE: DNA
<213> ORGANISM: artificial sequence
<220> FEATURE:
<223> OTHER INFORMATION: primer

<400> SEQUENCE: 37
tgacagatag gggaagac                                                 18

<210> SEQ ID NO 38
<211> LENGTH: 18
<212> TYPE: DNA
<213> ORGANISM: artificial sequence
<220> FEATURE:
<223> OTHER INFORMATION: primer

<400> SEQUENCE: 38
aaccgccatt tgcactgc                                                 18

<210> SEQ ID NO 39
<211> LENGTH: 18
<212> TYPE: DNA
<213> ORGANISM: artificial sequence
<220> FEATURE:
<223> OTHER INFORMATION: primer

<400> SEQUENCE: 39
acatggaccg ccacaagg                                                 18

<210> SEQ ID NO 40
<211> LENGTH: 18
<212> TYPE: DNA
<213> ORGANISM: artificial sequence
<220> FEATURE:
<223> OTHER INFORMATION: primer

<400> SEQUENCE: 40
agcaacagac atacagac                                                 18

<210> SEQ ID NO 41
<211> LENGTH: 18
<212> TYPE: DNA
<213> ORGANISM: artificial sequence
<220> FEATURE:
<223> OTHER INFORMATION: primer

<400> SEQUENCE: 41
aaagtagtcc cacgtagg                                                 18

<210> SEQ ID NO 42
<211> LENGTH: 18
<212> TYPE: DNA
<213> ORGANISM: artificial sequence
<220> FEATURE:
<223> OTHER INFORMATION: primer

<400> SEQUENCE: 42
atatcccagt aggtcagg                                                 18

<210> SEQ ID NO 43
<211> LENGTH: 18
```

```
<212> TYPE: DNA
<213> ORGANISM: artificial sequence
<220> FEATURE:
<223> OTHER INFORMATION: primer

<400> SEQUENCE: 43
tctagcacta acagcctg                                               18

<210> SEQ ID NO 44
<211> LENGTH: 18
<212> TYPE: DNA
<213> ORGANISM: artificial sequence
<220> FEATURE:
<223> OTHER INFORMATION: primer

<400> SEQUENCE: 44
actcttactg ctctgagg                                               18

<210> SEQ ID NO 45
<211> LENGTH: 18
<212> TYPE: DNA
<213> ORGANISM: artificial sequence
<220> FEATURE:
<223> OTHER INFORMATION: primer

<400> SEQUENCE: 45
ccatagtaca ctgttacc                                               18

<210> SEQ ID NO 46
<211> LENGTH: 20
<212> TYPE: DNA
<213> ORGANISM: artificial sequence
<220> FEATURE:
<223> OTHER INFORMATION: primer

<400> SEQUENCE: 46
catagctatc gttacaaagc                                             20

<210> SEQ ID NO 47
<211> LENGTH: 18
<212> TYPE: DNA
<213> ORGANISM: artificial sequence
<220> FEATURE:
<223> OTHER INFORMATION: primer

<400> SEQUENCE: 47
tcataatggc aaagcctg                                               18

<210> SEQ ID NO 48
<211> LENGTH: 18
<212> TYPE: DNA
<213> ORGANISM: artificial sequence
<220> FEATURE:
<223> OTHER INFORMATION: primer

<400> SEQUENCE: 48
ctattccaca ttggttcc                                               18

<210> SEQ ID NO 49
<211> LENGTH: 18
<212> TYPE: DNA
<213> ORGANISM: artificial sequence
<220> FEATURE:
<223> OTHER INFORMATION: primer

<400> SEQUENCE: 49
```

```
attctagaac cagtccag                                                  18

<210> SEQ ID NO 50
<211> LENGTH: 20
<212> TYPE: DNA
<213> ORGANISM: artificial sequence
<220> FEATURE:
<223> OTHER INFORMATION: primer for HIV type 1

<400> SEQUENCE: 50
ccttagggat cagcaaatcc                                                20

<210> SEQ ID NO 51
<211> LENGTH: 18
<212> TYPE: DNA
<213> ORGANISM: artificial sequence
<220> FEATURE:
<223> OTHER INFORMATION: primer

<400> SEQUENCE: 51
tgggacagtc tgtggagc                                                  18

<210> SEQ ID NO 52
<211> LENGTH: 18
<212> TYPE: DNA
<213> ORGANISM: artificial sequence
<220> FEATURE:
<223> OTHER INFORMATION: primer

<400> SEQUENCE: 52
ttctcagctc ttgtctgg                                                  18

<210> SEQ ID NO 53
<211> LENGTH: 18
<212> TYPE: DNA
<213> ORGANISM: artificial sequence
<220> FEATURE:
<223> OTHER INFORMATION: primer

<400> SEQUENCE: 53
attaagcaag ctgatagc                                                  18

<210> SEQ ID NO 54
<211> LENGTH: 16
<212> TYPE: DNA
<213> ORGANISM: artificial sequence
<220> FEATURE:
<223> OTHER INFORMATION: primer

<400> SEQUENCE: 54
tgtgcttcta gccaag                                                    16

<210> SEQ ID NO 55
<211> LENGTH: 18
<212> TYPE: DNA
<213> ORGANISM: artificial sequence
<220> FEATURE:
<223> OTHER INFORMATION: primer

<400> SEQUENCE: 55
gctccatgtt gacatatg                                                  18

<210> SEQ ID NO 56
<211> LENGTH: 18
<212> TYPE: DNA
<213> ORGANISM: artificial sequence
```

```
<220> FEATURE:
<223> OTHER INFORMATION: primer

<400> SEQUENCE: 56
agagagaccc agtacaag                                                    18

<210> SEQ ID NO 57
<211> LENGTH: 20
<212> TYPE: DNA
<213> ORGANISM: artificial sequence
<220> FEATURE:
<223> OTHER INFORMATION: primer

<400> SEQUENCE: 57
ataaaagcag ccgcttctcg                                                  20

<210> SEQ ID NO 58
<211> LENGTH: 35
<212> TYPE: PRT
<213> ORGANISM: Human immunodeficiency virus type 1

<400> SEQUENCE: 58

Cys Thr Arg Pro Gly Asn Asn Thr Gly Gly Gln Val Gln Ile Gly Pro
 1               5                  10                  15

Ala Met Thr Phe Tyr Asn Ile Glu Lys Ile Val Gly Asp Ile Arg Gln
            20                  25                  30

Ala Tyr Cys
        35

<210> SEQ ID NO 59
<211> LENGTH: 35
<212> TYPE: PRT
<213> ORGANISM: Human immunodeficiency virus type 1

<400> SEQUENCE: 59

Cys His Arg Pro Gly Asn Asn Thr Arg Gly Glu Val Gln Ile Gly Pro
 1               5                  10                  15

Gly Met Thr Phe Tyr Asn Ile Glu Asn Val Tyr Gly Asp Thr Arg Ser
            20                  25                  30

Ala Tyr Cys
        35

<210> SEQ ID NO 60
<211> LENGTH: 35
<212> TYPE: PRT
<213> ORGANISM: Human immunodeficiency virus type 1

<400> SEQUENCE: 60

Cys Ile Arg Pro Gly Asn Arg Thr Tyr Arg Asn Leu Gln Ile Gly Pro
1                5                  10                  15

Gly Met Thr Phe Tyr Asn Val Glu Ile Ala Thr Gly Asp Ile Arg Lys
            20                  25                  30

Ala Phe Cys
        35

<210> SEQ ID NO 61
<211> LENGTH: 35
<212> TYPE: PRT
<213> ORGANISM: Human immunodeficiency virus type 1

<400> SEQUENCE: 61

Cys Thr Arg Pro Asn Asn Asn Thr Arg Lys Ser Val Arg Ile Gly Pro
```

```
  1               5              10              15
Gly Gln Ala Phe Tyr Ala Thr Gly Asp Ile Ile Gly Asp Ile Arg Gln
                 20                  25                  30

Ala His Cys
        35
```

<210> SEQ ID NO 62
<211> LENGTH: 18
<212> TYPE: DNA
<213> ORGANISM: artificial sequence
<220> FEATURE:
<223> OTHER INFORMATION: primer

<400> SEQUENCE: 62
agcaacagac atacagac                                         18

<210> SEQ ID NO 63
<211> LENGTH: 18
<212> TYPE: DNA
<213> ORGANISM: artificial sequence
<220> FEATURE:
<223> OTHER INFORMATION: primer

<400> SEQUENCE: 63
aaagtagtcc cacgtagg                                         18

<210> SEQ ID NO 64
<211> LENGTH: 18
<212> TYPE: DNA
<213> ORGANISM: artificial sequence
<220> FEATURE:
<223> OTHER INFORMATION: primer

<400> SEQUENCE: 64
atatcccagt aggtcagg                                         18

<210> SEQ ID NO 65
<211> LENGTH: 18
<212> TYPE: DNA
<213> ORGANISM: artificial sequence
<220> FEATURE:
<223> OTHER INFORMATION: primer

<400> SEQUENCE: 65
tctagcacta acagcctg                                         18

<210> SEQ ID NO 66
<211> LENGTH: 18
<212> TYPE: DNA
<213> ORGANISM: artificial sequence
<220> FEATURE:
<223> OTHER INFORMATION: primer

<400> SEQUENCE: 66
aaccgccatt tgcactgc                                         18

<210> SEQ ID NO 67
<211> LENGTH: 18
<212> TYPE: DNA
<213> ORGANISM: artificial sequence
<220> FEATURE:
<223> OTHER INFORMATION: primer

<400> SEQUENCE: 67
acatggaccg ccacaagg                                         18

<210> SEQ ID NO 68
<211> LENGTH: 18
<212> TYPE: DNA
<213> ORGANISM: artificial sequence
<220> FEATURE:
<223> OTHER INFORMATION: primer

<400> SEQUENCE: 68
agcagaggct atgtcaca                                                18

<210> SEQ ID NO 69
<211> LENGTH: 18
<212> TYPE: DNA
<213> ORGANISM: artificial sequence
<220> FEATURE:
<223> OTHER INFORMATION: primer

<400> SEQUENCE: 69
gaacaggagg attagcag                                                18

<210> SEQ ID NO 70
<211> LENGTH: 18
<212> TYPE: DNA
<213> ORGANISM: artificial sequence
<220> FEATURE:
<223> OTHER INFORMATION: primer

<400> SEQUENCE: 70
tccttgagca gtctggac                                                18

<210> SEQ ID NO 71
<211> LENGTH: 18
<212> TYPE: DNA
<213> ORGANISM: Human immunodeficiency virus type 1

<400> SEQUENCE: 71
acagagaact ctctgtac                                                18

<210> SEQ ID NO 72
<211> LENGTH: 18
<212> TYPE: DNA
<213> ORGANISM: artificial sequence
<220> FEATURE:
<223> OTHER INFORMATION: primer

<400> SEQUENCE: 72
aagaaaagca gttggtac                                                18

<210> SEQ ID NO 73
<211> LENGTH: 19
<212> TYPE: DNA
<213> ORGANISM: artificial sequence
<220> FEATURE:
<223> OTHER INFORMATION: primer

<400> SEQUENCE: 73
tgtaaggccc ctagaagag                                               19

<210> SEQ ID NO 74
<211> LENGTH: 17
<212> TYPE: DNA
<213> ORGANISM: artificial sequence
<220> FEATURE:
<223> OTHER INFORMATION: primer

```
<400> SEQUENCE: 74
ggcaagcagg gagctgg                                                    17

<210> SEQ ID NO 75
<211> LENGTH: 18
<212> TYPE: DNA
<213> ORGANISM: artificial sequence
<220> FEATURE:
<223> OTHER INFORMATION: primer

<400> SEQUENCE: 75
agagagaccc agtacaag                                                   18

<210> SEQ ID NO 76
<211> LENGTH: 18
<212> TYPE: DNA
<213> ORGANISM: artificial sequence
<220> FEATURE:
<223> OTHER INFORMATION: primer

<400> SEQUENCE: 76
gctccatgtt gacatatg                                                   18

<210> SEQ ID NO 77
<211> LENGTH: 16
<212> TYPE: DNA
<213> ORGANISM: artificial sequence
<220> FEATURE:
<223> OTHER INFORMATION: primer

<400> SEQUENCE: 77
tgtgcttcta gccaag                                                     16

<210> SEQ ID NO 78
<211> LENGTH: 18
<212> TYPE: DNA
<213> ORGANISM: artificial sequence
<220> FEATURE:
<223> OTHER INFORMATION: primer

<400> SEQUENCE: 78
attaagcaag ctgatagc                                                   18

<210> SEQ ID NO 79
<211> LENGTH: 20
<212> TYPE: DNA
<213> ORGANISM: artificial sequence
<220> FEATURE:
<223> OTHER INFORMATION: primer

<400> SEQUENCE: 79
ccttagggat cagcaaatcc                                                 20

<210> SEQ ID NO 80
<211> LENGTH: 18
<212> TYPE: DNA
<213> ORGANISM: artificial sequence
<220> FEATURE:
<223> OTHER INFORMATION: primer

<400> SEQUENCE: 80
tgggacagtc tgtggagc                                                   18

<210> SEQ ID NO 81
<211> LENGTH: 18
```

<212> TYPE: DNA
<213> ORGANISM: artificial sequence
<220> FEATURE:
<223> OTHER INFORMATION: primer

<400> SEQUENCE: 81
ttctcagctc ttgtctgg                                            18

<210> SEQ ID NO 82
<211> LENGTH: 18
<212> TYPE: DNA
<213> ORGANISM: artificial sequence
<220> FEATURE:
<223> OTHER INFORMATION: primer

<400> SEQUENCE: 82
attctagaac cagtccag                                            18

<210> SEQ ID NO 83
<211> LENGTH: 18
<212> TYPE: DNA
<213> ORGANISM: artificial sequence
<220> FEATURE:
<223> OTHER INFORMATION: primer

<400> SEQUENCE: 83
ctattccaca ttggttcc                                            18

<210> SEQ ID NO 84
<211> LENGTH: 18
<212> TYPE: DNA
<213> ORGANISM: artificial sequence
<220> FEATURE:
<223> OTHER INFORMATION: primer

<400> SEQUENCE: 84
tcataatggc aaagcctg                                            18

<210> SEQ ID NO 85
<211> LENGTH: 20
<212> TYPE: DNA
<213> ORGANISM: artificial sequence
<220> FEATURE:
<223> OTHER INFORMATION: primer

<400> SEQUENCE: 85
catagctatc gttacaaagc                                          20

<210> SEQ ID NO 86
<211> LENGTH: 18
<212> TYPE: DNA
<213> ORGANISM: artificial sequence
<220> FEATURE:
<223> OTHER INFORMATION: primer

<400> SEQUENCE: 86
ccatagtaca ctgttacc                                            18

<210> SEQ ID NO 87
<211> LENGTH: 18
<212> TYPE: DNA
<213> ORGANISM: artificial sequence
<220> FEATURE:
<223> OTHER INFORMATION: primer

<400> SEQUENCE: 87

-continued actcttactg ctctgagg                                              18

<210> SEQ ID NO 88
<211> LENGTH: 20
<212> TYPE: DNA
<213> ORGANISM: artificial sequence
<220> FEATURE:
<223> OTHER INFORMATION: primer

<400> SEQUENCE: 88
attgcgtact cacacttccg                                            20

<210> SEQ ID NO 89
<211> LENGTH: 20
<212> TYPE: DNA
<213> ORGANISM: artificial sequence
<220> FEATURE:
<223> OTHER INFORMATION: primer

<400> SEQUENCE: 89
ataaaagcag ccgcttctcg                                            20

<210> SEQ ID NO 90
<211> LENGTH: 18
<212> TYPE: DNA
<213> ORGANISM: artificial sequence
<220> FEATURE:
<223> OTHER INFORMATION: primer

<400> SEQUENCE: 90
tcctctggat gggatatg                                              18

<210> SEQ ID NO 91
<211> LENGTH: 18
<212> TYPE: DNA
<213> ORGANISM: artificial sequence
<220> FEATURE:
<223> OTHER INFORMATION: primer

<400> SEQUENCE: 91
tctatccagg aatcagag                                              18

<210> SEQ ID NO 92
<211> LENGTH: 18
<212> TYPE: DNA
<213> ORGANISM: artificial sequence
<220> FEATURE:
<223> OTHER INFORMATION: primer

<400> SEQUENCE: 92
tgacagatag gggaagac                                              18

<210> SEQ ID NO 93
<211> LENGTH: 23
<212> TYPE: DNA
<213> ORGANISM: artificial sequence
<220> FEATURE:
<223> OTHER INFORMATION: primer

<400> SEQUENCE: 93
atcatttacc agtacatgga cga                                        23

<210> SEQ ID NO 94
<211> LENGTH: 18
<212> TYPE: DNA
<213> ORGANISM: artificial sequence -continued

```
<220> FEATURE:
<223> OTHER INFORMATION: primer

<400> SEQUENCE: 94
aatgagatct gcccatac                                                  18

<210> SEQ ID NO 95
<211> LENGTH: 19
<212> TYPE: DNA
<213> ORGANISM: artificial sequence
<220> FEATURE:
<223> OTHER INFORMATION: primer

<400> SEQUENCE: 95
tggcagcaca ttatactgg                                                 19

<210> SEQ ID NO 96
<211> LENGTH: 18
<212> TYPE: DNA
<213> ORGANISM: artificial sequence
<220> FEATURE:
<223> OTHER INFORMATION: primer

<400> SEQUENCE: 96
gttatatgga ttctcagg                                                  18

<210> SEQ ID NO 97
<211> LENGTH: 17
<212> TYPE: DNA
<213> ORGANISM: artificial sequence
<220> FEATURE:
<223> OTHER INFORMATION: primer

<400> SEQUENCE: 97
tttcttccct gtatgtc                                                   17

<210> SEQ ID NO 98
<211> LENGTH: 18
<212> TYPE: DNA
<213> ORGANISM: artificial sequence
<220> FEATURE:
<223> OTHER INFORMATION: primer

<400> SEQUENCE: 98
tgtcaggggt cgtaaagc                                                  18

<210> SEQ ID NO 99
<211> LENGTH: 28
<212> TYPE: DNA
<213> ORGANISM: artificial sequence
<220> FEATURE:
<223> OTHER INFORMATION: primer

<400> SEQUENCE: 99
cggttcttag ggagcagcac tggaagca                                       28

<210> SEQ ID NO 100
<211> LENGTH: 35
<212> TYPE: DNA
<213> ORGANISM: artificial sequence
<220> FEATURE:
<223> OTHER INFORMATION: primer

<400> SEQUENCE: 100
tcttacgttc ccacttatct aagtccaagt gtcat                               35
```

NON-M, NON-O HIV-1 STRAINS, FRAGMENTS AND USES

This application is a divisional of application Ser. No. 10/301,661, filed Nov. 22, 2002, now U.S. Pat. No. 7,030,234 which is a divisional of application Ser. No. 09/319,588, filed Aug. 27, 1999, now U.S. Pat. No. 6,509,018 which is the National Stage of International Application No. PCT/FR97/02227, filed Dec. 8, 1997, which claims priority to France Application No. 96/15087 filed Dec. 9, 1996, which are herein incorporrated by reference in their entirety.

The present invention relates to retroviral strains of the non-M, non-O HIV-1 group, in particular a strain designated YBF30, to its fragments and to its uses as a diagnostic reagent and as an immunogenic agent.

The human acquired immunodeficiency viruses HIV-1 and HIV-2 are retrolentiviruses, which are viruses found in a large number of African primates. All these viruses appear to have a common ancestor; however, it is very difficult to prejudge the period at which these different viruses became separated from this precursor. Other viruses which are more distant, but which nevertheless belong to the same group, are found in other mammals (ungulates and felines).

All these viruses are associated with long infections; an absence of symptoms is the rule in monkeys which are infected naturally.

While the origin of HIV-2 appears to be clear on account of its strong homology with the Sooty Mangabey (West Africa) virus, no virus which is closely related to HIV-1 has been found in monkeys. The most closely related viruses are viruses found in two chimpanzees (CPZGAB SIV, ANT SIV).

All the lentiviruses have been found to exhibit substantial genetic variability, and the phylogenetic study of these variants, obtained from a large number of different geographic locations, has enabled 8 subtypes (clades) of HIV-1 to be distinguished, all of which are equidistant from each other. The clades are only a mathematical representation of the expression of the variability: phenetic analysis, which is based on the amino acids rather than on the nucleic acids, gives different results (Korber et al., 1994).

The demonstration of subtypes is in accord with a phylogenetic analysis which does not, to date, have any pathophysiological correlation but, instead, a geographical correspondence. This is because each subtype is mainly found in a particular geographical area. The B subtype is predominant in Europe and the United States whereas two subtypes, i.e. E and B, are found in Thailand and there is a strong correlation between the mode of transmission which, in actual fact, corresponds to a particular population and the subtype found. All the clades have been found in Africa and their distribution across the rest of the world reflects a probability of encounter between persons indulging in high-risk behaviour. The main clade, which is the main one because it is present in substantial proportions in Africa, is clade A. A very great degree of variability has been found in some African countries (G. Myers, 1994; P. M. Sharp et al., 1994). Several subtypes have been characterized in the western central African countries such as the Central African Republic (Murphy et al., 1993) and Cameroon (Nkengasong et al., 1994).

Finally, patients have been characterized who are carriers of viral variants of HIV-1, whose sera have posed detection problems for particular kits which are sold on the French market and whose confirmatory Western blots have been atypical (Loussert-Ajaka et al., 1994; Simon et al., 1994; PCT International Application WO 96/27013).

Analysis of these variants has confirmed the fact that the type 1 HIV viruses should be subdivided into two groups, i.e. the M (major) group and an O (outlier) group, which includes these isolates, as Charneau et al., 1994 had proposed. Analysis of the synonymous mutations/non-synonymous mutations ratio carried out on the sequences of the known O group viruses indicates that this new group is also ancient, even if no more ancient than the M group (Loussert-Ajaka et al., 1995). Its low prevalence to date, i.e. 8% of patients infected with HIV-1 in Cameroon (Zekeng et al., 1994) and 18 cases characterized in France, is thought to be due to factors which are purely epidemiological.

These two groups of HIV-1 form a tree which is in the shape of a double star (FIGS. 9 to 19). Two isolates, i.e. CPZGAB SIV, characterized from a chimpanzee from Gabon (Huet et al., 1990) and CPZANT SIV, characterized from a chimpanzee in the Antwerp Zoo, possess sequences and genetic organizations which are very closely related to HIV-1 but which do not fall within either of these two groups and form two new branches on the phylogenetic tree.

The demonstration of new variants is important for developing sufficiently sensitive and specific reagents for detecting HIV infections, that is to say reagents which do not lead to false-negative or false-positive results, and for developing compositions which are protective in regard to subtypes which do not belong either to the M group or to the O group.

Consequently, the applicant has set itself the objective of providing a non-M, non-O strain, as well as sequences derived from this strain, which are suitable for detecting non-M and non-O HIV-1 variants and which do not lead to false-negative or false-positive results being obtained. In order to do this, the inventors have, in particular, established an algorithm for differentiating between, and confirming, group M and group O HIV-1 infections, thereby enabling them to select non-M, non-O variants.

The present invention relates to a non-M, non-O HIV-1 strain which exhibits the morphological and immunological characteristics of the retrovirus which was deposited on 2 Jul. 1996 under number I-1753 (designated YBF30) in the Collection Nationale de Cultures de Microorganismes (National Collection of Microorganism Cultures, 28 rue du Docteur Roux, 75724 Paris Cedex 15), kept by the Pasteur Institute.

A non-M, non-O variant is understood as meaning a type 1 HIV which cannot serologically and molecularly be recognized as belonging to either of these groups.

The present invention also relates to the complete nucleotide sequence of the strain as defined above (SEQ ID NO: 1) as well as to nucleic acid fragments which are at least 10 nucleotides in size and which are derived from the said strain.

Fragments of this type which may be mentioned are:

```
YBF 30 LTR         (SEQ ID NO: 2),
YBF 30 GAG         (SEQ ID NO: 3) (gag gene),
YBF 30 POL         (SEQ ID NO: 5) (pol gene),
YBF 30 VIF         (SEQ ID NO: 7) (vif gene),
YBF 30 VPR         (SEQ ID NO: 9) (vpr gene),
YBF 30 VPU         (SEQ ID NO: 11) (vpu gene),
YBF 30 TAT         (SEQ ID NO: 13) (tat gene),
YBF 30 REV         (SEQ ID NO: 15) (rev gene),
YBF 30 ENV gp160   (SEQ ID NO: 17) (env gene),
YBF 30 NEF         (SEQ ID NO: 19) (nef gene),
``` the SEQ ID NOs: 21-57, also designated, respectively, YLG, LPBS.1, GAG Y AS1.1, GAGY AS1, GAG 6, GAG Y S1, GAG Y S1.1, GAG Y S1.2, YRT AS1.3, YRT AS1.2, YRT AS1.1, YRT 2, YRT AS1, YRT 2.1, YRT 2.2, YRT 2.3, YRT 2.4, 4481-1, 4481-2, 4235.1, 4235.2, 4235.3, 4235.4, SK69.6, SK69.5, SK69.4, SK69.3, SK69.2, SK69.1, SK68.1, SK68.2, SK68.3, LSI AS1.3, LSI AS1.2, LSI AS1.1, LSI A1, YLPA, as well as any sequence which is not identical to one of the above nucleotide sequences or is not complementary to one of these sequences but is nevertheless capable of hybridizing specifically with a nucleic acid sequence derived from a non-M, non-O HIV-1 virus.

Such sequences can be used in the specific identification of a non-M, non-O HIV-1, and as diagnostic reagents, either alone or pooled with other reagents, for the differential identification of any HIV-1.

These sequences may, in particular, be employed in diagnostic tests which comprise either a direct hybridization with the viral sequence to be detected or an amplification of the said viral sequence, with these tests using, as primers or as probes, an oligonucleotide which comprises at least 10 nucleotides and which is included in any one of the above sequences, in particular one of the abovementioned sequences, SEQ ID NOs: 21-57.

The present invention also relates to HIV-1 viruses which are characterized in that they differ both from the M group and from the O group and exhibit the following characteristics:
little or no serological reactivity with regard to proteins of the M and O groups and strong serological reactivity with regard to proteins which are derived from the YBF30 strain or the CPZGAB SIV strain;
absence of genomic amplification when using primers from the env and gag regions of HIV-1 viruses of the M and O groups;
genomic amplification in the presence of primers which are derived from the YBF30 strain, as defined above; and
homology of the products of the envelope gene which is >70% with regard to the YBF30 strain.

The invention also relates to the use of the above described sequences for implementing a method of hybridization and/or of gene amplification of nucleic acid sequences of the HIV-1 type, with these methods being applicable to the in-vitro diagnosis of the potential infection of an individual with a virus of the non-M, non-O HIV-1 type.

This in-vitro diagnostic method is carried out using a biological sample (serum or circulating lymphocyte) and comprises:
a step of extracting the nucleic acid which is to be detected and which belongs to the genome of the virus, which virus may possibly be present in the biological sample, and, where appropriate, a step of treating the nucleic acid using a reverse transcriptase, if this nucleic acid is in RNA form,
at least one cycle comprising the steps of denaturing the nucleic acid, of hybridizing with at least one sequence in accordance with the invention and, where appropriate, extending the hybrid, which has been formed, in the presence of suitable reagents (polymerizing agent, such as DNA polymerase and dNTP), and
a step of detecting the possible presence of the nucleic acid belonging to the genome of a virus of the non-M, non-O HIV-1 group type.

The following conditions are employed for the PCR using the primers derived from the YBF30 strain:
extracting the lymphocytic DNA by means of the phenol/chloroform technique and quantifying it by spectrophotometry at a wavelength of 260 nm. All the amplifications are carried out using a Perkin Elmer 2400 thermocycler.
the long (9 kb) PCRs are carried out using an XL PCR kit (Perkin Elmer) in accordance with the manufacturer's conditions and using the dNTP's, the buffers provided and Perkin Elmer's "hot start"; the amplification cycles of this long PCR are:
1 cycle of denaturation for 2 minutes at 94° C.,
then 16 cycles: 15 seconds at 94° C., 15 seconds at 55° C., 8 minutes at 68° C.,
then 24 cycles: 15 seconds at 94° C., 15 seconds at 55° C., 8 minutes at 68° C., adding a further 15 seconds (incrementation) to each cycle.
the nested PCRs are carried out on the amplification products of the long PCRs. The conditions for carrying out the nested PCRs are as follows:
"Expand High Fidelity PCR System" Taq polymerase buffer and enzyme from Boehringer Mannheim in accordance with the manufacturer's instructions, dNTP and "hot start" from Perkin Elmer,
200 μmol of each dNTP, 20 pmol of each primer in accordance with the invention, 5 μl of DNA, 10 μl of 10 ×PCR buffer and 2.6 units of Taq polymerase in a volume of 100 μl,
amplification: one cycle of 2 minutes at 940° C. followed by 38 cycles: 15 seconds at 940° C., 15 seconds at 55° C., a time of elongation at 72° C. which varies in accordance with the size of the PCR product to be amplified (from 30 seconds to 2 minutes) and a final elongation cycle of 10 minutes at 72° C.

The amplified product is preferably detected by direct sequencing.

The invention also relates to a peptide or a peptide fragment which is characterized in that it can be expressed by a non-M, non-O HIV-1 strain or using a nucleotide sequence as defined above, and in that it is capable: (1) of being recognized by antibodies which are induced by a non-M, non-O HIV-1 virus, as defined above, in particular the YBF30 strain or a variant of this strain, and which are present in a biological sample which is obtained following an infection with a non-M, non-O HIV-1 strain, and/or (2) of inducing the production of anti-non-M, non-O HIV-1 antibodies.

Peptides of this type which may be mentioned are, in particular, those which are derived from the YBF30 strain, in particular: that which is expressed by the gag gene (SEQ ID NO: 4), that which is expressed by the pol gene (SEQ ID NO: 6), that which is expressed by the vif gene (SEQ ID NO: 8), that which is expressed by the vpr gene (SEQ ID NO: 10), that which is expressed by the vpu gene (SEQ ID NO: 12), that which is expressed by the tat gene (SEQ ID NO: 14), that which is expressed by the rev gene (SEQ ID NO: 16), that which is expressed by the env gene (SEQ ID NO: 18), or one of its fragments such as a fragment of the V3 loop region, i.e. CTRPGNNTGGQVQJGPAMTFYNIEKIVGDIRQAYC (SEQ ID NO: 58), and that which is expressed by the nef gene (SEQ ID NO: 20), or a fragment of these peptides which are capable of recognizing the antibodies which are produced during an infection with a non-M, non-O HIV-1 as defined above.

The invention also relates to immunogenic compositions which comprise one or more translation products of the nucleotide sequences according to the invention and/or one of the peptides as defined above, obtained, in particular, by synthetic means.

The invention also relates to the antibodies which are directed against one or more of the above-described peptides and to their use for implementing methods for the in-vitro, in particular differential, diagnosis of the infection of an individual with a virus of the HIV-1 type using methods which are known to the skilled person.

The present invention encompasses all the peptides which are capable of being recognized by antibodies which are isolated from an infectious serum which is obtained after an infection with a non-M, non-O HIV-1 strain, and the peptides which are capable of being recognized by an antibody according to the invention.

The invention furthermore relates to a method for the in-vitro diagnosis of a non-M, non-O HIV-1 virus, which method is characterized in that it comprises bringing a biological sample, which has been taken from a patient, into contact with antibodies according to Claim 10, which may possibly be combined with anti-CPZGAB SIV antibodies, and detecting the immunological complexes which are formed between the HIV-1 antigens, which may possibly be present in the biological sample, and the said antibodies.

The invention also relates to a kit for diagnosing HIV-1, which kit is characterized in that it includes at least one reagent according to the invention.

Apart from the provisions which have been described above, the invention also comprises other provisions which will be evident from the description which follows and which refers to examples of implementing the method which is the subject of the present invention and also to the attached drawings, in which:

FIGS. 1 to 7 illustrate the location of the different primers on the genome of the YBF30 strain (SEQ ID NOs: 21-57 are listed from the top to the bottom of FIG. 1);

FIG. 20 illustrates the percentage genetic distance between YBF30 and HIV-1/CPZGAB SIV.

It should of course be understood, however, that these examples are given solely by way of illustrating the subject-matter of the invention, of which they in no way constitute a limitation.

EXAMPLE

Obtaining a non-M, non-O HIV-1 Variant According to the Invention (YBF30) and its uses This was, in particular, possible in connection with studying the epidemiology of infection with human acquired immunodeficiency viruses (HIV) in Cameroon, which epidemiology is especially paradoxical. In this country, the diversity of the strains is remarkable as most of the subtypes of the M (major) group of HIV-1 viruses known to date have been reported. Cases of infection with highly divergent HIV-1 viruses of the O group (O for outlier) have been reported, almost exclusively in patients of Cameroonian origin. Cases of infection with HIV-2, HTLV-1 and HTLV-2 subtypes A and B have also been reported.

Taking as a basis the results of previous serological and genotypic assessments, the inventors established an algorithm for differentiating between and confirming infections with HIV-1 viruses of the M and O groups in order to select non-M, non-O variants.

These methods were applied to samples which were sent to the National Reference Laboratory for HIV infections at Y aoundé and made it possible to characterize a highly divergent HIV isolate and to define the tools for characterizing a new HIV-1 group, taking into account the homologies which were observed between this human strain YBF30 and the simian strain CPZGAB SIV.

I—Way of Serologically Characterizing the YBF30 Variant During the Epidemiological Study 1) Collecting the Samples:

All the adult patient sera which were sent to the Yaoundé reference laboratory in 1994 and 1995 for detecting or confirming an HIV infection were studied (n=8831).

2) Differentiating Serologically Between Group M and Group HIV-1, and Selecting Variants:

If there was positive detection of anti-HIV antibodies (Génélavia Mixt indirect mixed HIV-1 and HIV-2 EIA, Sanofi-Pasteur, Paris, France), this was then combined with an EIA test based on the principle of competition with a specific antigen of the M group (Wellcozyme Rec HIV-1, Murex, Dartford, UK).

If the competitive Wellcozyme Rec HIV-1 test is positive, with a ratio for the reactivity in optical density (OD) as compared with the threshold or cut-off (CO) value which is greater than 5 (CO/OD>5), the serum is regarded as being HIV-1-positive, a result which should be confirmed on a new sample.

The choice of a reactivity ratio which is greater than 5 for regarding the competitive test as being a test for confirming infection with HIV-1 is based on experience acquired by the virology laboratory of Bichat hospital: all of 7200 samples which reacted with a ratio >5 gave a strongly positive HIV-1 Western blot (WB, New Lav Blot 1, SDP, Marnes la Coquette). Apart from cases of HIV-1 seroconversion, the samples which are confirmed as being HIV-positive and which give a Wellcozyme ratio of <5 correspond either to infections with HIV-2 or to infections with O group HIV-1 or other HIV-1 variants.

In order to eliminate the false-positive reactions when carrying out a mixed EIA detection, the samples which give a CO/OD ratio of <5 are tested systematically with a third generation mixed HIV-1/HIV-2 EIA (Enzygnost Plus, Marburg, Germany) which includes antigens of the M and O HIV-1 groups (recombinant gp41 of the MVP5180 strain). If this test is positive, a rapid test which discriminates between HIV-1 and HIV-2 (Multispot, SDP, Marnes la Coquette) and a Western blot (WB, New Lav Blot 1 or 2, SDP) are then carried out.

3) Serologically Confirming Infections with O Group HIV-1 and HIV-1 Variants.

All the samples which give a CO/OD ratio of <5, and which have been differentiated as being positive by WB (positivity criteria: 2 ENV+/−POL+/−GAG or 1 ENV+POL+/−GAG) and HIV-1, are tested with a dot blot test using peptide antigens of the V3 and transmembrane regions (InnoLia, Innogenetics, Ghent, Belgium).

4) Retroviral Isolation of the Group O Variant Strains.

The peripheral blood mononuclear cells (PBMC) from the seropositive patients were isolated by Ficoll-Hypaque gradient in Cameroon and then stored, and transported to Paris, in liquid nitrogen.

After thawing, the PBMCs from the patients were cocultured together with lymphocytes from seronegative Caucasian donors. Viral replication in the culture supernatants was demonstrated by detecting reverse transcriptase activity and by carrying out tests for detecting the p24 antigen (Elavia p24 polyclonal, SDP) over a period of one month.

5) Sequences:

The PCR products are visualized on agarose gels of from 1 to 1.4% concentration, depending on the size of the fragments, precipitated in 3M sodium acetate (1:10) and 3 volumes of absolute ethanol, incubated at −80° C. for 30 minutes and then centrifuged at 13,000 rpm for 20 minutes. The pellet is dried and then taken up in 10 µl of distilled water (Sigma). Purification is carried out on a "Qiaquick Gel Extraction kit" (Qiagen) in accordance with the manufacturer's instructions; the products are sequenced on an automated DNA sequencer (Applied Biosystems, Inc., Foster City, Calif.) using an Applied Biosystem Dye Terminator kit, as previously described (Loussert-Ajaka et al., 1995); the nucleotide sequences are analysed on Sequence Navigator software (Applied Biosystems), and aligned using GeneWorks software (Intelligenetics Inc.).

6) Phylogenetic Analyses:

The sequences were aligned using the CLUSTAL software for multiple alignments and taking, as the reference matrix, the alignments of the compilation of HIV sequences possessed by the Laboratory of Biology and Theoretical Biophysics, Los Alamos, N. Mex., 87545 USA.

Figure 2:
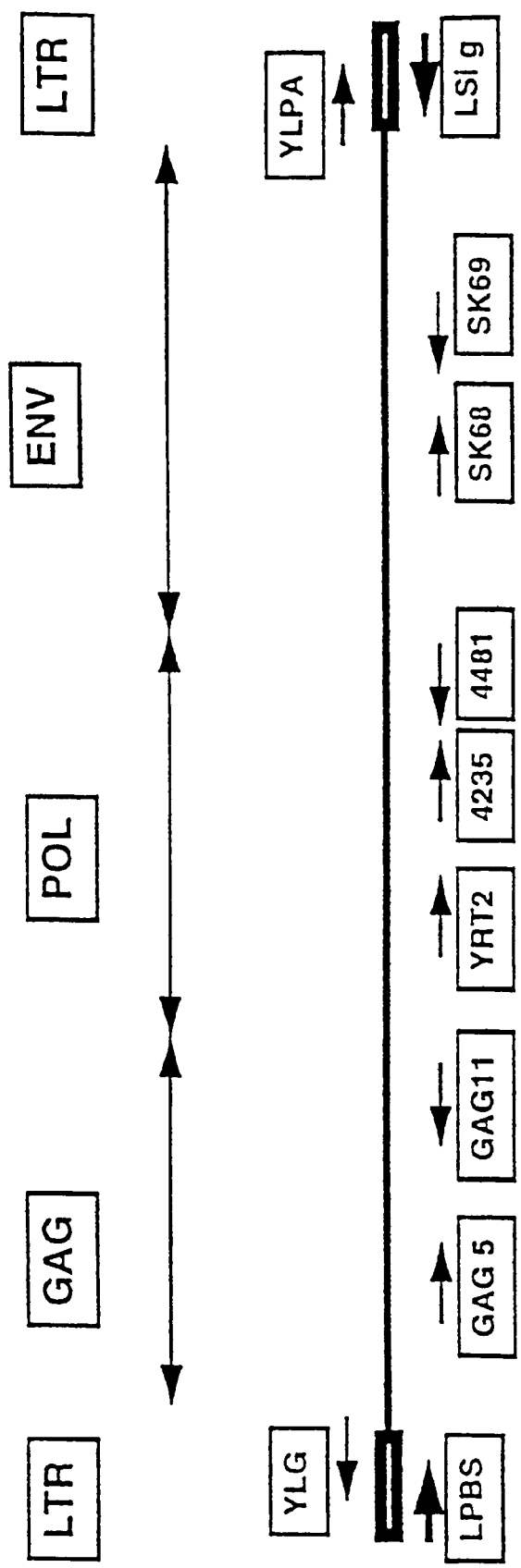
Figure 3:
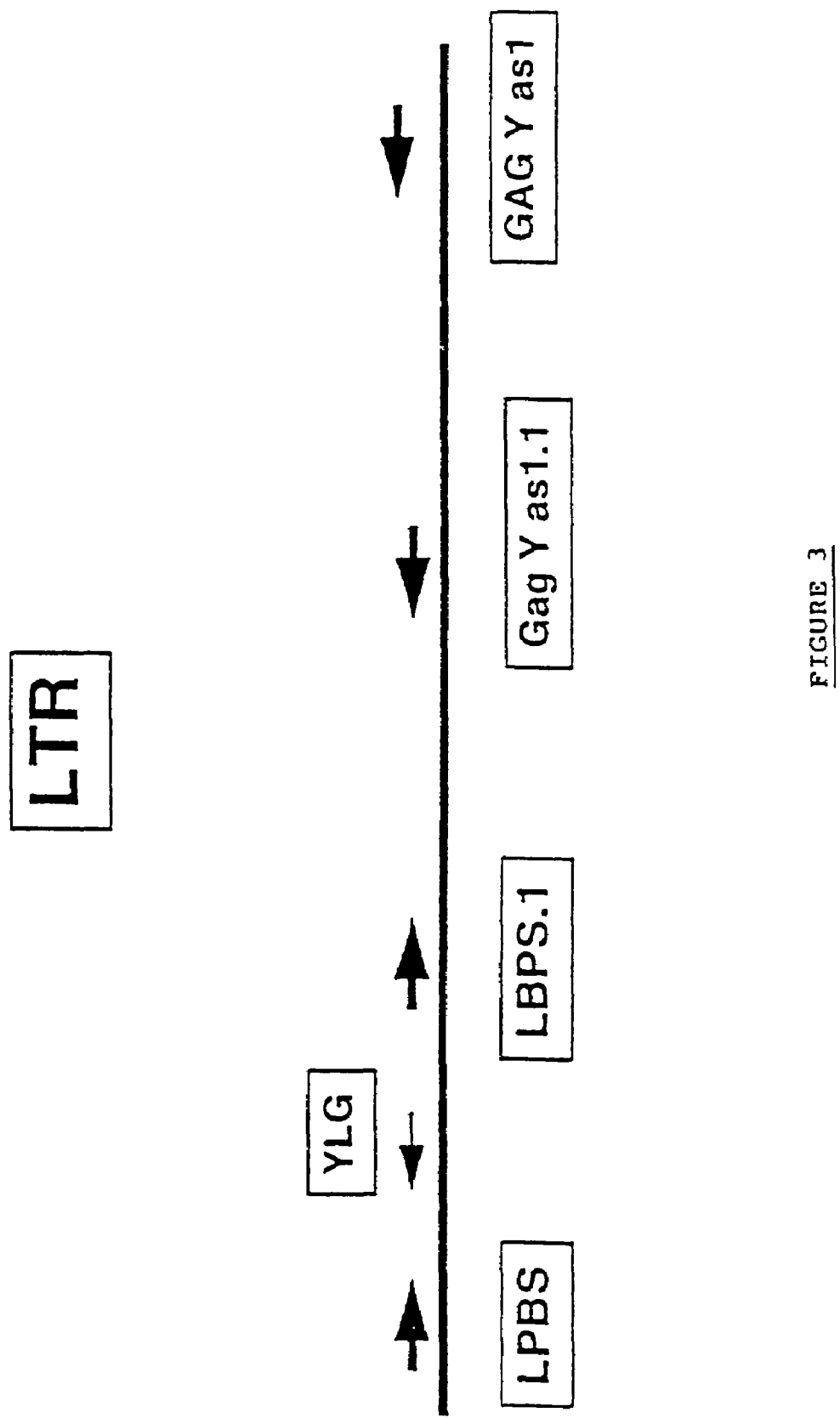
Figure 4:
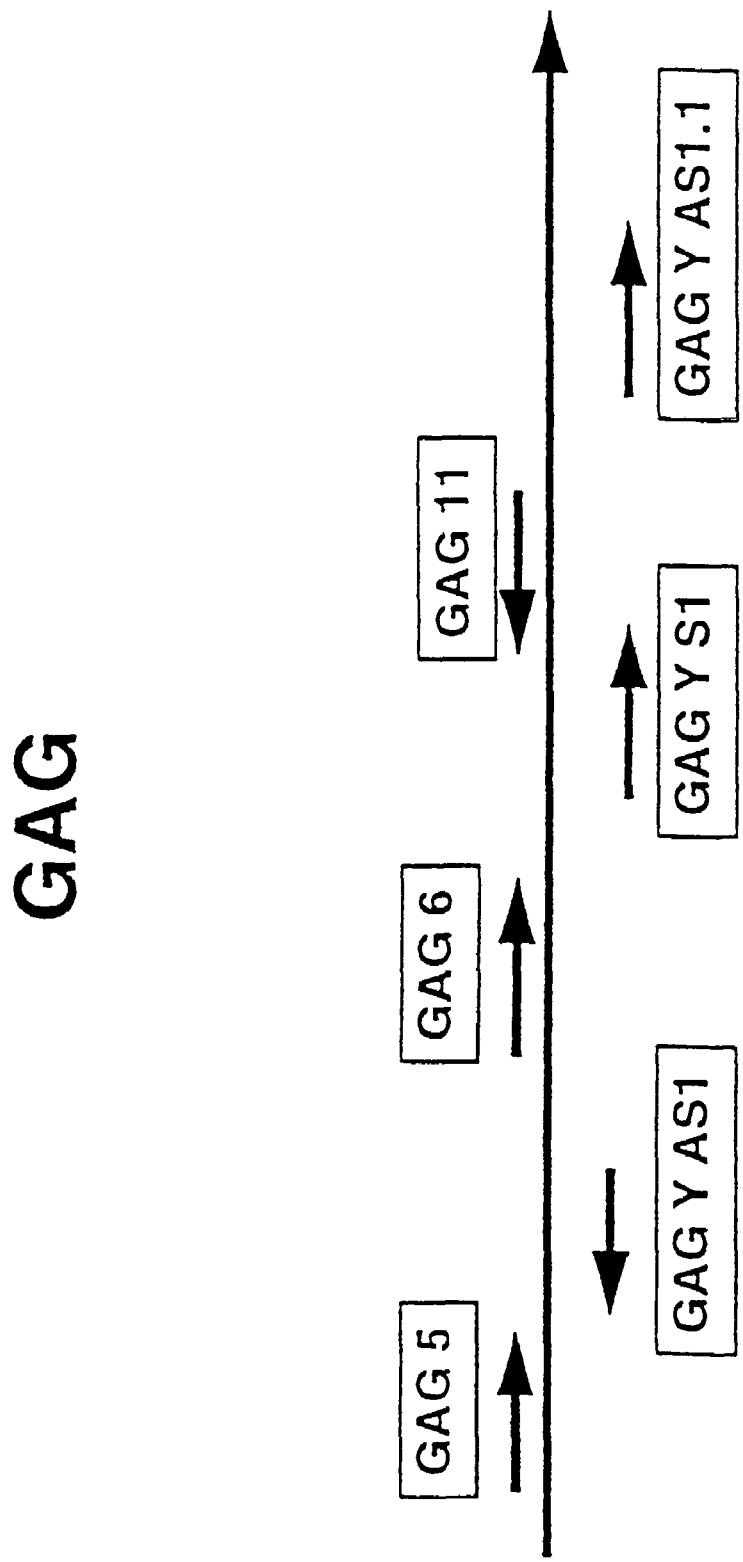
Figure 5:
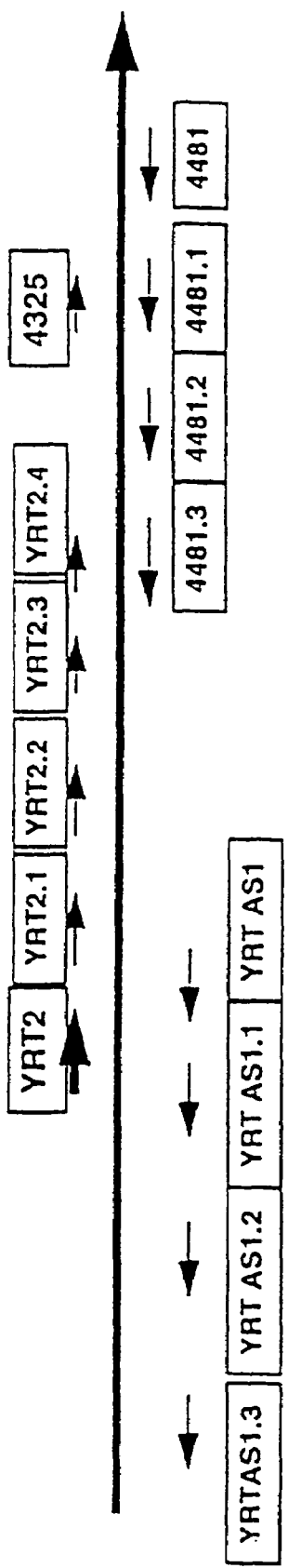
Figure 6:
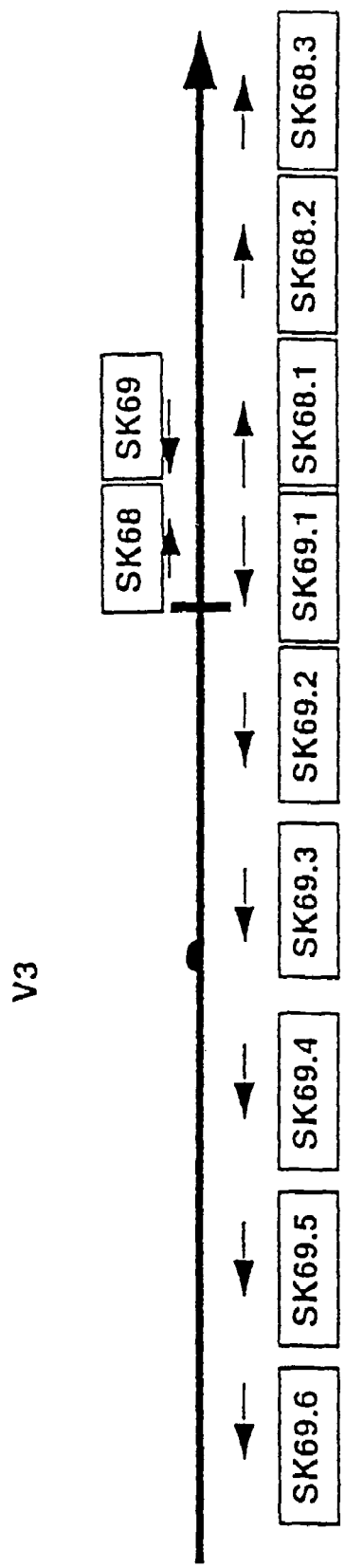
Figure 7:
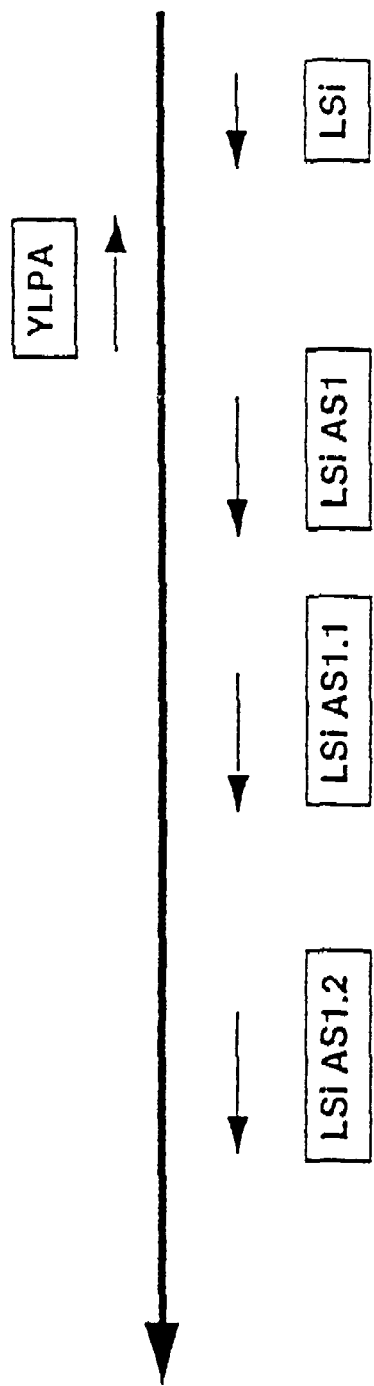
Figure 8:
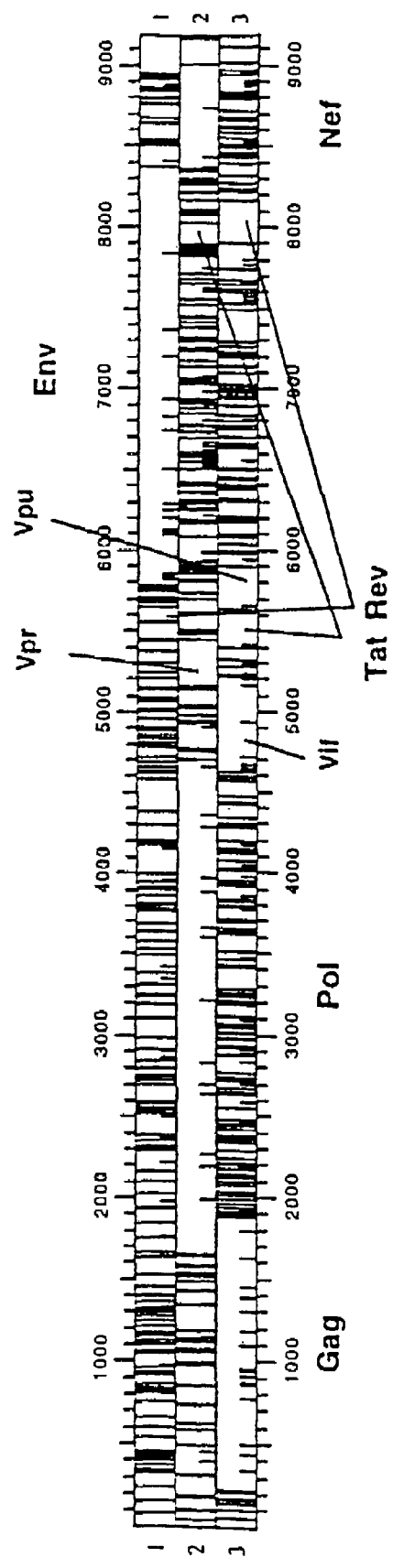
FIG. 8 illustrates the genomic organization of the YBF30 strain
Figure 9:
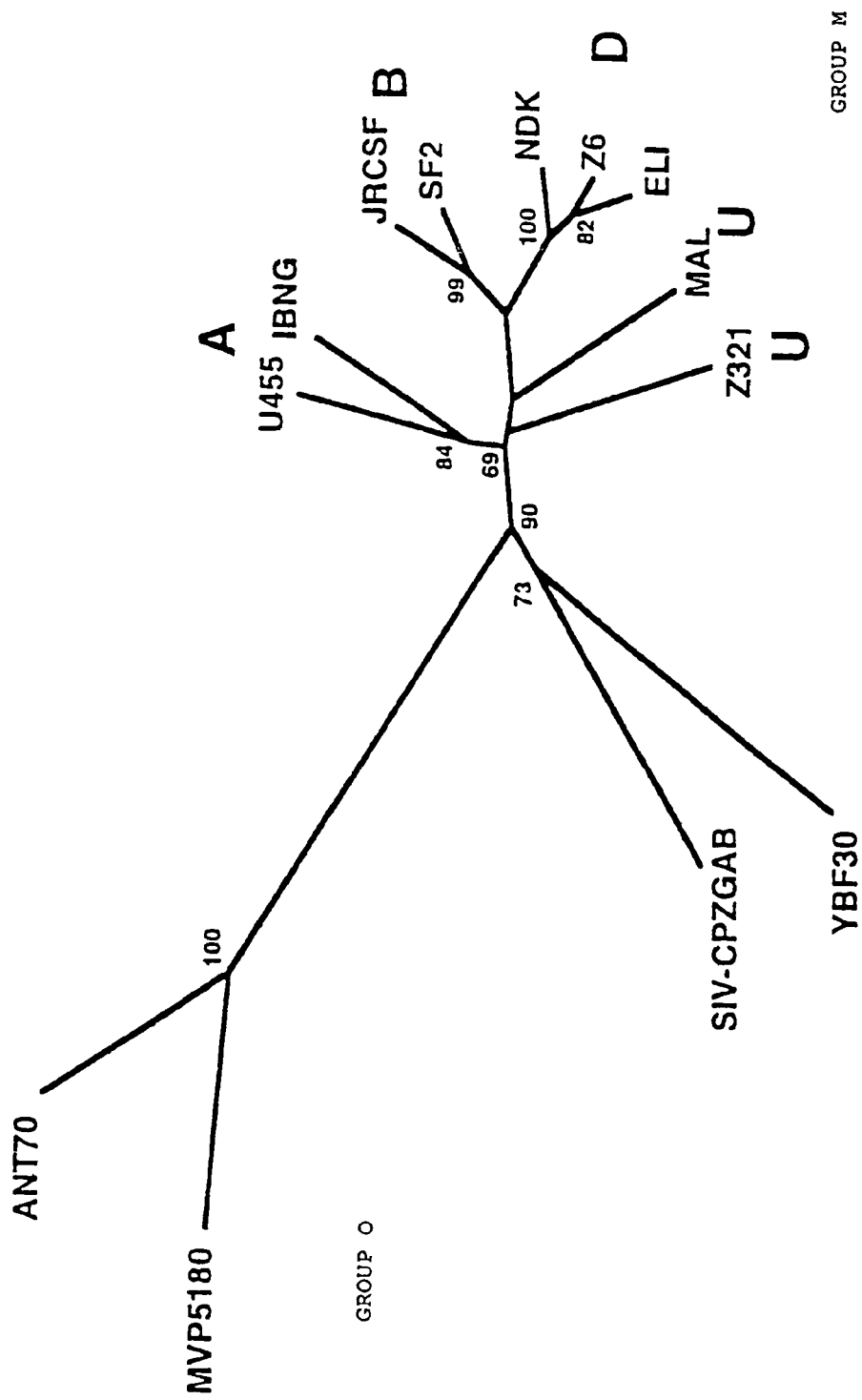
FIGS. 9 to 16 depict the phylogenetic analysis of the different genes of the YBF30 strain as compared with group M HIV-1 and group O HIV-1 (FIG. 9: ltr gene, FIG. 10: gag gene, FIG. 11: tat gene, FIG. 12: rev gene, FIG. 13: vif gene, FIG. 14: env gp120 gene, FIG. 15: env gp41 gene, FIG. 16: nef gene, FIG. 17: pol gene, FIG. 18: vpr gene, FIG. 19: vpu gene)
Figure 10:
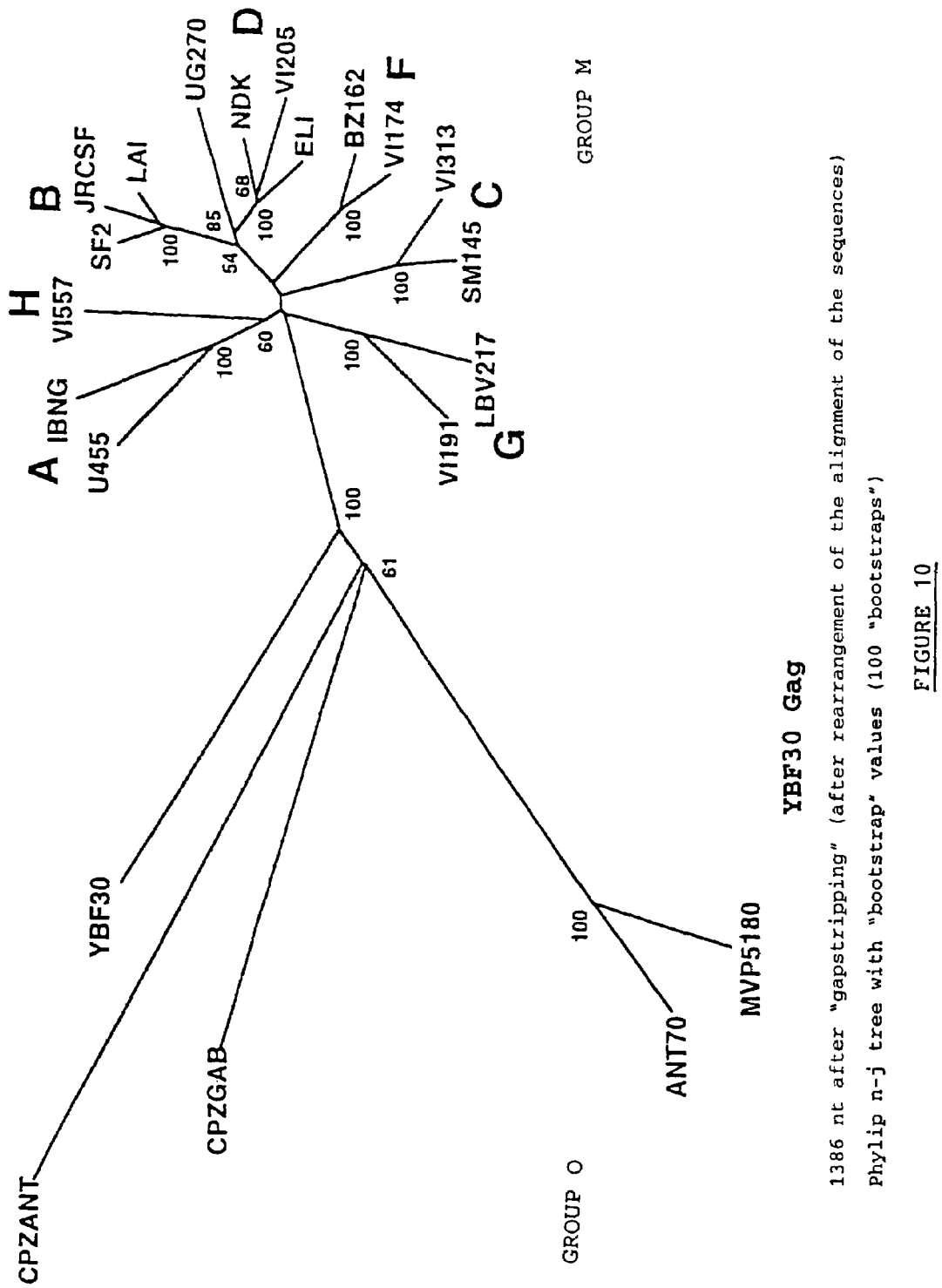
Figure 11:
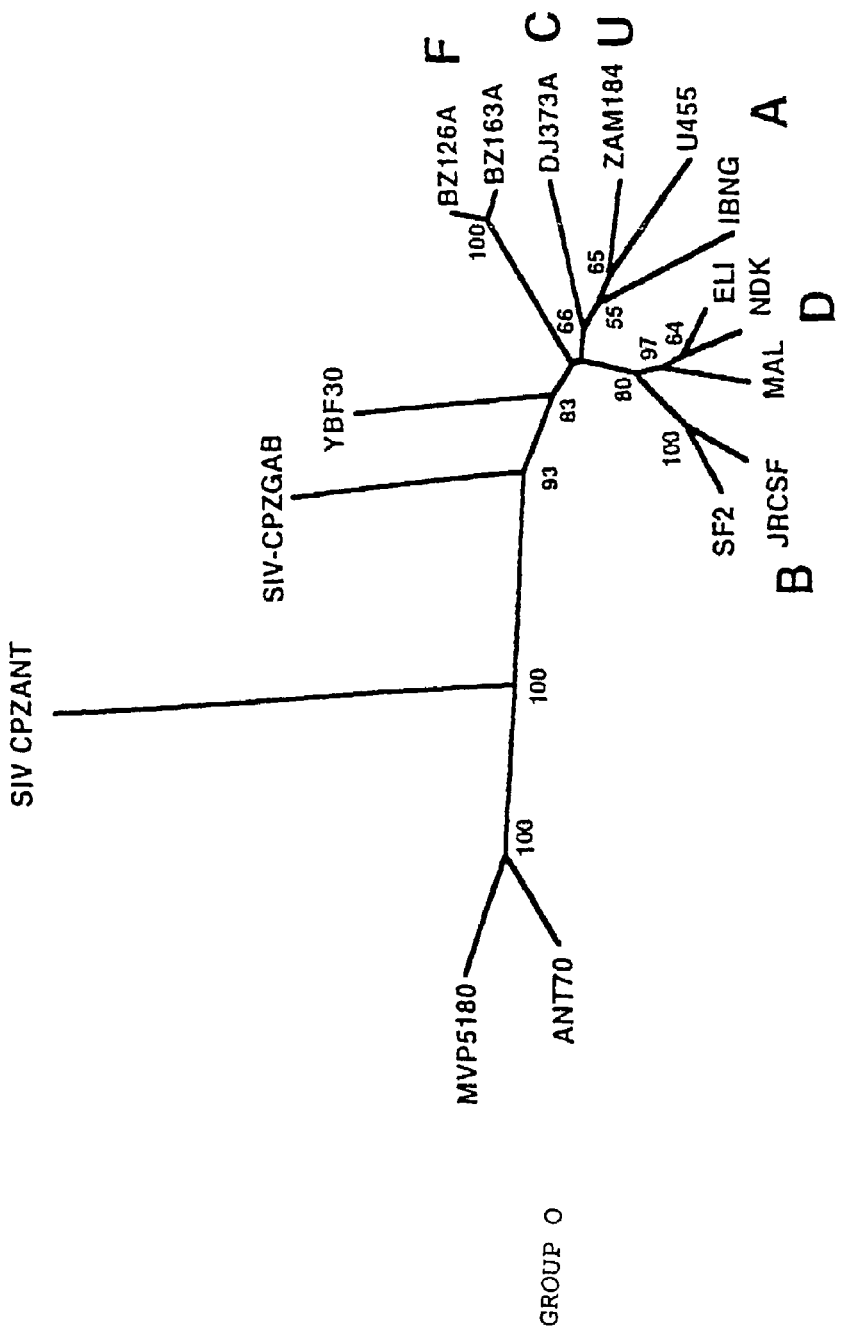
Figure 12:
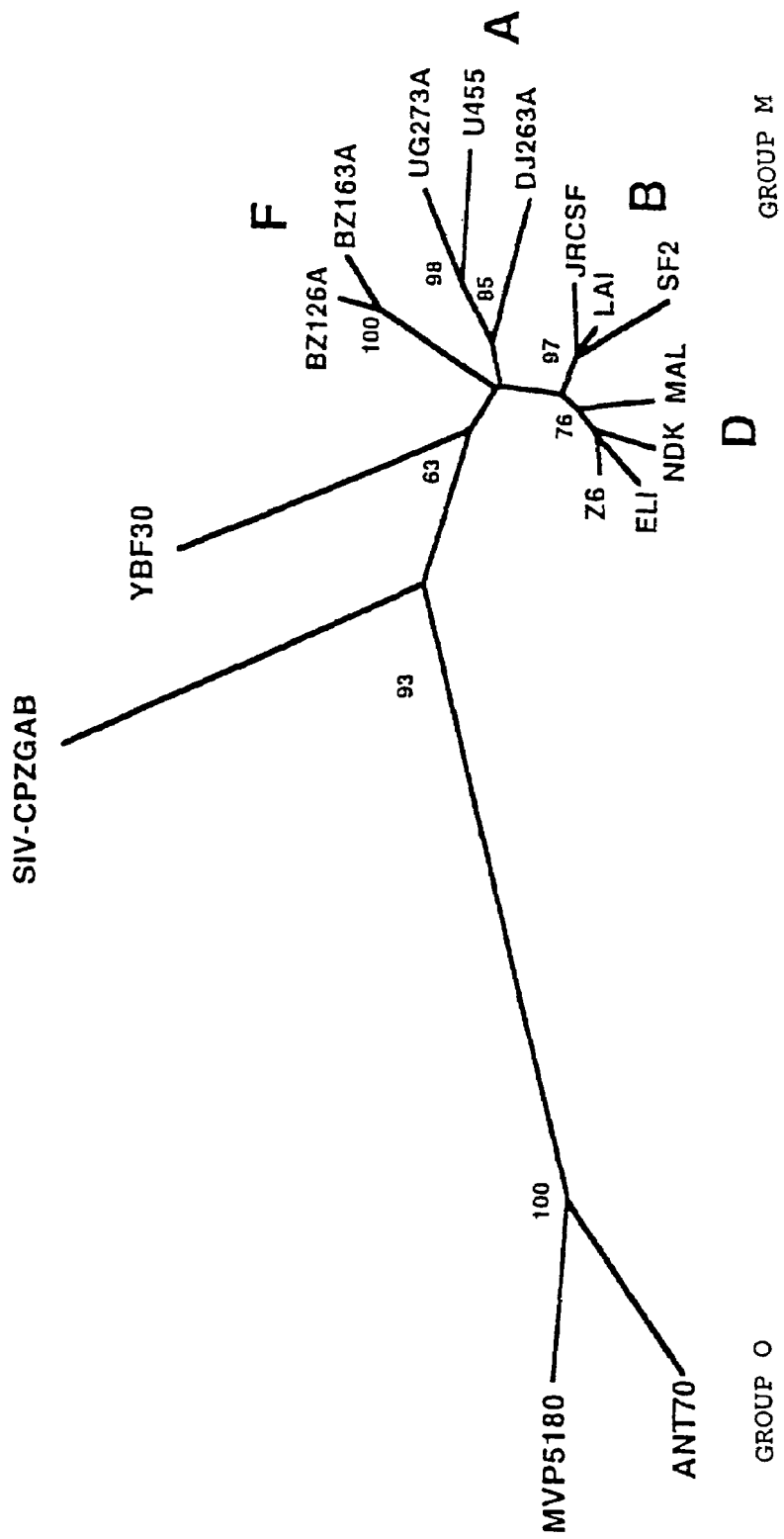
Figure 13:
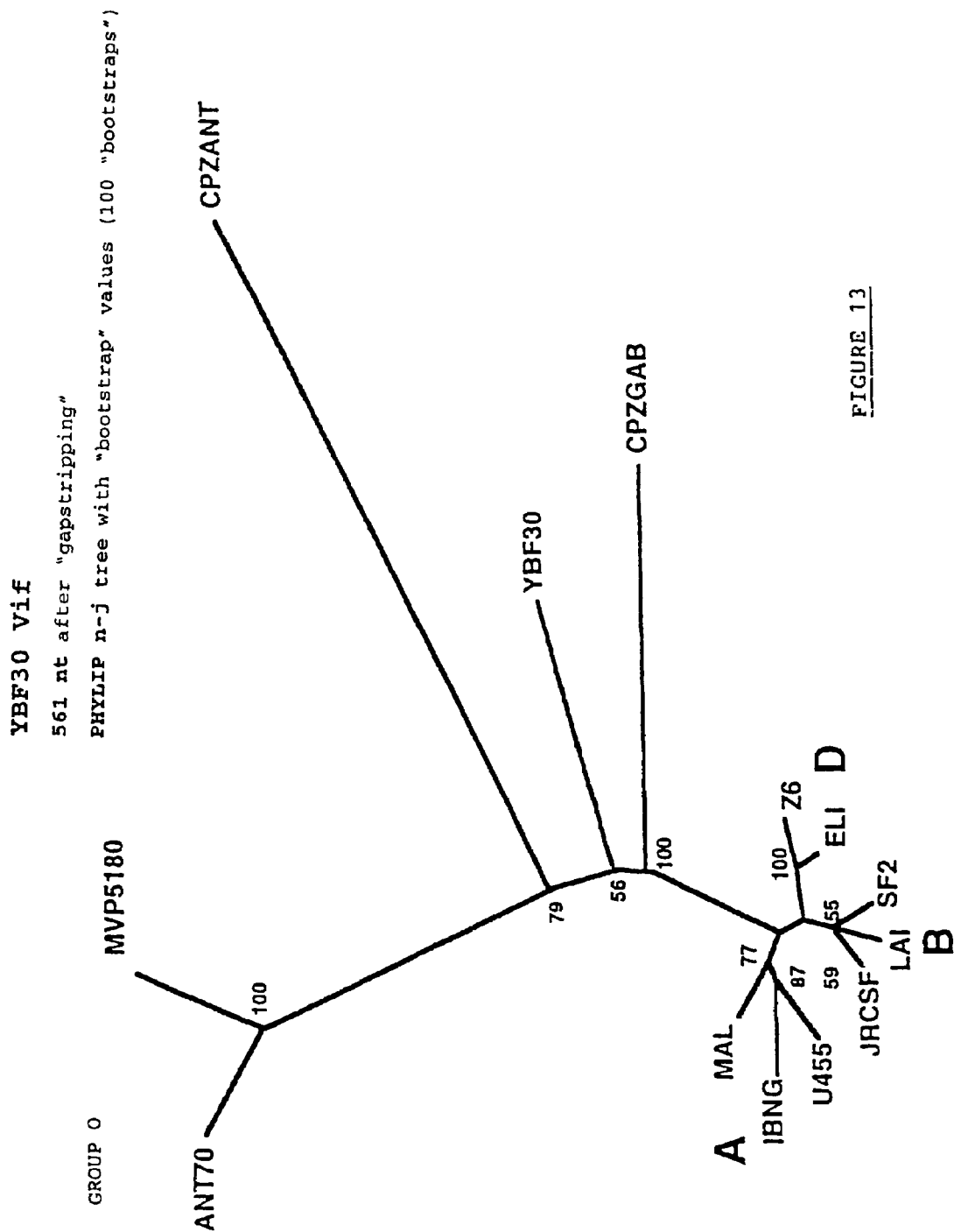
Figure 14:
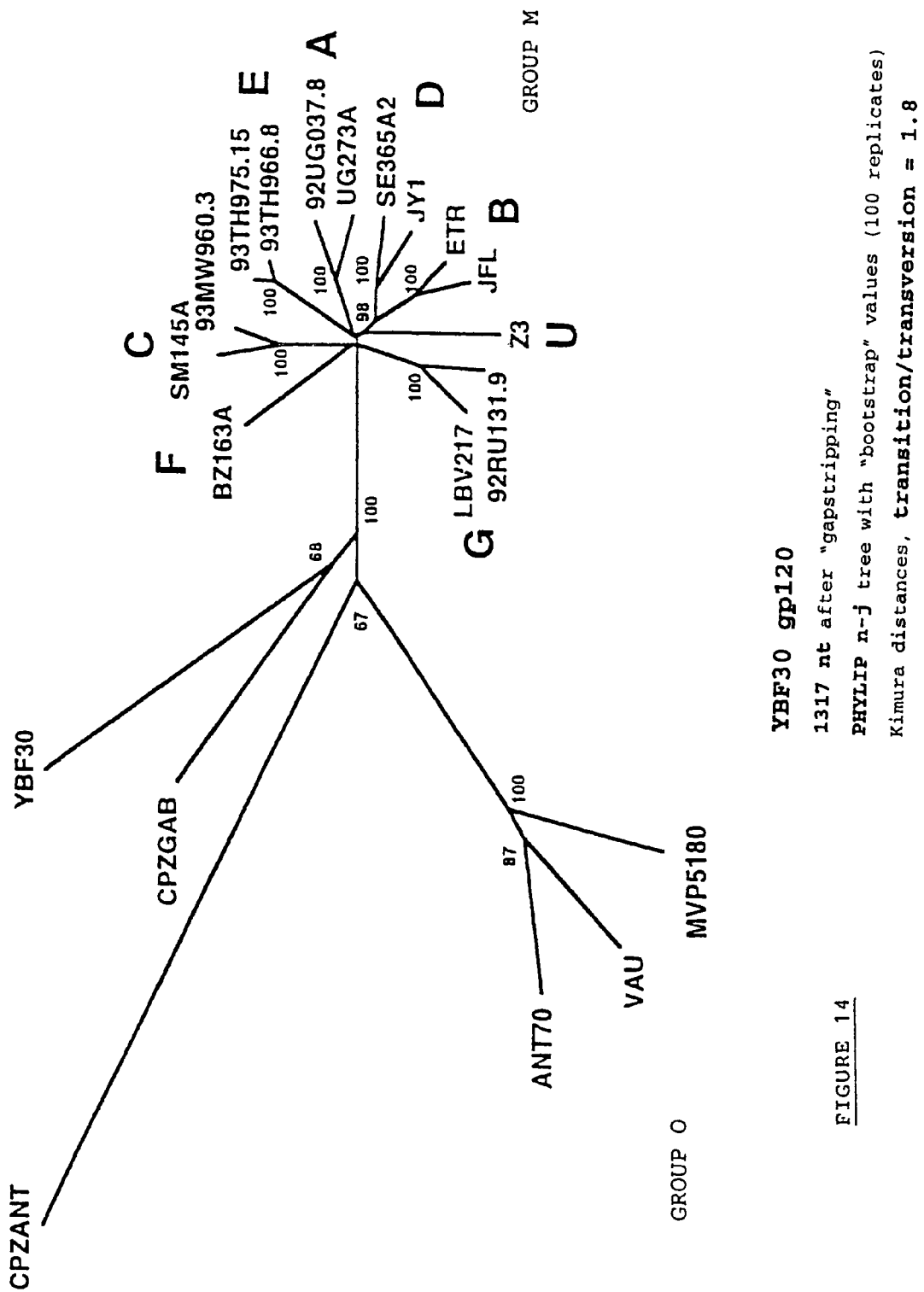
Figure 15:
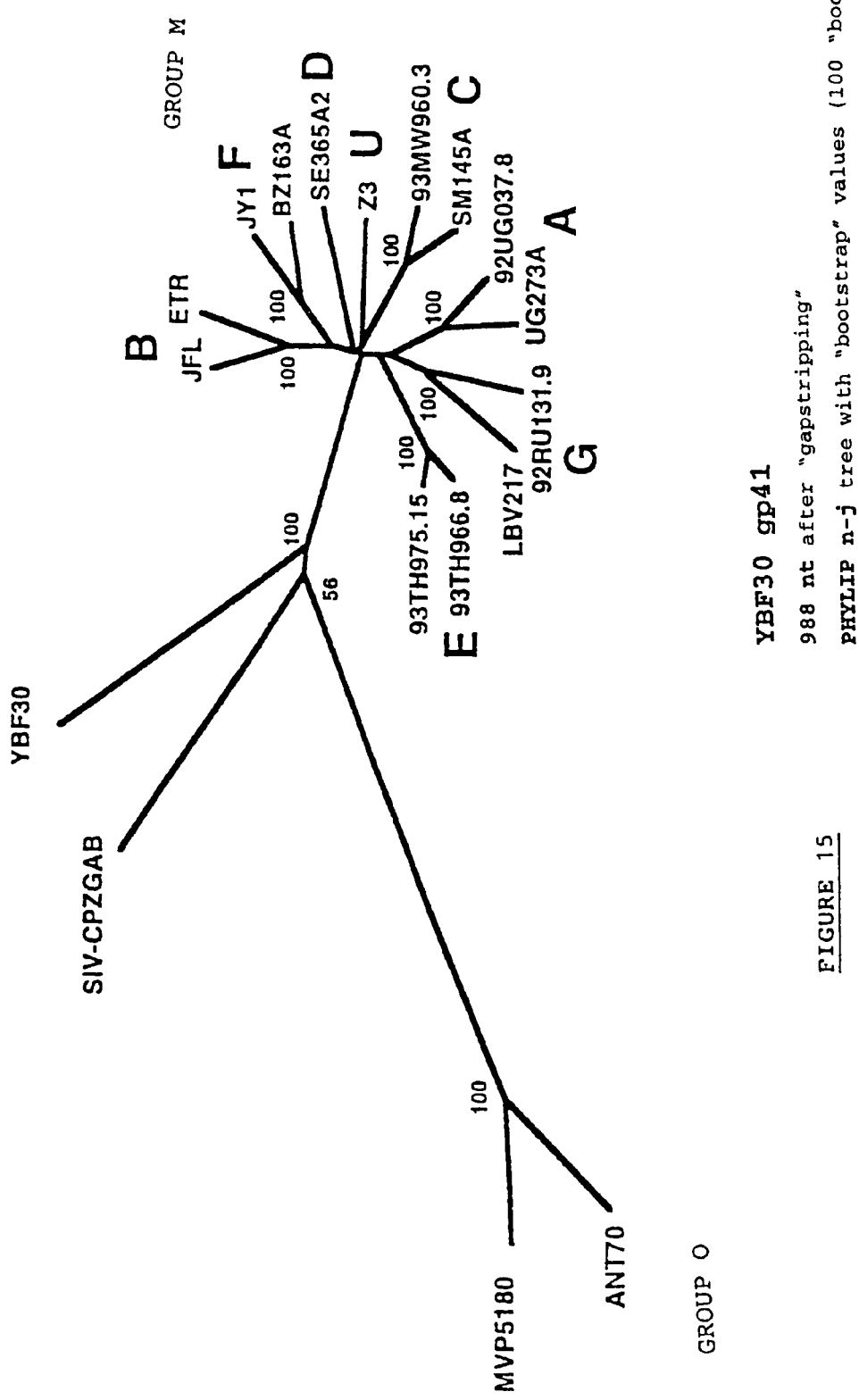
Figure 16:
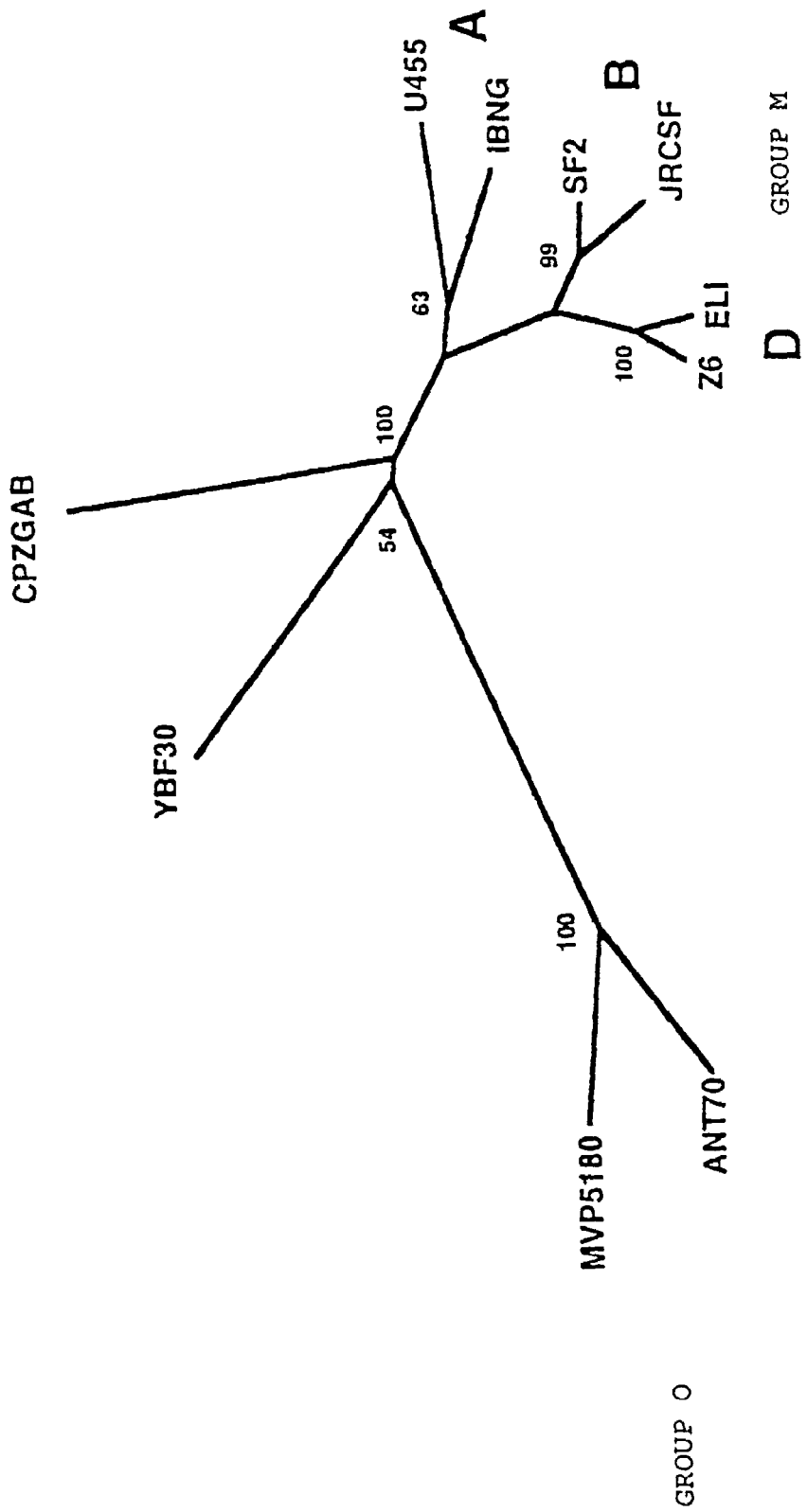
Figure 17:
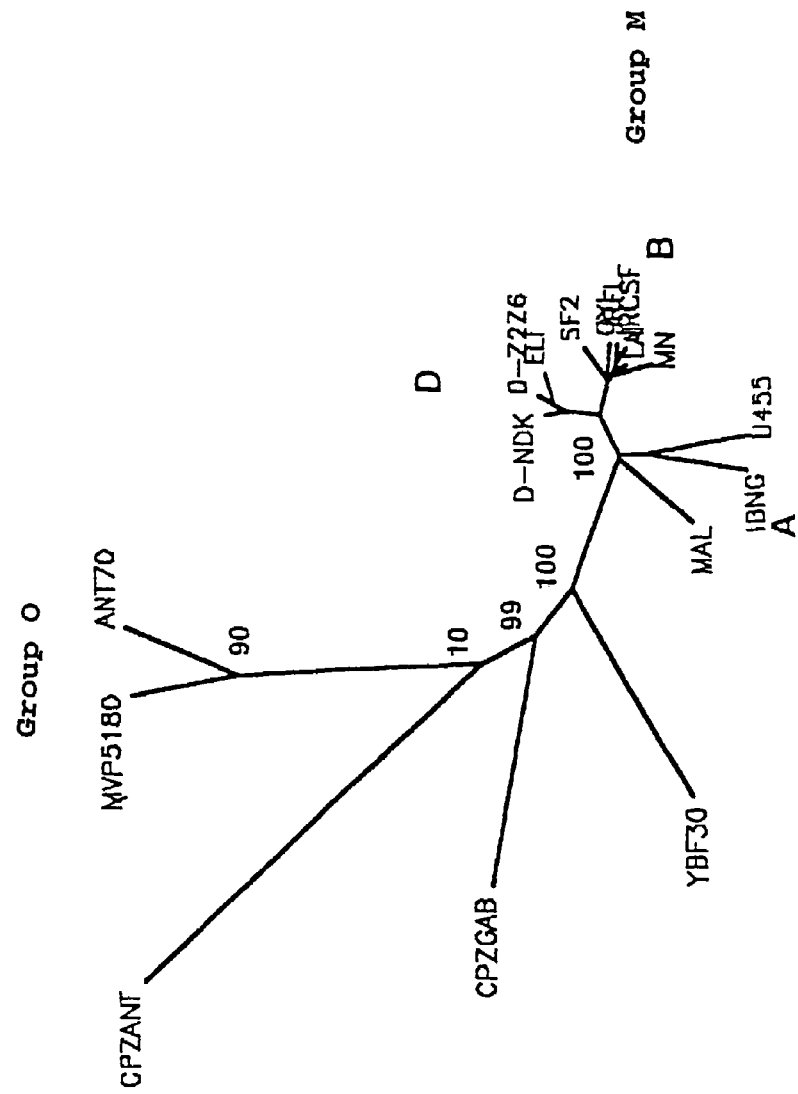
Figure 18:
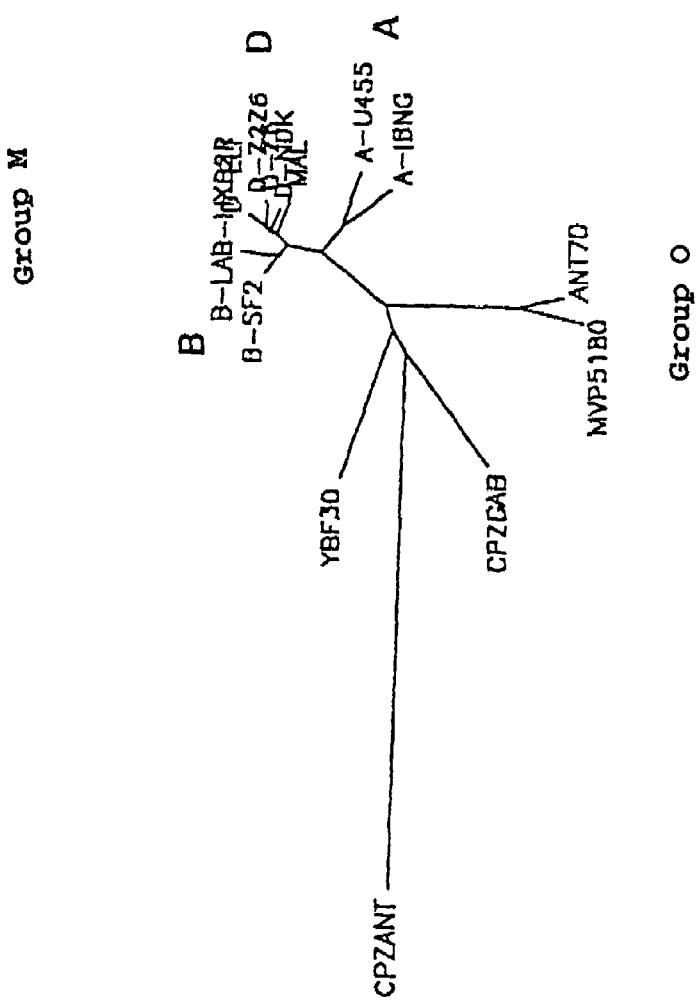
Figure 19:
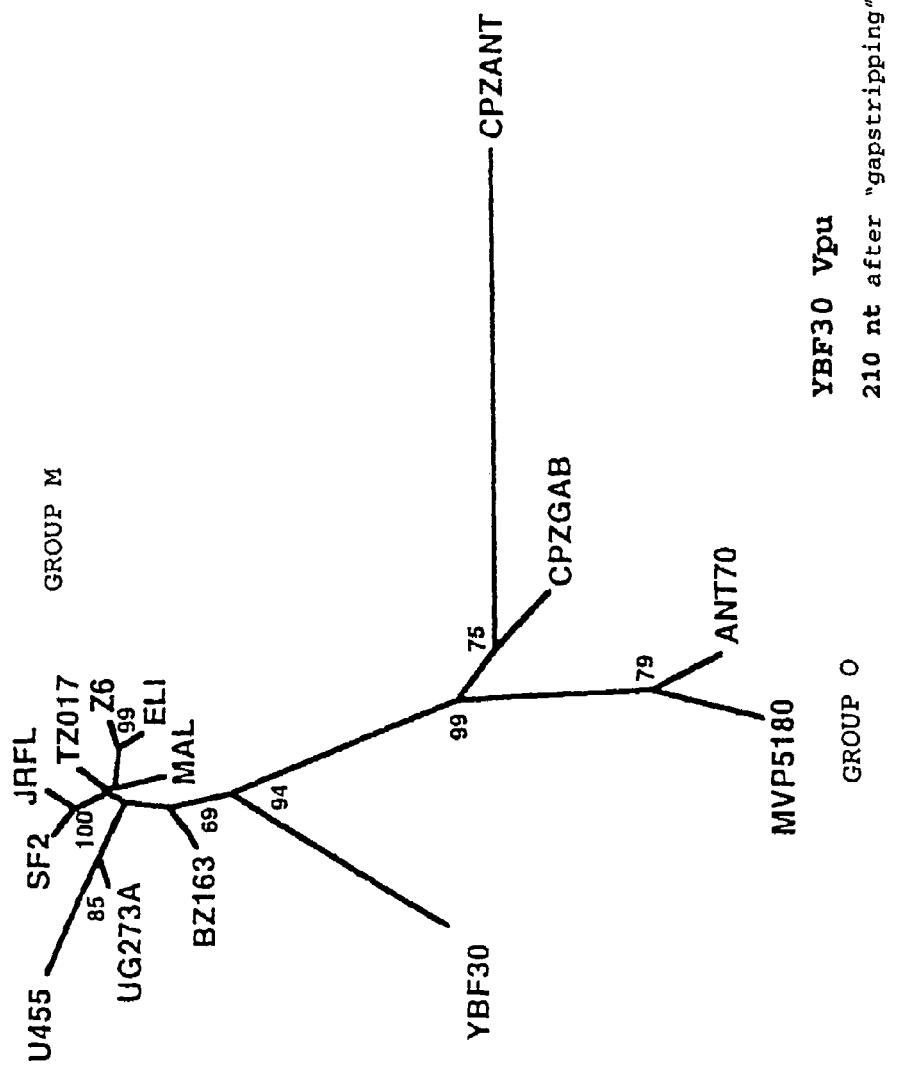

The phylogenetic analyses were performed using the PHYLIP software; the distances were firstly calculated using DNADIST, after which the phylogenetic analysis was carried out using NEIGBOR JOINING or FITCH; finally, the trees were drawn using DRAWTREE (FIGS. 9 to 19). The genetic distance percentages are also shown in FIG. 20.

SEQBOOT was first of all used for the "bootstrapping" analyses, followed by DNADIST and NEIGHBOR JOINING or FITCH. Finally, the bootstrap values were obtained using CONSENS.

II—Results of the Investigation for Detecting Group O and Variant HIV Viruses:

174 samples, out of 3193 samples found to be positive in the screening, were regarded as being group O or group M with abnormal serological reactivity or as being variants.

III—Detection of a Non-group O and Non-group M Sample Exhibiting Abnormal Serological Reactivity The 174 sera which were HIV-1-positive by WB (Western blot), but reactive with a CO/OD ratio of <5 in the competitive EIA, were tested by differential LIA dot blot on the V3 peptides from group M, group O and CPZGAB SIV:

7 do not react with any of the peptides represented (M, O or CPZGAB SIV). The absence of any cell collection does not allow any conclusion to be drawn.

82 give a reactivity with regard to at least one of the peptides corresponding to the V3 loop of O group strains. The frequency of the crossreactions is low and restricted to the epitopes which correspond to the consensus V3 regions (11%) and to the CPZGAB SIV V3 regions (43%).

84 sera do not react with the O group epitopes. Most of these samples were obtained from patients exhibiting an AIDS syndrome (75/84).

one serum, which was taken from a Cameroonian patient (NJ) reacts exclusively with the CPZGAB SIV peptide. This isolated reactivity with regard to a CPZGAB SIV antigen has never been described previously. Since lymphocytes had been collected from the patient, it was possible to continue with the virological characterization of this strain, which was termed YBF30.

IV—Results of the Serological and Virological Examinations Performed on the First Samples Taken from this Patient (May 1995) (Serum No.: 95-6295):

1) Commercial ELISA Tests (optical density/threshold value)

Criterion of positivity: OD/CO>1

Génélavia=>15

Wellcozyme CO/OD=1.55

Abbott Plus=>15

Behring Plus=4.2

2) Western Blot

New Lav 1 Pasteur WB:

160++, 120++, 68++, 55+, 41+, 40+/−, 34++, 24++, 18+

3) Innogenetics LIA Dot Blot

Negative for all the group O and group M bands apart from CPZGAB SIV V3

4) Results of the Investigative Serological Examinations Carried Put on Peptides Which Are Specific for the M and O Groups The technique developed by Professor Francis Barin of the Virology Laboratory of the Tours CHU was modified (Barin F. et al., 1996); use was made of synthesized transmembrane region peptides (BioMérieux) for developing a test for differentiating between the M and O groups. This technique is based on antibody-binding competition between the transmembrane gp41 peptides of the O and M groups, which are deposited on the solid phase, and gp41 transmembrane peptides either of the O group or of the M group at higher concentration in a hyperosmolar liquid reaction phase. The results are shown in Table I below, in which the CP well corresponds to the 100% inhibition control and the CSP well corresponds to the 0% inhibition control.

TABLE I

| | Results of the inter-group O-group M differentiations for the 6295 serum | | | |
|---|---|---|---|---|
| | gp41 M | gp41 O | CP | CSP |
| 6295 | 0.25 | 0.36 | 0.12 | 1.98 |

These results demonstrate that there is strong binding with regard to the peptides of the solid phase (CSP) and a marked inhibition due to the combined addition of the M and O peptides (CP), but no clear differentiation either by the M peptide or by the O peptide. This is, therefore, serological evidence that the infecting strain does not belong either to the M group or to the O group.

In view of an isolated reactivity in the InnoLia dot blot with regard to the CPZGAB SIV V3 antigens, on the same bases of competition between peptides, this serum was studied by bringing into competition the gp41 M, gp41 O and gp41 CPZGAB SIV peptides.

Use of the serum from the chimpanzee named 'Amandine' (donated by M. Peeters, who isolated the CPZGAB SIV strain, AIDS 1992) initially enabled this technique to be validated. In Table II, the lowest values (OD) indicate the highest degree of binding to the antigens.

TABLE II

Results of the inter-group O-group M-CPZGAB SIV differentiations using the Amandine chimpanzee serum and the 6295 serum

|  | gp41 M | gp41 O | gp41 CPZGAB | CP | CSP |
|---|---|---|---|---|---|
| Amandine | 0.8 | 1.4 | 0.3 | 0.5 | 1.9 |
| 6295 | 0.7 | 1.1 | 0.7 | 0.4 | 2.1 |

The reactivity of the "Amandine" serum confirms and validates the test according to the invention and shows that, while the serum of the patient reacts identically with regard to the M and CPZGAB SIV peptides, it does not exhibit a crossreaction with the O peptide.

These results demonstrate that the group M gp41 and CPZGAB SIV gp41 peptides exert a similar inhibition on the serum of the patient. The antigens of the infecting strain have therefore given rise to antibodies which recognize the group M and CPZGAB SIV gp41 peptides in a similar manner.

4) Results Obtained from the Lymphocyte Isolation (Sampling of May 1995)

A retrovirus was isolated, using standard techniques, from the lymphocytes which were sampled on 22 May 1995. Culture using the MT2 cell line shows that the YBF30 strain does not form any syncytia (NSI).

V—Results of the Serological Examinations Carried Out on the Second Blood Sample (November 1995) (Serum No. 95-3371)

1) Innogenetics LIA Dot Blot

Negative for all the bands, apart from CPZGAB SIV V3

2) Results of the Investigative Serological Examinations Carried Out on the Peptides Specific for the M and O Groups.

Table III shows the results of the inter-group O-group M-CPZGAB SIV gp41 differentiations using the 3371 serum.

TABLE III

Results of the inter-group O-group M-CPZGAB SIV gp41 differentiations using the 3371 serum

|  | gp41 M | gp41 O | gp41 CPZGAB | CP | CSP |
|---|---|---|---|---|---|
| 3371 | 1.31 | 1.7 | 0.89 | 0.54 | 2.02 |

These results confirm, on this new blood sample (taken from the same patient in the terminal stage of the disease), that the CPZGAB SIV gp41 peptide markedly inhibits the serum of the patient.

The antigens of the infecting strain have therefore induced antibodies which preferentially recognize the CPZGAB SIV gp41 peptide.

3) Results from the Lymphocyte Isolation (Blood Sampling of November 95 (95-3371-YBF31))

A retrovirus was isolated, using the standard techniques, from the lymphocytes which were sampled in November 1995 and termed YBF31; the sequence elements are identical to those of YBF30.

VI—Genomic Amplification and Sequences of YBF30

The DNA for all the PCR manipulations is extracted from the cells obtained at the end of a positive culture.

The PCRs carried out using the O group HIV-1 primers are negative in the different regions tested (gag, pol, env). Similarly, those carried out using the primers which are specific for M group HIV-1 are also negative.

The amplification and hybridization conditions for the O group PCRs are those described in Loussert-Ajaka, 1995. The amplification and hybridization conditions for the M group PCRs are those described by the authors cited below.

These M group primers are located in accordance with the HIV-1 HXB2 sequence as follows:

in env gp120: ED3/ED12 (position 5956-5985; 7822-7792); ED5/ED14 (6556-6581; 7960-7931); ED5/ED12; ED3/ED14; ES7/ES8 (7001-7020; 7667-7647) (Delwart et al. Science 1993; 262: 1257-1261).

in env gp41 first PCR, ED3/M29, followed by a nested PCR, M28/M29 (7785-7808; 8099-8124); M28/M29 have the following sequences:

```
                                        (SEQ ID NO: 99)
M28:   CGGTTCTT(AG)GGAGCAGC(ACT)GGAAGCA, (SEQ ID NO: 100)
M29:   T(CT)T(ACGT)TCCCA(CT)T(AT)(CT)A(AGT)CCA(AGT)
       GTCAT;
```

SK68/SK69 (Ou et al. Science, 1988; 239: 295-297).

in gag: Amplicor Roche Diagnostics systems; nested gag primers (Loussert-Ajaka et al. Lancet 1995; 346: 912-913); SK38/SK39 (Ou et al., Science, 1988; 239: 295-297).

in pol: A/NE1 (Boucher et al., Lancet, 1990; 336: 585-590); Pol3/Pol4 (Laure et al., Lancet, 1988, ii, 538-541).

Only the PCRs carried out using the H Pol primers (4235/4538) are positive, with this being followed by a nested PCR using the primers 4327/4481 (Fransen et al., Molecular and Cellular Probes 1994; 8: 317-322). This H Pol fragment, which is located in the integrase (260 bp), has been sequenced. Amplification using the HPOL primers is made possible due to the excess of virus. This is because the DNA which is used is extracted from cells at the end of a strongly positive culture (reverse transcriptase>100,000 cpm). It is not possible to amplify the DNA which is extracted from fresh cells without coculture because of the large number of mispairings between the HPOL primers (especially in the 3' region) and the sequence of the YBF30 isolate. Conservation of this 3' end is very important for the extension activity of the Taq polymerase.

1 - Sequence of the poi gene: the use of very degenerate primers for amplifying, by RT-PCR, the RNA extracted from the positive culture supernatant gave a positive amplification. These are primers which are common to all retroviruses (Donehower et al. J. Virol. Methods 1990; 28: 33-46), and are located in the reverse transcriptase region of the pol gene. Analysis of the fragment after sequencing made it possible to generate a specific primer, i.e. YRT2 (SEQ ID NO: 32), from the YBF30 isolate and to amplify the pol gene using the Hpol 4481 primer (Fransen et al., 1994, loc. cit.) as the antisense primer. The fragment was sequenced by synthesizing specific primers as required for each fragment generated (FIG. 1).

2 - Sequence of the env gene: the second approach was to perform a long PCR (XL-PCR, Perkin Elmer), thereby amplifying all the virus (9000 bp) using primers situated in the LTR: LPBS 1 (SEQ ID NO: 22); LSiGi, followed by a 6000 bp nested PCR using YRT2 (SEQ ID NO: 32)SK69, and to sequence all the envelope following the same procedure. The gp41 region was sequenced using a nested PCR and employing the primers SK68/LSiGi.

3—Sequence of the gag gene: use of a nested PCR, achieved by means of a long PCR (LPBS 1/LSiGi), employing the primers Gag 5 and Gag 11i, and generating from this specific primers, as required, in order to walk along the viral genome.

VII—Results of the Sequencings

The strain YBF30 was sequenced completely (see list of sequences). The YBF31 strain of November 1995 was sequenced in part, and the absence of significant variation confirms the validity of the YBF30 sequences.

VIII—Synthesizing Peptides of the V3 Loop Region of the YBF30 Strain.

Studying the sequences of the V3 loop region made it possible to synthesize the corresponding peptide and to compare the amino acids of this region of the YBF30 strain with those of other M subtypes and O strains.

The sequences of the peptides are:

```
YBF30:        SEQ ID NO: 58

CPZGAB SIV:   CHRPGNNTRGEVQIGPGMTFYNIENVYGDTRSAYC
              (SEQ ID NO: 59)

GROUP O:      CIRPGNRTYRNLQIGPGMTFYNVEIATGDIRKAFC
(ANT70)       (SEQ ID NO: 60)

GROUP M:      CTRPNNNTRKSVRIGPGQAFYATGDIIGDIRQAHC
(SS-TYPE A)   (SEQ ID NO: 61)
```

The peptide was synthesized, starting with the two asparagines of the 5' region of the loop, and used in accordance with the same principle as previously described (see IV 4)), namely in competition in relation to the peptides of the M group, the O group and CPZGAB SIV. The results shown in Table IV confirm the original nature of this strain and the possible spread of these strains, since the serological results favour infection of the YBF30 type in Cameroon. Furthermore, a study of 200 selected HIV-1-positive sera from Cameroon provides evidence of a new case exhibiting a profile which is similar to that of YBF30.

TABLE IV

Study of the reactivity of 200 sera

| Serum | Origin | V3A | V3cpz | V3YBF30 | CP | CSP |
|---|---|---|---|---|---|---|
| 953371 | Cameroon | 1.66 | 0.38 | 1.39 | 0.39 | 1.64 |
| 956295 | Cameroon | 1.72 | 0.37 | 1.16 | 0.51 | 1.73 |
| 967321 | Cameroon | 0.07 | 0.17 | 0.5 | 0.05 | 0.27 |
| Amandine | GABSIV | 1.74 | 0.14 | 1.48 | 0.19 | 1.74 |
| NOA.* | ANTSIV | 2.66 | 0.31 | 1.88 | 0.46 | 1.9 |

*serum from CPZ ANT SIV

The reactivity of the sera 953371 and 956295, corresponding to the patient from whom the YBF30 strain was isolated, with the CPZ SIV peptide, was confirmed in this new test. The lower reactivity with regard to its own V3 antigen is usual during the late stages of the disease. Nevertheless, this reactivity remains greater than that raised with regard to the M peptide. Another Cameroonian patient (serum 967321) exhibits the same profile of peptide reactivity.

REFERENCES

Barin F. et al., Aids Research and Human Retroviruses, 1996, 12, 13, 1279-1289, *Diversity of Antibody Binding to V3 Peptides Representing Consensus Sequences of HIV Type 1 Genotypes A to E: An Approach for HIV Type 1 Serological Subtyping.*

Charneau P., Borman A M., Quillent C., Guétard D., Chamaret S., Cohen J., Rémy G., Montagnier L., and F. Clavel, Virology, 1994, 205, 247-253, *Isolation and envelope sequence of a highly divergent HIV-1 isolate: definition of a new HIV-1 group.*

Descamps D., Collin G., Loussert-Ajaka I., Saragosti S., Simon F. and F. Brun-Vezinet. AIDS, 1995, 9, 977-978, *HIV-1 group O sensitivity to antiretroviral drugs.*

Huet, T., Cheynier R., Meyerhans A., Roelants G., and S. Wain-Hobson, Nature, 1990, 345, 356-359, *Genetic organization of a chimpanzee lentivirus related to HIV-1.*

Korber B T M., MacInnes K., Smith R. and G. Myers, J. Virol., 1994, 68, 6730-6744, *Mutational trends in V3 loop protein sequences observed in different genetic lineages of HIV-1.*

Loussert-Ajaka I., Ly T D., Chaix M L, Ingrand D., Saragosti S., Couroucé A M., Brun-Vezinet F. and F. Simon, Lancet, 1994, 343, 1393-1394, *HIV-1/HIV-2 seronegativity in HIV-1 subtype O infected patients.*

Loussert-Ajaka I., Chaix M L., Korber B., Letourneur F., Gomas E., Allen E., Ly T D., Brun-Fezinet F., Simon F. and S. Saragosti, J. Virol., 1995, 69, 5640-5649, *Variability of HIV type 1 group O strains isolated from Cameroonian patients living in FRANCE.*

Murphy, E., B. Korber, Georges-Courbot, M C., You B., Pinter A., Cook D., Kienky M P., Georges A., Mathiot C., Barre-Sinoussi F., and M. Girard, AIDS Res. Hum. Retroviruses, 1993, 9, 997-1006, *Diversity of V3 region sequences of human immunodeficiency viruses type 1 from the Central African Republic.*

G. Myers, Aids Res. Hum. Retrovir., 1994, 10, 11, 1317-1324, *Tenth Anniversary Perspectives on AIDS.*

Nkengasong, J. N., Janssens W., Heyndrickx L., Fransen K., Ndumbe P M., Motte J., Leonaers A., Ngolle M., Ayuk J., Piot P., and G. Van der Groen, AIDS, 1994, 8, 1405-1412, *Genotypic subtypes of HIV-1 in Cameroon.*

Sharp P. M. et al., AIDS, 1994, 8, suppl. 1, S27-S42, *Origins and diversity of human immunodeficiency viruses.*

Simon, F., T. D. Ly, A. Baillou-Beaufils, V. Schneider-Fauveau, J. de Saint-Martin, I. Loussert-Ajaka, M. L. Chaix, S. Saragosti, A. M. Couroucé, D. Ingrand, C. Janot, and F. Brun-Vezinet. AIDS, 1994, 8, 1628-1629. *Sensitivity of screening kits for anti-HIV-1 subtype O antibodies.*

Zekeng, L., L. Gurtler, E. Afane Ze, A. Sam-Abbenyi, G. Mbouni, Essomba, E. Mpoudi-Ngolle, M. Monny-Lobbe, J. B. Tapko, and L. Kaptue, AIDS, 1994, 8, 1626-1628, *Prevalence of HIV-1 subtype O infection in Cameroon: preliminary results.*

As is evident from the above, the invention is in no way limited to those of its embodiments which have just been described more explicitly; on the contrary, it encompasses all the variants which may come to the mind of the skilled person without departing from the context or scope of the present invention.

The invention claimed is:

1. An isolated nucleic acid, wherein the nucleic acid comprises SEQ ID NO: 5.

2. An isolated nucleic acid, wherein the nucleic acid consists of SEQ ID NO: 5.

3. An isolated oligonucleotide, characterized in that it comprises a sequence selected from SEQ ID NOs: 29 to 40, and in that it is capable of being used as a primer or as a probe for detecting SEQ ID NO: 5.

4. A reagent for diagnosing a non-M, non-O HIV-1 virus, characterized in that it comprises an isolated nucleic acid according to claim 1 or 2.

5. A method for screening and typing a non-M, non-O HIV-1 virus, characterized in that it comprises bringing an isolated nucleic acid according to claim 1 or 2 into contact with the nucleic acid of the virus to be typed and detecting any hybrid which is formed.

6. A kit for diagnosing a non-M, non-O HIV-1 virus, characterized in that it includes at least one reagent according to claim 4.

7. An isolated oligonucleotide, wherein the oligonucleotide comprises at least 10 nucleotides and is included in a sequence selected from the group consisting of SEQ ID NOs: 29 to 40.

8. An isolated oligonucleotide, wherein the oligonucleotide comprises a sequence selected from the group consisting of SEQ ID NOs: 29 to 40.

9. A reagent for diagnosing a non-M, non-O HIV-1 virus, characterized in that it comprises an oligonucleotide according to claim 3, 7, or 8.

10. A method for screening and typing a non-M, non-O HIV-1 virus, characterized in that it comprises bringing an oligonucleotide according to claim 3, 7, or 8 into contact with the nucleic acid of the virus to be typed and detecting any hybrid which is formed.

* * * * *